(12) United States Patent
Hacking et al.

(10) Patent No.: US 11,596,829 B2
(45) Date of Patent: Mar. 7, 2023

(54) CONTROL SYSTEM FOR A REHABILITATION AND EXERCISE ELECTROMECHANICAL DEVICE

(71) Applicant: ROM TECHNOLOGIES, INC., Las Vegas, NV (US)

(72) Inventors: S. Adam Hacking, Nashua, NH (US); Daniel Lipszyc, Glasgow, MT (US)

(73) Assignee: Rom Technologies, Inc., Brookfield, CT (US)

( * ) Notice: Subject to any disclaimer, the term of this patent is extended or adjusted under 35 U.S.C. 154(b) by 184 days.

(21) Appl. No.: 16/813,303

(22) Filed: Mar. 9, 2020

(65) Prior Publication Data
US 2020/0289881 A1 Sep. 17, 2020

Related U.S. Application Data

(60) Provisional application No. 62/816,503, filed on Mar. 11, 2019.

(51) Int. Cl.
*A63B 22/06* (2006.01)
*A63B 21/00* (2006.01)
(Continued)

(52) U.S. Cl.
CPC ........ *A63B 22/0605* (2013.01); *A61B 5/1121* (2013.01); *A61B 5/221* (2013.01);
(Continued)

(58) Field of Classification Search
CPC ............ A61H 1/0214; A63B 21/00072; A63B 21/00178–00181; A63B 21/0058;
(Continued)

(56) References Cited

U.S. PATENT DOCUMENTS 59,915 A 11/1866 Lallement
363,522 A 5/1887 Knous
(Continued)

FOREIGN PATENT DOCUMENTS

CA 2698078 A1 3/2010
CN 112603295 A 2/2003
(Continued)

OTHER PUBLICATIONS

Claris Healthcare Inc.; Claris Reflex Patient Rehabilitation System Brochure, https://clarisreflex.com/, retrieved from internet on Oct. 2, 2019; 5 pages.
(Continued)

*Primary Examiner* — Jennifer Robertson
(74) *Attorney, Agent, or Firm* — Dickinson Wright PLLC; Stephen A. Mason; Jonathan H. Harder

(57) ABSTRACT

An electromechanical device for rehabilitation includes pedals coupled to radially-adjustable couplings, an electric motor coupled to the pedals via the radially-adjustable couplings, and a control system including a processing device operatively coupled to the electric motor. The processing device configured to, responsive to a first trigger condition occurring, control the electric motor to operate in a passive mode by independently driving the radially-adjustable couplings rotationally coupled to the pedals. The processing device also configured to, responsive to a second trigger condition occurring, control the electric motor to operate in an active-assisted mode by measuring revolutions per minute of the radially-adjustable couplings, and cause the electric motor to drive the radially-adjustable couplings when the measured revolutions per minute satisfy a threshold condition, and responsive to a third trigger condition occurring, control the electric motor to operate in a resistive (Continued)

mode by providing resistance to rotation of the radially-adjustable couplings.

19 Claims, 37 Drawing Sheets

(51) Int. Cl.
| | | |
|---|---|---|
| A63B 24/00 | (2006.01) | |
| A63B 71/00 | (2006.01) | |
| A61H 1/02 | (2006.01) | |
| A63B 21/005 | (2006.01) | |
| G16H 20/30 | (2018.01) | |
| A61B 5/11 | (2006.01) | |
| A61B 5/22 | (2006.01) | |
| G06F 3/04817 | (2022.01) | |
| G06F 3/0482 | (2013.01) | |
| H04N 5/232 | (2006.01) | |
| A61B 5/00 | (2006.01) | |
| A63B 71/06 | (2006.01) | |
| G06F 3/04847 | (2022.01) | |
| A63B 22/00 | (2006.01) | |

(52) U.S. Cl.
CPC ....... *A61H 1/0214* (2013.01); *A63B 21/0058* (2013.01); *A63B 21/00072* (2013.01); *A63B 21/00178* (2013.01); *A63B 21/00181* (2013.01); *A63B 21/4034* (2015.10); *A63B 24/0062* (2013.01); *A63B 24/0075* (2013.01); *A63B 71/0054* (2013.01); *G06F 3/0482* (2013.01); *G06F 3/04817* (2013.01); *G16H 20/30* (2018.01); *H04N 5/232* (2013.01); *A61B 5/4824* (2013.01); *A61B 5/6812* (2013.01); *A63B 71/0622* (2013.01); *A63B 2022/0094* (2013.01); *A63B 2024/0068* (2013.01); *A63B 2024/0093* (2013.01); *A63B 2024/0096* (2013.01); *A63B 2071/0081* (2013.01); *A63B 2071/0647* (2013.01); *A63B 2071/0658* (2013.01); *A63B 2071/0675* (2013.01); *A63B 2209/08* (2013.01); *A63B 2220/17* (2013.01); *A63B 2220/24* (2013.01); *A63B 2220/40* (2013.01); *A63B 2220/51* (2013.01); *A63B 2220/807* (2013.01); *A63B 2220/833* (2013.01); *A63B 2220/836* (2013.01); *A63B 2225/096* (2013.01); *A63B 2225/20* (2013.01); *A63B 2225/52* (2013.01); *G06F 3/04847* (2013.01)

(58) Field of Classification Search
CPC ............ A63B 21/4034; A63B 24/0087; A63B 2024/0093; A63B 71/0054; A63B 2071/0081; A63B 2220/40; A63B 2220/51; A63B 2220/833; A63B 23/0476; A63B 22/06–0658
See application file for complete search history.

(56) References Cited

U.S. PATENT DOCUMENTS

| | | |
|---|---|---|
| 446,671 A | 2/1891 | Elliott |
| 610,157 A | 8/1898 | Campbell |
| 631,276 A | 8/1899 | Bulova |
| 823,712 A | 6/1906 | Uhlmann |
| 1,149,029 A | 8/1915 | Clark |
| 1,227,743 A | 5/1917 | Burgedorff |
| 1,784,230 A | 12/1930 | Freeman |
| 3,081,645 A | 3/1963 | Bergfors |
| 3,100,640 A | 8/1963 | Weitzel |
| 3,137,014 A | 6/1964 | Meucci |
| 3,143,316 A | 8/1964 | Shapiro |
| 3,713,438 A | 1/1973 | Knutsen |
| 3,744,480 A | 7/1973 | Gause et al. |
| 3,888,136 A | 6/1975 | Lapeyre |
| 4,079,957 A | 3/1978 | Blease |
| 4,408,613 A | 10/1983 | Relyea |
| 4,436,097 A | 3/1984 | Cunningham |
| 4,446,753 A | 5/1984 | Nagano |
| 4,477,072 A | 10/1984 | DeCloux |
| 4,499,900 A | 2/1985 | Petrofsky et al. |
| 4,509,742 A | 4/1985 | Cones |
| 4,606,241 A | 8/1986 | Fredriksson |
| 4,611,807 A | 9/1986 | Castillo |
| 4,616,823 A | 10/1986 | Yang |
| 4,648,287 A | 3/1987 | Preskitt |
| 4,673,178 A | 6/1987 | Dwight |
| 4,822,032 A | 4/1989 | Whitmore et al. |
| 4,824,104 A | 4/1989 | Bloch |
| 4,850,245 A | 7/1989 | Feamster et al. |
| 4,858,942 A | 8/1989 | Rodriguez |
| 4,869,497 A | 9/1989 | Stewart et al. |
| 4,915,374 A | 4/1990 | Watkins |
| 4,930,768 A | 6/1990 | Lapcevic |
| 4,932,650 A | 6/1990 | Bingham et al. |
| 4,961,570 A | 10/1990 | Chang |
| 5,137,501 A * | 8/1992 | Mertesdorf ........ A63B 71/0622 482/57 |
| 5,161,430 A | 11/1992 | Febey |
| 5,202,794 A | 4/1993 | Schnee et al. |
| 5,240,417 A | 8/1993 | Smithson et al. |
| 5,247,853 A | 9/1993 | Dalebout |
| 5,256,115 A | 10/1993 | Scholder et al. |
| 5,256,117 A | 10/1993 | Potts et al. |
| D342,299 S | 12/1993 | Birrell et al. |
| 5,282,748 A | 2/1994 | Little |
| 5,284,131 A | 2/1994 | Gray |
| 5,316,532 A | 5/1994 | Butler |
| 5,324,241 A | 6/1994 | Artigues et al. |
| 5,336,147 A | 8/1994 | Sweeney, III |
| 5,338,272 A | 8/1994 | Sweeney, III |
| 5,361,649 A | 11/1994 | Slocum, Jr. |
| D353,421 S | 12/1994 | Gallivan |
| 5,429,140 A | 7/1995 | Burdea et al. |
| 5,458,022 A | 10/1995 | Mattfeld et al. |
| 5,487,713 A | 1/1996 | Butler |
| 5,566,589 A | 10/1996 | Buck |
| 5,580,338 A | 12/1996 | Scelta et al. |
| 5,676,349 A | 10/1997 | Wilson |
| 5,685,804 A | 11/1997 | Whan-Tong et al. |
| 5,738,636 A | 4/1998 | Saringer et al. |
| 5,860,941 A | 1/1999 | Saringer et al. |
| 5,950,813 A | 9/1999 | Hoskins et al. |
| 6,053,847 A | 4/2000 | Stearns et al. |
| 6,077,201 A | 6/2000 | Cheng |
| 6,102,834 A | 8/2000 | Chen |
| 6,110,130 A | 8/2000 | Kramer |
| 6,155,958 A | 12/2000 | Goldberg |
| 6,182,029 B1 | 1/2001 | Friedman |
| D438,580 S | 3/2001 | Shaw |
| 6,253,638 B1 | 7/2001 | Bermudez |
| 6,267,735 B1 | 7/2001 | Blanchard et al. |
| 6,273,863 B1 | 8/2001 | Avni et al. |
| D450,100 S | 11/2001 | Hsu |
| D450,101 S | 11/2001 | Hsu |
| D451,972 S | 12/2001 | Easley |
| D452,285 S | 12/2001 | Easley |
| D454,605 S | 3/2002 | Lee |
| 6,371,891 B1 | 4/2002 | Speas |
| D459,776 S | 7/2002 | Lee |
| 6,413,190 B1 | 7/2002 | Wood et al. |
| 6,430,436 B1 | 8/2002 | Richter |
| 6,436,058 B1 | 8/2002 | Krahner et al. |
| 6,474,193 B1 | 11/2002 | Farney |
| 6,491,649 B1 | 12/2002 | Ombrellaro |
| 6,535,861 B1 | 3/2003 | OConnor et al. |
| 6,543,309 B2 | 4/2003 | Heim |
| D475,424 S | 6/2003 | Lee |
| 6,589,139 B1 | 7/2003 | Butterworth |

(56) References Cited

U.S. PATENT DOCUMENTS

| | | |
|---|---|---|
| 6,602,191 B2 | 8/2003 | Quy |
| 6,626,805 B1 | 9/2003 | Lightbody |
| D482,416 S | 11/2003 | Yang |
| 6,640,662 B1 | 11/2003 | Baxter |
| 6,652,425 B1 | 11/2003 | Martin et al. |
| D484,931 S | 1/2004 | Tsai |
| 6,820,517 B1 | 11/2004 | Farney |
| 6,865,969 B2 | 3/2005 | Stevens |
| 6,890,312 B1 | 5/2005 | Priester et al. |
| 6,895,834 B1 | 5/2005 | Baalz |
| 7,156,665 B1 | 1/2007 | OConnor et al. |
| 7,156,780 B1 | 1/2007 | Fuchs et al. |
| 7,169,085 B1 | 1/2007 | Killin et al. |
| 7,204,788 B2 | 4/2007 | Andrews |
| 7,209,886 B2 | 4/2007 | Kimmel |
| 7,226,394 B2 | 6/2007 | Johnson |
| RE39,904 E | 10/2007 | Lee |
| 7,406,003 B2 | 7/2008 | Burkhardt et al. |
| D575,836 S | 8/2008 | Hsiao |
| 7,507,188 B2 | 3/2009 | Nurre |
| 7,594,879 B2 | 9/2009 | Johnson |
| 7,726,034 B2 | 6/2010 | Wixey |
| 7,778,851 B2 | 8/2010 | Schoenberg et al. |
| 7,809,601 B2 | 10/2010 | Shaya et al. |
| 7,833,135 B2 | 11/2010 | Radow et al. |
| 7,837,472 B1 | 11/2010 | Elsmore et al. |
| 7,955,219 B2 | 6/2011 | Birrell et al. |
| 7,974,689 B2 | 7/2011 | Volpe et al. |
| 7,988,599 B2 | 8/2011 | Ainsworth et al. |
| 8,079,937 B2 | 12/2011 | Bedell et al. |
| 8,287,434 B2 | 10/2012 | Zavadsky et al. |
| 8,419,593 B2 | 4/2013 | Ainsworth et al. |
| 8,465,398 B2 | 6/2013 | Lee et al. |
| 8,506,458 B2 | 8/2013 | Dugan |
| 8,540,515 B2 | 9/2013 | Williams et al. |
| 8,540,516 B2 | 9/2013 | Williams et al. |
| 8,556,778 B1 | 10/2013 | Dugan |
| 8,607,465 B1 | 12/2013 | Edwards |
| 8,613,689 B2 | 12/2013 | Dyer et al. |
| 8,672,812 B2 | 3/2014 | Dugan |
| 8,751,264 B2 | 6/2014 | Beraja et al. |
| 8,784,273 B2 | 7/2014 | Dugan |
| 8,823,448 B1 | 9/2014 | Shen |
| 8,864,628 B2 | 10/2014 | Boyette et al. |
| 8,979,711 B2 | 3/2015 | Dugan |
| 9,044,630 B1 | 6/2015 | Lampert et al. |
| 9,167,281 B2 | 10/2015 | Petrov |
| D744,050 S | 11/2015 | Colburn |
| 9,248,071 B1 | 2/2016 | Benda et al. |
| 9,272,185 B2 | 3/2016 | Dugan |
| 9,283,434 B1 * | 3/2016 | Wu .............. A61B 5/6895 |
| 9,311,789 B1 | 4/2016 | Gwin |
| 9,312,907 B2 | 4/2016 | Auchinleck et al. |
| 9,367,668 B2 | 6/2016 | Flynt et al. |
| 9,409,054 B2 | 8/2016 | Dugan |
| 9,443,205 B2 | 9/2016 | Wall |
| 9,480,873 B2 | 11/2016 | Chuang |
| 9,481,428 B2 | 11/2016 | Gros et al. |
| 9,566,472 B2 | 2/2017 | Dugan |
| 9,579,056 B2 | 2/2017 | Rosenbek et al. |
| 9,629,558 B2 | 4/2017 | Yuen et al. |
| 9,713,744 B2 | 7/2017 | Suzuki |
| D793,494 S | 8/2017 | Mansfield et al. |
| D794,142 S | 8/2017 | Zhou |
| 9,717,947 B2 | 8/2017 | Lin |
| 9,737,761 B1 * | 8/2017 | Sivaraj .................. G16H 20/30 |
| 9,782,621 B2 | 10/2017 | Chiang et al. |
| 9,802,076 B2 | 10/2017 | Murray et al. |
| 9,872,087 B2 | 1/2018 | DelloStritto et al. |
| 9,872,637 B2 | 1/2018 | Kording et al. |
| 9,914,053 B2 | 3/2018 | Dugan |
| 9,919,198 B2 | 3/2018 | Romeo et al. |
| 9,937,382 B2 | 4/2018 | Dugan |
| 9,939,784 B1 | 4/2018 | Berardinelli |
| 10,074,148 B2 | 9/2018 | Cashman et al. |
| 10,130,298 B2 | 11/2018 | Mokaya et al. |
| 10,155,134 B2 | 12/2018 | Dugan |
| 10,159,872 B2 | 12/2018 | Sasaki et al. |
| 10,173,094 B2 | 1/2019 | Gomberg |
| 10,173,095 B2 | 1/2019 | Gomberg et al. |
| 10,173,096 B2 | 1/2019 | Gomberg et al. |
| 10,173,097 B2 | 1/2019 | Gomberg et al. |
| 10,226,663 B2 | 3/2019 | Gomberg et al. |
| 10,254,804 B2 | 4/2019 | Dusan |
| 10,325,070 B2 | 6/2019 | Beale et al. |
| 10,327,697 B1 | 6/2019 | Stein et al. |
| 10,424,033 B2 | 9/2019 | Romeo |
| 10,430,552 B2 | 10/2019 | Mihai |
| 10,542,914 B2 | 1/2020 | Forth et al. |
| 10,546,467 B1 | 1/2020 | Luciano, Jr. et al. |
| 10,569,122 B2 | 2/2020 | Johnson |
| 10,572,626 B2 | 2/2020 | Balram |
| 10,576,331 B2 | 3/2020 | Kuo |
| 10,625,114 B2 | 4/2020 | Ercanbrack |
| 10,646,746 B1 | 5/2020 | Gomberg et al. |
| 10,660,534 B2 | 5/2020 | Lee et al. |
| 10,678,890 B2 | 6/2020 | Bitran et al. |
| 10,685,092 B2 | 6/2020 | Paparella et al. |
| 10,705,619 B2 | 7/2020 | Johri |
| 10,777,200 B2 | 9/2020 | Will et al. |
| 10,792,495 B2 | 10/2020 | Izvorski et al. |
| 10,874,905 B2 | 12/2020 | Belson et al. |
| D907,143 S | 1/2021 | Ach et al. |
| 10,918,332 B2 | 2/2021 | Belson et al. |
| 10,931,643 B1 | 2/2021 | Neumann |
| 11,000,735 B2 | 5/2021 | Orady et al. |
| 11,040,238 B2 | 6/2021 | Colburn |
| 11,045,709 B2 | 6/2021 | Putnam |
| 11,065,527 B2 | 7/2021 | Putnam |
| 11,069,436 B2 | 7/2021 | Mason et al. |
| 11,071,597 B2 | 7/2021 | Posnack et al. |
| 11,075,000 B2 | 7/2021 | Mason et al. |
| D928,635 S | 8/2021 | Hacking et al. |
| 11,087,865 B2 | 8/2021 | Mason et al. |
| 11,101,028 B2 | 8/2021 | Mason et al. |
| 11,107,591 B1 | 8/2021 | Mason |
| 11,139,060 B2 | 10/2021 | Mason et al. |
| 11,185,735 B2 | 11/2021 | Am et al. |
| D939,644 S | 12/2021 | Ach et al. |
| D940,797 S | 1/2022 | Ach et al. |
| 11,229,727 B2 | 1/2022 | Tatonetti |
| 11,270,795 B2 | 3/2022 | Mason et al. |
| 11,272,879 B2 | 3/2022 | Wiedenhoefer et al. |
| 11,282,599 B2 | 3/2022 | Mason et al. |
| 11,282,604 B2 | 3/2022 | Mason et al. |
| 11,282,608 B2 | 3/2022 | Mason et al. |
| 11,284,797 B2 | 3/2022 | Mason et al. |
| D948,639 S | 4/2022 | Ach et al. |
| 11,295,848 B2 | 4/2022 | Mason et al. |
| 11,309,085 B2 | 4/2022 | Mason et al. |
| 11,317,975 B2 | 5/2022 | Mason et al. |
| 11,325,005 B2 | 5/2022 | Mason et al. |
| 11,328,807 B2 | 5/2022 | Mason et al. |
| 11,337,648 B2 | 5/2022 | Mason |
| 11,348,683 B2 | 5/2022 | Guaneri et al. |
| 11,404,150 B2 | 8/2022 | Guaneri et al. |
| 11,410,768 B2 | 8/2022 | Mason et al. |
| 2002/0072452 A1 | 6/2002 | Torkelson |
| 2002/0160883 A1 | 10/2002 | Dugan |
| 2003/0036683 A1 | 2/2003 | Kehr et al. |
| 2003/0045402 A1 * | 3/2003 | Pyle .................. A63B 21/00178 482/51 |
| 2003/0064863 A1 | 4/2003 | Chen |
| 2003/0083596 A1 | 5/2003 | Kramer et al. |
| 2003/0092536 A1 | 5/2003 | Romanelli et al. |
| 2003/0109814 A1 * | 6/2003 | Rummerfield ........ A61H 1/0214 601/24 |
| 2003/0181832 A1 | 9/2003 | Carnahan et al. |
| 2004/0102931 A1 | 5/2004 | Ellis et al. |
| 2004/0106502 A1 | 6/2004 | Sher |
| 2004/0147969 A1 | 7/2004 | Mann et al. |
| 2004/0172093 A1 * | 9/2004 | Rummerfield ..... A63B 22/0605 607/43 |
| 2004/0194572 A1 | 10/2004 | Kim |

(56) References Cited

U.S. PATENT DOCUMENTS

| | | |
|---|---|---|
| 2005/0015118 A1 | 1/2005 | Davis et al. |
| 2005/0020411 A1 | 1/2005 | Andrews |
| 2005/0043153 A1 | 2/2005 | Krietzman |
| 2005/0049122 A1 | 3/2005 | Vallone et al. |
| 2005/0085346 A1 | 4/2005 | Johnson |
| 2005/0085353 A1 | 4/2005 | Johnson |
| 2005/0274220 A1 | 12/2005 | Reboullet |
| 2006/0003871 A1 | 1/2006 | Houghton et al. |
| 2006/0046905 A1 | 3/2006 | Doody, Jr. et al. |
| 2006/0064329 A1 | 3/2006 | Abolfathi et al. |
| 2006/0199700 A1 | 9/2006 | LaStayo et al. |
| 2006/0247095 A1* | 11/2006 | Rummerfield ........ A61H 1/0214 482/57 |
| 2007/0042868 A1 | 2/2007 | Fisher et al. |
| 2007/0137307 A1 | 6/2007 | Gruben et al. |
| 2007/0173392 A1 | 7/2007 | Stanford |
| 2007/0287597 A1 | 12/2007 | Cameron |
| 2008/0021834 A1 | 1/2008 | Holla et al. |
| 2008/0153592 A1 | 6/2008 | James-Herbert |
| 2008/0161166 A1 | 7/2008 | Lo |
| 2008/0300914 A1 | 12/2008 | Karkanias et al. |
| 2009/0011907 A1 | 1/2009 | Radow et al. |
| 2009/0046056 A1 | 2/2009 | Rosenberg et al. |
| 2009/0058635 A1 | 3/2009 | LaLonde et al. |
| 2009/0070138 A1 | 3/2009 | Langheier et al. |
| 2009/0211395 A1 | 8/2009 | Mule |
| 2009/0270227 A1 | 10/2009 | Ashby et al. |
| 2010/0048358 A1 | 2/2010 | Tchao et al. |
| 2010/0121160 A1 | 5/2010 | Stark et al. |
| 2010/0173747 A1 | 7/2010 | Chen et al. |
| 2010/0248899 A1 | 9/2010 | Bedell et al. |
| 2010/0248905 A1 | 9/2010 | Lu |
| 2010/0268304 A1 | 10/2010 | Matos |
| 2010/0298102 A1 | 11/2010 | Bosecker et al. |
| 2011/0047108 A1 | 2/2011 | Chakrabarty et al. |
| 2011/0172059 A1 | 7/2011 | Watterson et al. |
| 2011/0195819 A1 | 8/2011 | Shaw et al. |
| 2011/0218814 A1 | 9/2011 | Coats |
| 2011/0275483 A1 | 11/2011 | Dugan |
| 2012/0065987 A1 | 3/2012 | Farooq et al. |
| 2012/0116258 A1 | 5/2012 | Lee |
| 2012/0167709 A1 | 7/2012 | Chen et al. |
| 2012/0183939 A1 | 7/2012 | Aragones et al. |
| 2012/0190502 A1 | 7/2012 | Paulus et al. |
| 2012/0295240 A1 | 11/2012 | Walker et al. |
| 2012/0310667 A1 | 12/2012 | Altman et al. |
| 2013/0123667 A1 | 5/2013 | Komatireddy et al. |
| 2013/0137550 A1 | 5/2013 | Skinner et al. |
| 2013/0178334 A1 | 7/2013 | Brammer |
| 2013/0296987 A1 | 11/2013 | Rogers et al. |
| 2013/0318027 A1 | 11/2013 | Almogy et al. |
| 2013/0345025 A1 | 12/2013 | van der Merwe |
| 2014/0006042 A1 | 1/2014 | Keefe et al. |
| 2014/0011640 A1 | 1/2014 | Dugan |
| 2014/0113768 A1 | 4/2014 | Lin et al. |
| 2014/0155129 A1 | 6/2014 | Dugan |
| 2014/0172460 A1 | 6/2014 | Kohli |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0207264 A1 | 7/2014 | Quy |
| 2014/0207486 A1 | 7/2014 | Carty et al. |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0309083 A1 | 10/2014 | Dugan |
| 2014/0322686 A1 | 10/2014 | Kang |
| 2015/0045700 A1 | 2/2015 | Cavanagh et al. |
| 2015/0088544 A1 | 3/2015 | Goldberg |
| 2015/0151162 A1 | 6/2015 | Dugan |
| 2015/0158549 A1 | 6/2015 | Gros et al. |
| 2015/0161331 A1 | 6/2015 | Oleynik |
| 2015/0290061 A1 | 10/2015 | Stafford et al. |
| 2015/0339442 A1 | 11/2015 | Oleynik |
| 2015/0341812 A1 | 11/2015 | Dion et al. |
| 2015/0379232 A1 | 12/2015 | Mainwaring et al. |
| 2016/0007885 A1 | 1/2016 | Basta et al. |
| 2016/0023081 A1 | 1/2016 | Popa-Simil et al. |
| 2016/0117471 A1 | 4/2016 | Belt et al. |
| 2016/0140319 A1 | 5/2016 | Stark et al. |
| 2016/0151670 A1 | 6/2016 | Dugan |
| 2016/0166881 A1 | 9/2016 | Nolan et al. |
| 2016/0275259 A1 | 9/2016 | Nolan et al. |
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2016/0325140 A1 | 11/2016 | Wu |
| 2016/0332028 A1 | 11/2016 | Melnik |
| 2017/0014671 A1 | 1/2017 | Burns, Sr. |
| 2017/0033375 A1 | 2/2017 | Ohmori et al. |
| 2017/0042467 A1 | 2/2017 | Herr et al. |
| 2017/0046488 A1 | 2/2017 | Pereira |
| 2017/0065851 A1 | 3/2017 | Deluca et al. |
| 2017/0080320 A1 | 3/2017 | Smith |
| 2017/0004260 A1 | 4/2017 | Johnson |
| 2017/0095670 A1 | 4/2017 | Ghaffar et al. |
| 2017/0095692 A1 | 4/2017 | Chang et al. |
| 2017/0095693 A1 | 4/2017 | Chang et al. |
| 2017/0106242 A1 | 4/2017 | Dugan |
| 2017/0113092 A1* | 4/2017 | Johnson ............. A63B 22/0015 |
| 2017/0128769 A1 | 5/2017 | Long et al. |
| 2017/0132947 A1 | 5/2017 | Maeda et al. |
| 2017/0136296 A1 | 5/2017 | Barrera et al. |
| 2017/0143261 A1 | 5/2017 | Wiedenhoefer et al. |
| 2017/0147789 A1 | 5/2017 | Wiedenhoefer et al. |
| 2017/0168555 A1 | 6/2017 | Munoz et al. |
| 2017/0181698 A1 | 6/2017 | Wiedenhoefer et al. |
| 2017/0190052 A1 | 7/2017 | Jaekel et al. |
| 2017/0209766 A1 | 7/2017 | Riley et al. |
| 2017/0243028 A1 | 9/2017 | Olsen et al. |
| 2017/0265800 A1 | 9/2017 | Auchinleck et al. |
| 2017/0266501 A1 | 9/2017 | Sanders et al. |
| 2017/0278209 A1 | 10/2017 | Stein et al. |
| 2017/0282015 A1 | 10/2017 | Wicks et al. |
| 2017/0300654 A1 | 10/2017 | McRaith et al. |
| 2017/0312614 A1 | 11/2017 | Tran et al. |
| 2017/0329917 A1 | 11/2017 | Duffy et al. |
| 2017/0333755 A1 | 11/2017 | Rider |
| 2017/0337033 A1 | 11/2017 | Duyan et al. |
| 2017/0337334 A1 | 11/2017 | Stanczak |
| 2017/0344726 A1 | 12/2017 | Dempers et al. |
| 2017/0360586 A1 | 12/2017 | Dempers et al. |
| 2017/0368413 A1 | 12/2017 | Shavit |
| 2018/0017806 A1 | 1/2018 | Wang et al. |
| 2018/0052962 A1 | 3/2018 | Gomberg et al. |
| 2018/0056104 A1 | 3/2018 | Cromie et al. |
| 2018/0071565 A1 | 3/2018 | Gomberg et al. |
| 2018/0071566 A1 | 3/2018 | Gomberg et al. |
| 2018/0071569 A1 | 3/2018 | Gomberg et al. |
| 2018/0071570 A1 | 3/2018 | Gomberg et al. |
| 2018/0071571 A1 | 3/2018 | Gomberg et al. |
| 2018/0071572 A1 | 3/2018 | Gomberg et al. |
| 2018/0075205 A1 | 3/2018 | Moturu et al. |
| 2018/0078843 A1 | 3/2018 | Tran et al. |
| 2018/0085615 A1 | 4/2018 | Hogue et al. |
| 2018/0116741 A1 | 5/2018 | Garcia Kilroy et al. |
| 2018/0178061 A1 | 6/2018 | O'larte et al. |
| 2018/0199855 A1 | 7/2018 | Odame et al. |
| 2018/0200577 A1 | 7/2018 | Dugan |
| 2018/0102190 A1 | 8/2018 | Tuyl et al. |
| 2018/0220935 A1 | 8/2018 | Tadano et al. |
| 2018/0228682 A1* | 8/2018 | Bayerlein .......... A63B 71/0622 |
| 2018/0253991 A1 | 9/2018 | Tang et al. |
| 2018/0256079 A1 | 9/2018 | Yang et al. |
| 2018/0263530 A1 | 9/2018 | Jung |
| 2018/0271432 A1 | 9/2018 | Auchinleck et al. |
| 2018/0272184 A1 | 9/2018 | Vassilaros et al. |
| 2018/0280784 A1 | 10/2018 | Romeo et al. |
| 2018/0296157 A1 | 10/2018 | Bleich et al. |
| 2018/0240552 A1 | 11/2018 | Athey et al. |
| 2018/0330058 A1 | 11/2018 | Bates |
| 2018/0330824 A1 | 11/2018 | Athey et al. |

(56) References Cited

U.S. PATENT DOCUMENTS

| | | |
|---|---|---|
| 2018/0360340 A1 | 12/2018 | Rehse et al. |
| 2018/0373844 A1 | 12/2018 | Ferrandez-Escamez et al. |
| 2019/0030415 A1 | 1/2019 | Volpe, Jr. |
| 2019/0031284 A1 | 1/2019 | Fuchs |
| 2019/0035043 A1 | 1/2019 | Jones et al. |
| 2019/0019578 A1 | 2/2019 | Kang et al. |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0088356 A1 | 3/2019 | Oliver et al. |
| 2019/0091506 A1* | 3/2019 | Gatelli ............... A63B 21/4034 |
| 2019/0111299 A1 | 4/2019 | Radcliffe et al. |
| 2019/0115097 A1 | 4/2019 | Macoviak et al. |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Celia et al. |
| 2019/0167988 A1 | 6/2019 | Shahriar et al. |
| 2019/0172587 A1 | 6/2019 | Park et al. |
| 2019/0175988 A1 | 6/2019 | Volterrani et al. |
| 2019/0200920 A1 | 7/2019 | Fien et al. |
| 2019/0209891 A1 | 7/2019 | Fung |
| 2019/0240103 A1 | 8/2019 | Hepler et al. |
| 2019/0240541 A1 | 8/2019 | Denton et al. |
| 2019/0244540 A1 | 8/2019 | Errante et al. |
| 2019/0269343 A1 | 9/2019 | Ramos Murguialday et al. |
| 2019/0274523 A1 | 9/2019 | Bates et al. |
| 2019/0304584 A1 | 10/2019 | Savolainen |
| 2019/0307983 A1 | 10/2019 | Goldman |
| 2019/0354632 A1 | 11/2019 | Mital et al. |
| 2019/0366146 A1 | 12/2019 | Tong et al. |
| 2019/0388728 A1 | 12/2019 | Wang et al. |
| 2020/0005928 A1 | 1/2020 | Daniel |
| 2020/0051446 A1 | 2/2020 | Rubinstein et al. |
| 2020/0066390 A1 | 2/2020 | Svendrys et al. |
| 2020/0085300 A1 | 3/2020 | Kwatra et al. |
| 2020/0093418 A1 | 3/2020 | Kluger et al. |
| 2020/0143922 A1 | 5/2020 | Jayalath et al. |
| 2020/0151595 A1 | 5/2020 | Pulitzer et al. |
| 2020/0151646 A1 | 5/2020 | De La Fuente Sanchez |
| 2020/0152339 A1 | 5/2020 | Reeves et al. |
| 2020/0285322 A1 | 5/2020 | Johri |
| 2020/0160198 A1 | 6/2020 | Lucas et al. |
| 2020/0170876 A1 | 6/2020 | Kapure et al. |
| 2020/0197744 A1 | 6/2020 | Schweighofer |
| 2020/0221975 A1 | 7/2020 | Basta et al. |
| 2020/0267487 A1 | 8/2020 | Siva |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289878 A1 | 9/2020 | Am et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0334972 A1 | 10/2020 | Gopalakrishnan |
| 2020/0357299 A1 | 11/2020 | Patel et al. |
| 2020/0395112 A1 | 12/2020 | Ronner |
| 2020/0401224 A1 | 12/2020 | Cotton |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0098129 A1 | 4/2021 | Neumann |
| 2021/0101051 A1 | 4/2021 | Posnack et al. |
| 2021/0113890 A1 | 4/2021 | Posnack et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134425 A1 | 5/2021 | Mason et al. |
| 2021/0134428 A1 | 5/2021 | Mason et al. |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |
| 2021/0202090 A1 | 7/2021 | DDonovan et al. |
| 2021/0202103 A1 | 7/2021 | Bostic et al. |
| 2021/0244998 A1 | 8/2021 | Hacking et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0366587 A1 | 11/2021 | Mason et al. |
| 2021/0383909 A1 | 12/2021 | Mason et al. |
| 2021/0391091 A1 | 12/2021 | Mason |
| 2021/0407670 A1 | 12/2021 | Mason et al. |
| 2021/0407681 A1 | 12/2021 | Mason et al. |
| 2022/0015838 A1 | 1/2022 | Posnack et al. |
| 2022/0047921 A1 | 2/2022 | Bissonnette et al. |
| 2022/0079690 A1 | 3/2022 | Mason et al. |
| 2022/0080256 A1 | 3/2022 | Arn et al. |
| 2022/0105384 A1 | 4/2022 | Hacking et al. |
| 2022/0105385 A1 | 4/2022 | Hacking et al. |
| 2022/0115133 A1 | 4/2022 | Mason et al. |
| 2022/0126169 A1 | 4/2022 | Mason |
| 2022/0148725 A1 | 5/2022 | Mason et al. |
| 2022/0158916 A1 | 5/2022 | Mason et al. |
| 2022/0193491 A1 | 6/2022 | Mason et al. |
| 2022/0230729 A1 | 7/2022 | Mason et al. |
| 2022/0238223 A1 | 7/2022 | Mason et al. |
| 2022/0262483 A1 | 8/2022 | Rosenberg et al. |
| 2022/0266094 A1 | 8/2022 | Mason et al. |
| 2022/0270738 A1 | 8/2022 | Mason et al. |
| 2022/0273986 A1 | 9/2022 | Mason |
| 2022/0288460 A1 | 9/2022 | Mason |
| 2022/0288461 A1 | 9/2022 | Ashley et al. |
| 2022/0288462 A1 | 9/2022 | Ashley et al. |
| 2022/0293257 A1 | 9/2022 | Guaneri et al. |
| 2022/0314075 A1 | 10/2022 | Mason et al. |
| 2022/0328181 A1 | 10/2022 | Mason et al. |
| 2022/0331663 A1 | 10/2022 | Mason |
| 2022/0339501 A1 | 10/2022 | Mason et al. |

FOREIGN PATENT DOCUMENTS

| | | |
|---|---|---|
| CN | 202220794 U | 5/2012 |
| CN | 103488880 A | 1/2014 |
| CN | 104335211 A | 2/2015 |
| CN | 105620643 A | 6/2016 |
| CN | 105683977 A | 6/2016 |
| CN | 105894088 A | 8/2016 |
| CN | 105930668 A | 9/2016 |
| CN | 106127646 A | 11/2016 |
| CN | 106510985 A | 3/2017 |
| CN | 107066819 A | 8/2017 |
| CN | 107430641 A | 12/2017 |
| CN | 107736982 A | 2/2018 |
| CN | 108078737 A | 5/2018 |
| CN | 208573971 U | 3/2019 |
| CN | 110148472 A | 8/2019 |
| CN | 110215188 A | 9/2019 |
| CN | 111105859 A | 5/2020 |
| CN | 111370088 A | 7/2020 |
| CN | 112603295 A | 4/2021 |
| DE | 35019 C | 1/1897 |
| DE | 7628633 U1 | 12/1977 |
| DE | 8519150 U1 | 10/1985 |

(56) References Cited

FOREIGN PATENT DOCUMENTS

| | | |
|---|---|---|
| DE | 3732905 A1 | 7/1988 |
| DE | 19619820 A1 | 12/1996 |
| DE | 29620008 U1 | 2/1997 |
| DE | 19947926 A1 | 4/2001 |
| DE | 102018202497 A1 | 8/2018 |
| DE | 102018211212 A1 | 1/2019 |
| DE | 102019108425 B3 | 8/2020 |
| EP | 199600 A2 | 10/1986 |
| EP | 634319 A2 | 1/1995 |
| EP | 1034817 A1 | 9/2000 |
| EP | 2564904 A1 | 3/2013 |
| EP | 3264303 A1 | 1/2018 |
| EP | 3323473 A1 | 5/2018 |
| EP | 3627514 A1 | 3/2020 |
| EP | 3688537 A1 | 8/2020 |
| EP | 3731733 A1 | 11/2020 |
| FR | 2527541 A2 | 12/1983 |
| GB | 141664 A | 11/1920 |
| GB | 2336140 A | 10/1999 |
| GB | 2372459 A | 8/2002 |
| JP | 2003225875 A | 8/2003 |
| JP | 2013515995 A | 5/2013 |
| JP | 3198173 U | 6/2015 |
| JP | 2019134909 A | 8/2019 |
| JP | 6573739 B1 | 9/2019 |
| JP | 6659831 B2 | 3/2020 |
| JP | 6710357 B1 | 6/2020 |
| JP | 6775757 B1 | 10/2020 |
| JP | 2021027917 A | 2/2021 |
| KR | 20020009724 A | 2/2002 |
| KR | 20020065253 A | 8/2002 |
| KR | 20150017693 A | 2/2015 |
| KR | 20160093990 A | 8/2016 |
| KR | 20170038837 A | 4/2017 |
| KR | 101988167 B1 | 6/2019 |
| KR | 20200025290 A | 3/2020 |
| KR | 102116664 B1 | 5/2020 |
| KR | 102116968 B1 | 5/2020 |
| KR | 20200056233 A | 5/2020 |
| KR | 102120828 B1 | 6/2020 |
| KR | 102142713 B1 | 8/2020 |
| KR | 102162522 B1 | 10/2020 |
| KR | 102173553 B1 | 11/2020 |
| KR | 102180079 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102224618 B1 | 3/2021 |
| KR | 102264498 B1 | 6/2021 |
| WO | 1998009687 | 3/1998 |
| WO | 0149235 A2 | 7/2001 |
| WO | 0151083 A2 | 7/2001 |
| WO | 2001050387 A1 | 7/2001 |
| WO | 2020200891 A1 | 2/2003 |
| WO | 2003043494 | 5/2003 |
| WO | 2006004430 A2 | 1/2006 |
| WO | 2006012694 A1 | 2/2006 |
| WO | 2008114291 A1 | 9/2008 |
| WO | 2016154318 A1 | 9/2016 |
| WO | 2018132999 A1 | 1/2017 |
| WO | 2018171853 A1 | 9/2018 |
| WO | 2019022706 A1 | 1/2019 |
| WO | 2019204876 A1 | 4/2019 |
| WO | 2020185769 A1 | 3/2020 |
| WO | 2020075190 A1 | 4/2020 |
| WO | 2020130979 A1 | 6/2020 |
| WO | 2020149815 A2 | 7/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |
| WO | 2021038980 A1 | 3/2021 |
| WO | 2021055427 A1 | 3/2021 |
| WO | 2021055491 A1 | 3/2021 |
| WO | 2021061061 A1 | 4/2021 |
| WO | 2021081094 A1 | 4/2021 |
| WO | 2021138620 A1 | 7/2021 |
| WO | 2021216881 A1 | 10/2021 |
| WO | 2021236542 A1 | 11/2021 |
| WO | 2021236961 A1 | 11/2021 |
| WO | 2021262809 A1 | 12/2021 |
| WO | 2022216498 A1 | 10/2022 |

OTHER PUBLICATIONS

International Searching Authority, Search Report and Written Opinion for International Application No. PCT/US20/51008, dated Dec. 10, 2020, 9 pages.

International Searching Authority, Search Report and Written Opinion for International Application No. PCT/US2020/56661, dated Feb. 12, 2021, 12 pages.

International Searching Authority, Search Report and Written Opinion for International Application No. PCT/US2020/021876, dated May 28, 2020, 8 pages.

International Searching Authority, Search Report and Written Opinion for International Application No. PCT/US2021/032807, dated Sep. 6, 2021, 11 pages.

Fysiomed, "16983—Vario adjustable pedal arms", <https://www.fysiomed.com/en/products/16983-vario-adjustable-pedal-arms>, pulled from webpage on Aug. 4, 2020; 1 page.

Matrix, "R3xm Recumbent Cycle", <https://www.matrixfitness.com/en/cardio/cycles/r3xm-recumbent>, pulled from webpage on Aug. 4, 2020; 1 page.

International Searching Authority, Search Report and Written Opinion for PCT/US2020/021876, dated May 28, 2020; 8 pages.

Barrett et al., "Artificial intelligence supported patient self-care in chronic heart failure: a paradigm shift from reactive to predictive, preventive and personalised care," EPMA Journal (2019), pp. 445-464.

Derkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.

Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.

Thomas et al., "Home-Based Cardiac Rehabilitation," Circulation, 2019, pp. e69-e89, vol. 140.

Thomas et al., "Home-Based Cardiac Rehabilitation," Journal of the American College of Cardiology, Nov. 1, 2019, pp. 133-153, vol. 74.

Thomas et al., "Home-Based Cardiac Rehabilitation," HHS Public Access, Oct. 2, 2020, pp. 1-39.

Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.

Chen et al., "Home-based cardiac rehabilitation improves quality of life, aerobic capacity, and readmission rates in patients with chronic heart failure," Medicine, 2018, pp. 1-5 vol. 97:4.

LIMA de Melo Ghisi et al., "A systematic review of patient education in cardiac patients: Do they increase knowledge and promote health behavior change?," Patient Education and Counseling, 2014, pp. 1-15.

Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.

Beene et al., "AI and Care Delivery: Emerging Opportunities For Artificial Intelligence To Transform How Care Is Delivered," Nov. 2019, American Hospital Association, pp. 1-12.

Website for "Pedal Exerciser", p. 1, retrieved on Sep. 9, 2022 from https://www.vivehealth.com/collections/physical-therapy-equipment/products/pedalexerciser.

(56) References Cited

OTHER PUBLICATIONS

Website for "Functional Knee Brace with ROM", p. 1, retrieved on Sep. 9, 2022 from http://medicalbrace.gr/en/product/functional-knee-brace-with-goniometer-mbtelescopicknee/.
Website for "ComfySplints Goniometer Knee", pp. 1-5, retrieved on Sep. 9, 2022 from https://www.comfysplints.com/product/knee-splints/.
Website for "BMI FlexEze Knee Corrective Orthosis (KCO)", pp. 1-4, retrieved on Sep. 9, 2022 from https://brthobmi.com/products/bmi-flexeze%C2%AE-knee-corrective-orthosis-kco.
Website for "Neoprene Knee Brace with goniometer—Patella Rom MB.4070", pp. 1-4, retrieved on Sep. 9, 2022 from https://www.fortuna.com.gr/en/product/neoprene-knee-brace-with-goniometer-patella-rom-mb-4070/.
Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.
Ahmed et al., "Artificial intelligence with multi-functional machine learning platform development for better healthcare and precision medicine," Database, 2020, pp. 1-35.
Davenport et al., "The potential for artificial intelligence in healthcare," Digital Technology, Future Healthcare Journal, 2019, pp. 1-5, vol. 6, No. 2.
Website for "OxeFitXSI", pp. 1-3, retrieved on Sep. 9, 2022 from https://www.oxefit.com/xs1.
Website for "Preva Mobile", pp. 1-6, retrieved on Sep. 9, 2022 from https://www.precor.com/en-us/resources/introducing-preva-mobile.
Website for "J-Bike", pp. 1-3, retrieved on Sep. 9, 2022 from https://www.magneticdays.com/en/cycling-for-physical-rehabilitation.
Website for "Excy", pp. 1-12, retrieved on Sep. 9, 2022 from https://excy.com/portable-exercise-rehabilitation-excy-xcs-pro/.
Website for "OxeFit XP1", p. 1, retrieved on Sep. 9, 2022 from https://www.oxefit.com/xp1.
Davenport et al., "The Potential for Artificial Intelligence In Healthcare", 2019, Future Healthcare Journal 2019, vol. 6, No. 2: Year: 2019, pp. 1-5.
Ahmed et al., "Artificial Intelligence With Multi-Functional Machine Learning Platform Development for Better Healthcare And Precision Medicine", 2020, Database (Oxford), 2020:baaa010. doi: 10.1093/database/baaa010 (Year: 2020), pp. 1-35.
Ruiz Ivan et al., "Towards a physical rehabilitation system using a telemedicine approach", Computer Methods in Biomechanics and Biomedical Engineering: Imaging & VISUALIZATION, vol. 8, No. 6, Jul. 28, 2020, pp. 671-680, XP055914810.
De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.
Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.
Yin Chieh et al., "A Virtual Reality-Cycling Training System for Lower Limb Balance Improvement", BioMed Research International, vol. 2016, pp. 1-10.
Jennifer Bresnick, "What is the Role of Natural Language Processing in Healthcare?", pp. 1-7, published Aug. 18, 2016, retrieved on Feb. 1, 2022 from https://healthitanalytics.com/features/what-is-the-role-of-natural-language-processing-in-healthcare.
Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.
Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.
Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.

\* cited by examiner

300

```
Responsive to a first trigger condition occurring, control an electric motor to
operate in a passive mode by independently driving one or more radially-
adjustable couplings rotationally coupled to one or more pedals
302
```

↓

```
Responsive to a second trigger condition occurring, control the electric motor to
operate in an active-assisted mode by:
304
```

```
Measure revolutions per minute of the one or more radially-adjustable
couplings
306
```

```
Cause the electric motor to drive the one or more radially-adjustable
couplings rotationally coupled to the one or more pedals when the
measured revolutions per minute satisfy a threshold condition
308
```

↓

```
Responsive to a third trigger condition occurring, control the electric motor to
operate in a resistive mode by providing resistance to rotation of the one or more
radially-adjustable couplings coupled to the one or more pedals
310
```

Receive a set of angles from one or more goniometers, wherein the set of angles include at least one of angles of extension of a lower leg of a user extended away from an upper leg at a knee or angles of bend of the lower leg retracting closer toward the upper leg
502

Transmit, via one or more network interface cards, the set of angles to a computing device controlling the electromechanical device
504

FIG. 5

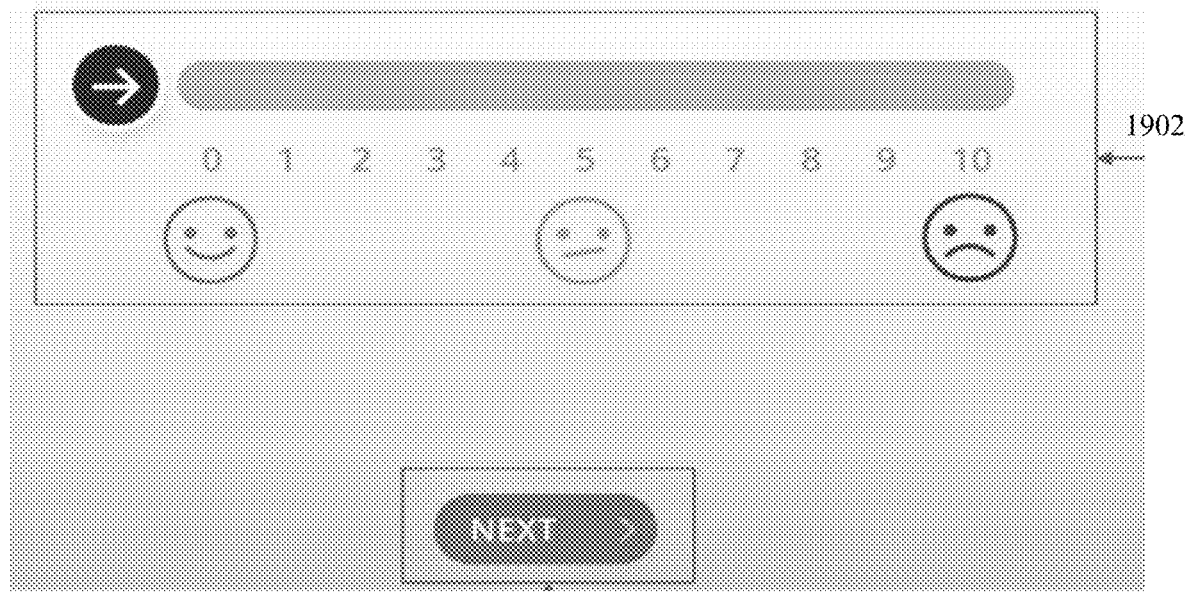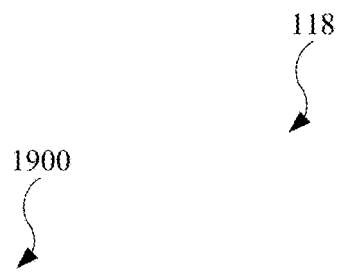
FIG. 19

CONTROL SYSTEM FOR A REHABILITATION AND EXERCISE ELECTROMECHANICAL DEVICE

CROSS-REFERENCE TO RELATED APPLICATIONS

This application claims priority to and the benefit of U.S. Provisional Application Patent Ser. No. 62/816,503, filed Mar. 11, 2019, the entire disclosure of which is hereby incorporated by reference.

TECHNICAL FIELD

This disclosure relates generally to electromechanical devices. More specifically, this disclosure relates to a control system for a rehabilitation and exercise electromechanical device.

BACKGROUND

Various devices may be used by people for exercising and/or rehabilitating parts of their bodies. For example, to maintain a desired level of fitness, users may operate devices for a period of time or distance as part of a workout regime. In another example, a person may undergo knee surgery and a physician may provide a treatment plan for rehabilitation that includes operating a rehabilitation device for a period of time and/or distance periodically to strengthen and/or improve flexibility of the knee. The exercise and/or rehabilitation devices may include pedals on opposite sides. The devices may be operated by a user engaging the pedals with their feet or their hands and rotating the pedals.

SUMMARY

In general, the present disclosure provides a control system for an adjustable rehabilitation and exercise device and associated components.

In one aspect, an electromechanical device for rehabilitation includes one or more pedals coupled to one or more radially-adjustable couplings, an electric motor coupled to the one or more pedals via the one or more radially-adjustable couplings, and a control system including one or more processing devices operatively coupled to the electric motor. The one or more processing devices may be configured to, responsive to a first trigger condition occurring, control the electric motor to operate in a passive mode by independently driving the one or more radially-adjustable couplings rotationally coupled to the one or more pedals. The one or more processing devices may also be configured to, responsive to a second trigger condition occurring, control the electric motor to operate in an active-assisted mode by (1) measuring revolutions per minute of the one or more radially-adjustable couplings, and (2) causing the electric motor to drive the one or more radially-adjustable couplings rotationally coupled to the one or more pedals when the measured revolutions per minute satisfy a threshold condition. The one or more processing devices may also be configured to, responsive to a third trigger condition occurring, control the electric motor to operate in a resistive mode by providing resistance to rotation of the one or more radially-adjustable couplings coupled to the one or more pedals.

In another aspect, a method for controlling, via a processing device, an electromechanical device may include receiving configuration information for a pedaling session, setting a resistance parameter and a maximum pedal force parameter based on the configuration information for the pedaling session, and measuring force applied to pedals of the electromechanical device as a user pedals the electromechanical device. An electric motor of the electromechanical device may provide resistance during the pedaling session based on the resistance parameter. The method may also include determining whether the measured force exceeds the maximum pedal force parameter, and responsive to determining that the measured force exceeds the maximum pedal force parameter, reducing the resistance parameter so the electric motor applies less resistance during the pedaling session to maintain a revolutions per minute threshold.

In yet another aspect, an electronic device, may include one or more memory devices storing instructions, one or more network interface cards, one or more goniometers, and one or more processing devices operatively coupled to the one or more memory devices, the one or more network interface cards, and the one or more goniometers. The one or more processing devices execute the instructions to receive a set of angles from the one or more goniometers. The set of angles may include at least one of angles of extension of a lower leg of a user extended away from an upper leg at a knee or angles of bend of the lower leg retracting closer toward the upper leg. The one or more processing devices may transmit, via the one or more network interface cards, the set of angles to a computing device controlling an electromechanical device.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), solid state drive (SSD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of this disclosure and its advantages, reference is now made to the following description, taken in conjunction with the accompanying drawings, in which:

FIG. 3 illustrates example operations of a method for controlling an electromechanical device for rehabilitation in various modes according to certain embodiments of this disclosure;

FIG. 5 illustrates example operations of a method for measuring angles of bend and/or extension of a lower leg relative to an upper leg using a goniometer according to certain embodiments of this disclosure;

FIG. 19 illustrates an example user interface of the user portal, the user interface presenting a scale for measuring pain of the user at an end of a pedaling session according to certain embodiments of this disclosure;

DETAILED DESCRIPTION

Figure 1:
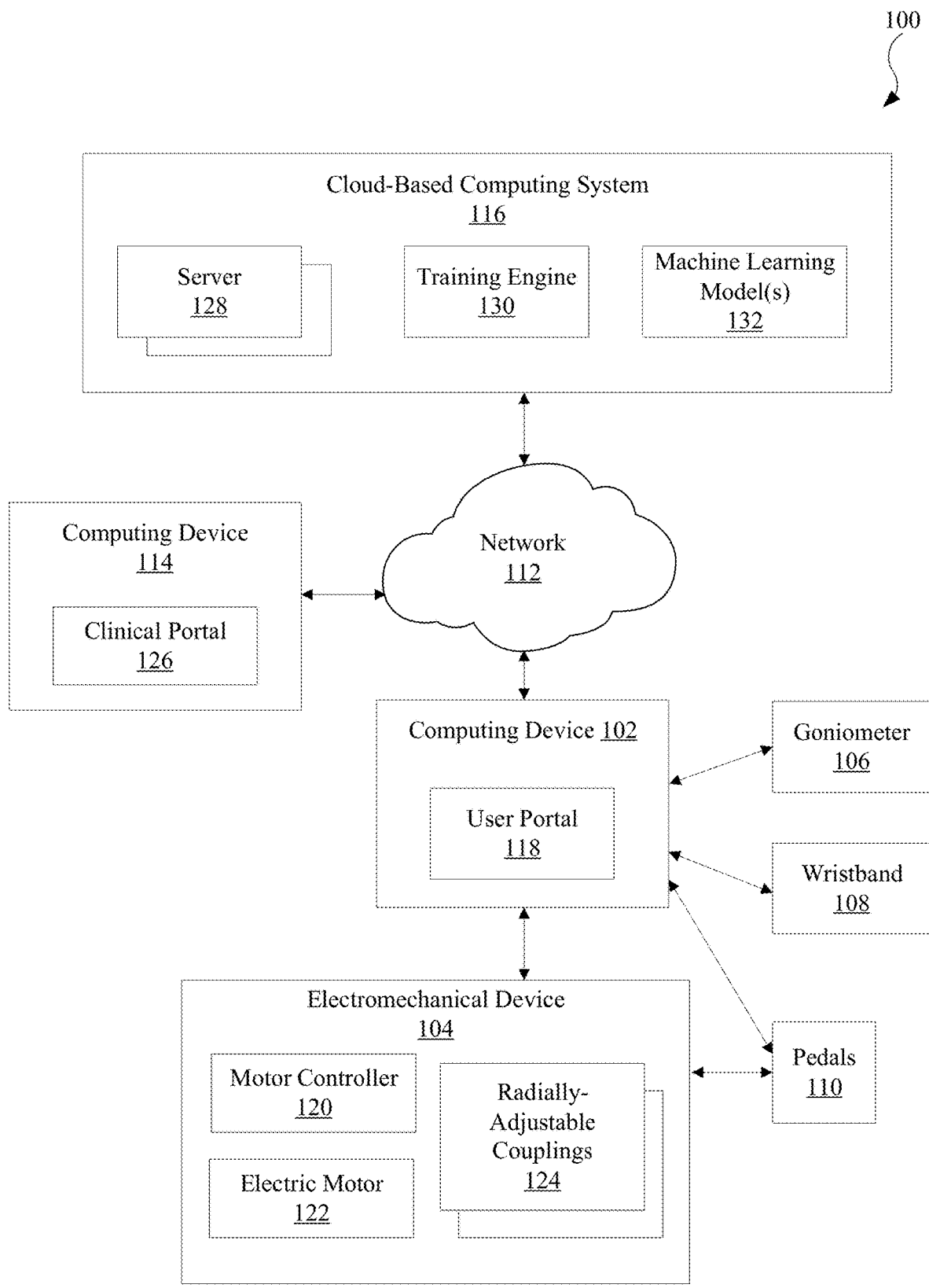
FIG. 1 illustrates a high-level component diagram of an illustrative rehabilitation system architecture according to certain embodiments of this disclosure.

Improvement is desired in the field of devices used for rehabilitation and exercise. People may injure, sprain, or tear a body part and consult a physician to diagnose the injury. In some instances, the physician may prescribe a treatment plan that includes operating one or more electromechanical devices (e.g., pedaling devices for arms or legs) for a period of time to exercise the affected area in an attempt to rehabilitate the affected body part and regain normal movability. In other instances, the person with the affected body part may determine to operate a device without consulting a physician. In either scenario, the devices that are operated lack effective monitoring of progress of rehabilitation of the affected area and control over the electromechanical device during operation by the user. Conventional devices lack components that enable operating the electromechanical device in various modes that are designed to enhance the rate and effectiveness of rehabilitation. Further, conventional rehabilitation systems lack monitoring devices that aid in determining one or more properties of the user (e.g., range of motion of the affected area, heartrate of the user, etc.) and enable adjusting components based on the determined properties. When the user is supposed to be adhering to a treatment plan, conventional rehabilitation systems may not provide real-time results of sessions to the physicians. That is, typically the physicians have to rely on the patient's word as to whether they are adhering to the treatment plan. As a result of the abovementioned issues, conventional rehabilitation systems that use electromechanical devices may not provide effective and/or efficient rehabilitation of the affected body part.

Accordingly, aspects of the present disclosure generally relate to a control system for a rehabilitation and exercise electromechanical device (referred to herein as "electromechanical device"). The electromechanical device may include an electric motor configured to drive one or more radially-adjustable couplings to rotationally move pedals coupled to the radially-adjustable couplings. The electromechanical device may be operated by a user engaging the pedals with their hands or their feet and rotating the pedals to exercise and/or rehabilitate a desired body part. The electromechanical device and the control system may be included as part of a larger rehabilitation system. The rehabilitation system may also include monitoring devices (e.g., goniometer, wristband, force sensors in the pedals, etc.) that provide valuable information about the user to the control system. As such, the monitoring devices may be in direct or indirect communication with the control system.

The monitoring devices may include a goniometer that is configured to measure range of motion (e.g., angles of extension and/or bend) of a body part to which the goniometer is attached. The measured range of motion may be presented to the user and/or a physician via a user portal and/or a clinical portal. Also the control system may use the measured range of motion to determine whether to adjust positions of the pedals on the radially-adjustable couplings and/or to adjust the mode types (e.g., passive, active-assisted, resistive, active) and/or durations to operate the electromechanical device during a treatment plan. The monitoring devices may also include a wristband configured to track the steps of the user over a time period (e.g., day, week, etc.) and/or measure vital signs of the user (e.g., heartrate, blood pressure, oxygen level). The monitoring devices may also include force sensors disposed in the pedals that are configured to measure the force exerted by the user on the pedals.

The control system may enable operating the electromechanical device in a variety of modes, such as a passive mode, an active-assisted mode, a resistive mode, and/or an active mode. The control system may use the information received from the measuring devices to adjust parameters (e.g., reduce resistance provided by electric motor, increase resistance provided by the electric motor, increase/decrease speed of the electric motor, adjust position of pedals on radially-adjustable couplings, etc.) while operating the electromechanical device in the various modes. The control system may receive the information from the monitoring devices, aggregate the information, make determinations using the information, and/or transmit the information to a cloud-based computing system for storage. The cloud-based computing system may maintain the information that is related to each user.

A clinician and/or a machine learning model may generate a treatment plan for a user to rehabilitate a part of their body using at least the electromechanical device. A treatment plan may include a set of pedaling sessions using the electromechanical device, a set of joint extension sessions, a set of flex sessions, a set of walking sessions, a set of heartrates per pedaling session and/or walking session, and the like.

Each pedaling session may specify that a user is to operate the electromechanical device in a combination of one or more modes, including: passive, active-passive, active, and resistive. The pedaling session may specify that the user is to wear the wristband and the goniometer during the pedaling session. Further, each pedaling session may include a set amount of time that the electromechanical device is to operate in each mode, a target heartrate for the user during each mode in the pedaling session, target forces that the user is to exert on the pedals during each mode in the pedaling session, target ranges of motion the body parts are to attain during the pedaling session, positions of the pedals on the radially-adjustable couplings, and the like.

Each joint extension session may specify a target angle of extension at the joint, and each set of joint flex sessions may specify a target angle of flex at the joint. Each walking session may specify a target number of steps the user should take over a set period of time (e.g., day, week etc.) and/or a target heartrate to achieve and/or maintain during the walking session.

The treatment plans may be stored in the cloud-based computing system and downloaded to the computing device of the user when the user is ready to begin the treatment plan. In some embodiments, the computing device that executes a clinical portal may transmit the treatment plan to the computing device that executes a user portal and the user may initiate the treatment plan when ready.

In addition, the disclosed rehabilitation system may enable a physician to monitor the progress of the user in real-time using the clinical portal. The clinical portal may present information pertaining to when the user is engaged in one or more sessions, statistics (e.g., speed, revolutions per minute, position of pedals, force on the pedals, vital signs, number of steps taken by user, range of motion, etc.)

of the sessions, and the like. The clinical portal may also enable the physician to view before and after session images of the affected body part of the user to enable the physician to judge how well the treatment plan is working and/or to make adjustments to the treatment plan. The clinical portal may enable the physician to dynamically change a parameter (e.g., position of pedals, amount of resistance provided by electric motor, speed of the electric motor, duration of one of the modes, etc.) of the treatment plan in real-time based on information received from the control system.

The disclosed techniques provide numerous benefits over conventional systems. For example, the rehabilitation system provides granular control over the components of the electromechanical device to enhance the efficiency and effectiveness of rehabilitation of the user. The control system enables operating the electromechanical device in any suitable combination of the modes described herein by controlling the electric motor. Further, the control system may use information received from the monitoring devices to adjust parameters of components of the electromechanical device in real-time during a pedaling session, for example. Additional benefits of this disclosure may include enabling a computing device operated by a physician to monitor the progress of a user participating in a treatment plan in real-time and/or to control operation of the electromechanical device during a pedaling session.

FIGS. 1 through 31, discussed below, and the various embodiments used to describe the principles of this disclosure are by way of illustration only and should not be construed in any way to limit the scope of the disclosure.

FIG. 1 illustrates a high-level component diagram of an illustrative rehabilitation system architecture 100 according to certain embodiments of this disclosure. In some embodiments, the system architecture 100 may include a computing device 102 communicatively coupled to an electromechanical device 104, a goniometer 106, a wristband 108, and/or pedals 110 of the electromechanical device 104. Each of the computing device 102, the electromechanical device 104, the goniometer 106, the wristband 108, and the pedals 110 may include one or more processing devices, memory devices, and network interface cards. The network interface cards may enable communication via a wireless protocol for transmitting data over short distances, such as Bluetooth, ZigBee, etc. In some embodiments, the computing device 102 is communicatively coupled to the electromechanical device 104, goniometer 106, the wristband 108, and/or the pedals 110 via Bluetooth.

Additionally, the network interface cards may enable communicating data over long distances, and in one example, the computing device 102 may communicate with a network 112. Network 112 may be a public network (e.g., connected to the Internet via wired (Ethernet) or wireless (WiFi)), a private network (e.g., a local area network (LAN) or wide area network (WAN)), or a combination thereof. The computing device 102 may be communicatively coupled with a computing device 114 and a cloud-based computing system 116.

The computing device 102 may be any suitable computing device, such as a laptop, tablet, smartphone, or computer. The computing device 102 may include a display that is capable of presenting a user interface, such as a user portal 118. The user portal 118 may be implemented in computer instructions stored on the one or more memory devices of the computing device 102 and executable by the one or more processing devices of the computing device 102. The user portal 118 may present various screens to a user that enable the user to view a treatment plan, initiate a pedaling session of the treatment plan, control parameters of the electromechanical device 104, view progress of rehabilitation during the pedaling session, and so forth as described in more detail below. The computing device 102 may also include instructions stored on the one or more memory devices that, when executed by the one or more processing devices of the computing device 102, perform operations to control the electromechanical device 104.

The computing device 114 may execute a clinical portal 126. The clinical portal 126 may be implemented in computer instructions stored on the one or more memory devices of the computing device 114 and executable by the one or more processing devices of the computing device 114. The clinical portal 114 may present various screens to a physician that enable the physician to create a treatment plan for a patient, view progress of the user throughout the treatment plan, view measured properties (e.g., angles of bend/extension, force exerted on pedals 110, heartrate, steps taken, images of the affected body part) of the user during sessions of the treatment plan, view properties (e.g., modes completed, revolutions per minute, etc.) of the electromechanical device 104 during sessions of the treatment plan. The treatment plan specific to a patient may be transmitted via the network 112 to the cloud-based computing system 116 for storage and/or to the computing device 102 so the patient may begin the treatment plan.

The electromechanical device 104 may be an adjustable pedaling device for exercising and rehabilitating arms and/or legs of a user. The electromechanical device 104 may include at least one or more motor controllers 120, one or more electric motors 122, and one or more radially-adjustable couplings 124. Two pedals 110 may be coupled to two radially-adjustable couplings 124 via a left and right pedal assemblies that each include a respective stepper motor. The motor controller 120 may be operatively coupled to the electric motor 122 and configured to provide commands to the electric motor 122 to control operation of the electric motor 122. The motor controller 120 may include any suitable microcontroller including a circuit board having one or more processing devices, one or more memory devices (e.g., read-only memory (ROM) and/or random access memory (RAM)), one or more network interface cards, and/or programmable input/output peripherals. The motor controller 120 may provide control signals or commands to drive the electric motor 122. The electric motor 122 may be powered to drive one or more radially-adjustable couplings 124 of the electromechanical device 104 in a rotational manner. The electric motor 122 may provide the driving force to rotate the radially-adjustable couplings 124 at configurable speeds. The couplings 124 are radially-adjustable in that a pedal 110 attached to the coupling 124 may be adjusted to a number of positions on the coupling 125 in a radial fashion. Further, the electromechanical device 104 may include current shunt to provide resistance to dissipate energy from the electric motor 122. As such, the electric motor 122 may be configured to provide resistance to rotation of the radially-adjustable couplings 124.

The computing device 102 may be communicatively connected to the electromechanical device 104 via the network interface card on the motor controller 120. The computing device 102 may transmit commands to the motor controller 120 to control the electric motor 122. The network interface card of the motor controller 120 may receive the commands and transmit the commands to the electric motor 122 to drive the electric motor 122. In this way, the computing device 102 is operatively coupled to the electric motor 122.

The computing device 102 and/or the motor controller 120 may be referred to as a control system herein. The user portal 118 may be referred to as a user interface of the control system herein. The control system may control the electric motor 122 to operate in a number of modes: passive, active-assisted, resistive, and active. The passive mode may refer to the electric motor 122 independently driving the one or more radially-adjustable couplings 124 rotationally coupled to the one or more pedals 110. In the passive mode, the electric motor 122 may be the only source of driving force on the radially-adjustable couplings. That is, the user may engage the pedals 110 with their hands or their feet and the electric motor 122 may rotate the radially-adjustable couplings 124 for the user. This may enable moving the affected body part and stretching the affected body part without the user exerting excessive force.

The active-assisted mode may refer to the electric motor 122 receiving measurements of revolutions per minute of the one or more radially-adjustable couplings 124, and causing the electric motor 122 to drive the one or more radially-adjustable couplings 124 rotationally coupled to the one or more pedals 110 when the measured revolutions per minute satisfy a threshold condition. The threshold condition may be configurable by the user and/or the physician. The electric motor 122 may be powered off while the user provides the driving force to the radially-adjustable couplings 124 as long as the revolutions per minute are above a revolutions per minute threshold and the threshold condition is not satisfied. When the revolutions per minute are less than the revolutions per minute threshold then the threshold condition is satisfied and the electric motor 122 may be controlled to drive the radially-adjustable couplings 124 to maintain the revolutions per minute threshold.

The resistive mode may refer to the electric motor 122 providing resistance to rotation of the one or more radially-adjustable couplings 124 coupled to the one or more pedals 110. The resistive mode may increase the strength of the body part being rehabilitated by causing the muscle to exert force to move the pedals against the resistance provided by the electric motor 122.

The active mode may refer to the electric motor 122 powering off to provide no driving force assistance to the radially-adjustable couplings 124. Instead, in this mode, the user provides the sole driving force of the radially-adjustable couplings using their hands or feet, for example.

During one or more of the modes, each of the pedals 110 may measure force exerted by a part of the body of the user on the pedal 110. For example, the pedals 110 may each contain any suitable sensor (e.g., strain gauge load cell, piezoelectric crystal, hydraulic load cell, etc.) for measuring force exerted on the pedal 110. Further, the pedals 110 may each contain any suitable sensor for detecting whether the body part of the user separates from contact with the pedals 110. In some embodiments, the measured force may be used to detect whether the body part has separated from the pedals 11. The force detected may be transmitted via the network interface card of the pedal 110 to the control system (e.g., computing device 102 and/or motor controller 120). As described further below, the control system may modify a parameter of operating the electric motor 122 based on the measured force. Further, the control system may perform one or more preventative action (e.g., locking the electric motor 120 to stop the radially-adjustable couplings 124 from moving, slowing down the electric motor 122, presenting a notification to the user, etc.) when the body part is detected as separated from the pedals 110, among other things.

The goniometer 106 may be configured to measure angles of extension and/or bend of body parts and transmit the measured angles to the computing device 102 and/or the computing device 114. The goniometer 106 may be included in an electronic device that includes the one or more processing devices, memory devices, and/or network interface cards. The goniometer 106 may be disposed in a cavity of a mechanical brace. The cavity of the mechanical brace may be located near a center of the mechanical brace where the mechanical brace affords to bend and extend. The mechanical brace may be configured to secure to an upper body part (e.g., leg, arm, etc.) and a lower body part (e.g., leg, arm, etc.) to measure the angles of bend as the body parts are extended away from one another or retracted closer to one another.

The wristband 108 may include a 3-axis accelerometer to track motion in the X, Y, and Z directions, an altimeter for measuring altitude, and/or a gyroscope to measure orientation and rotation. The accelerometer, altimeter, and/or gyroscope may be operatively coupled to a processing device in the wristband 108 and may transmit data to the processing device. The processing device may cause a network interface card to transmit the data to the computing device 102 and the computing device 102 may use the data representing acceleration, frequency, duration, intensity, and patterns of movement to track steps taken by the user over certain time periods (e.g., days, weeks, etc.). The computing device 102 may transmit the steps to the computing device 114 executing a clinical portal 126. Additionally, in some embodiments, the processing device of the wristband 108 may determine the steps taken and transmit the steps to the computing device 102. In some embodiments, the wristband 108 may use photoplethysmography (PPG) to measure heartrate that detects an amount of red light or green light on the skin of the wrist. For example, blood may absorb green light so when the heart beats, the blood flow may absorb more green light, thereby enabling detecting heartrate. The heartrate may be sent to the computing device 102 and/or the computing device 114.

The computing device 102 may present the steps taken by the user and/or the heartrate via respective graphical element on the user portal 118, as discussed further below. The computing device may also use the steps taken and/or the heart rate to control a parameter of operating the electro-mechanical device 104. For example, if the heartrate exceeds a target heartrate for a pedaling session, the computing device 102 may control the electric motor 122 to reduce resistance being applied to rotation of the radially-adjustable couplings 124. In another example, if the steps taken are below a step threshold for a day, the treatment plan may increase the amount of time for one or more modes that the user in which the user is to operate the electromechanical device 104 to ensure the affected body part is getting sufficient movement.

In some embodiments, the cloud-based computing system 116 may include one or more servers 128 that form a distributed computing architecture. Each of the servers 128 may include one or more processing devices, memory devices, data storage, and/or network interface cards. The servers 128 may be in communication with one another via any suitable communication protocol. The servers 128 may store profiles for each of the users that use the electromechanical device 104. The profiles may include information about the users such as a treatment plan, the affected body part, any procedure the user had performed on the affected body part, health, age, race, measured data from the goniometer 106, measured data from the wristband 108, measured data from the pedals 110, user input received at the user portal 118 during operation of any of the modes of the treatment plan, a level of discomfort the user experiences before and after any of the modes, before and after session images of the affected body part, and so forth.

In some embodiments the cloud-based computing system 116 may include a training engine 130 that is capable of generating one or more machine learning models 132. The machine learning models 132 may be trained to generate treatment plans for the patients in response to receiving various inputs (e.g., a procedure performed on the patient, an affected body part the procedure was performed on, other health characteristics (age, race, fitness level, etc.). The one or more machine learning models 132 may be generated by the training engine 130 and may be implemented in computer instructions that are executable by one or more processing device of the training engine 130 and/or the servers 128. To generate the one or more machine learning models 132, the training engine 130 may train the one or more machine learning models 132. The training engine 130 may use a base data set of patient characteristics, treatment plans followed by the patient, and results of the treatment plan followed by the patients. The results may include information indicating whether the treatment plan led to full recovery of the affected body part, partial recover of the affect body part, or lack of recovery of the affected body part. The training engine 130 may be a rackmount server, a router computer, a personal computer, a portable digital assistant, a smartphone, a laptop computer, a tablet computer, a camera, a video camera, a netbook, a desktop computer, a media center, or any combination of the above. The one or more machine learning models 132 may refer to model artifacts that are created by the training engine 130 using training data that includes training inputs and corresponding target outputs. The training engine 130 may find patterns in the training data that map the training input to the target output, and generate the machine learning models 132 that capture these patterns. Although depicted separately from the computing device 102, in some embodiments, the training engine 130 and/or the machine learning models 132 may reside on the computing device 102 and/or the computing device 114.

The machine learning models 132 may include one or more of a neural network, such as an image classifier, recurrent neural network, convolutional network, generative adversarial network, a fully connected neural network, or some combination thereof, for example. In some embodiments, the machine learning models 106 may be composed of a single level of linear or non-linear operations or may include multiple levels of non-linear operations. For example, the machine learning model may include numerous layers and/or hidden layers that perform calculations (e.g., dot products) using various neurons.

Figure 2:
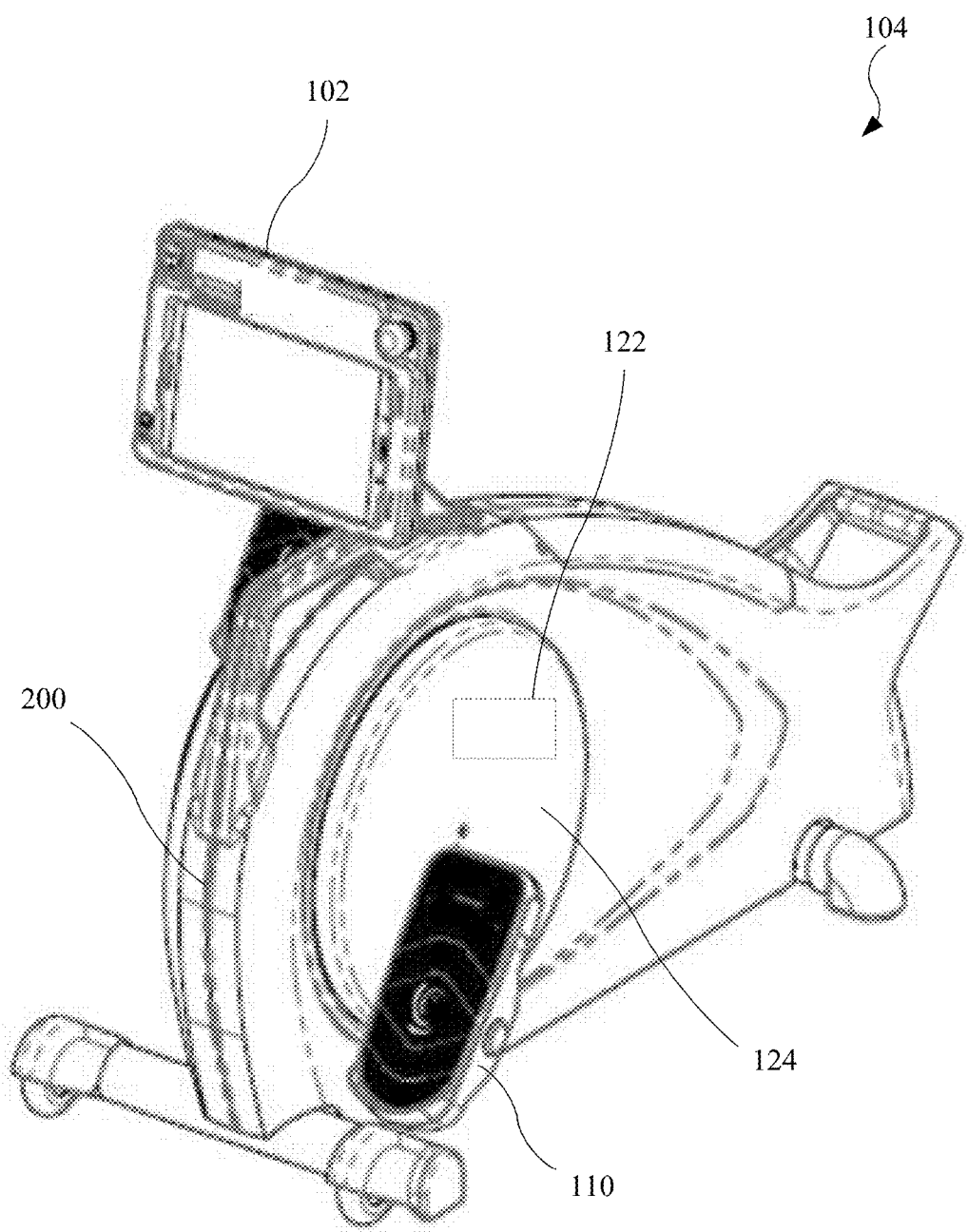
FIG. 2 illustrates a perspective view of an example of an exercise and rehabilitation device according to certain embodiments of this disclosure.

FIG. 2 illustrates a perspective view of an example of an exercise and rehabilitation device 104 according to certain embodiments of this disclosure. The electromechanical device 104 is shown having pedal 110 on opposite sides that are adjustably positionable relative to one another on respective radially-adjustable couplings 124. The depicted device 104 is configured as a small and portable unit so that it is easily transported to different locations at which rehabilitation or treatment is to be provided, such as at patients' homes, alternative care facilities, or the like. The patient may sit in a chair proximate the device 104 to engage the device 104 with their feet, for example.

The device 104 includes a rotary device such as radially-adjustable couplings 124 or flywheel or the like rotatably mounted such as by a central hub to a frame 16 or other support. The pedals 110 are configured for interacting with a patient to be rehabilitated and may be configured for use with lower body extremities such as the feet, legs, or upper body extremities, such as the hands, arms, and the like. For example, the pedal 110 may be a bicycle pedal of the type having a foot support rotatably mounted onto an axle with bearings. The axle may or may not have exposed end threads for engaging a mount on the radially-adjustable coupling 124 to locate the pedal on the radially-adjustable coupling 124. The radially-adjustable coupling 124 may include an actuator configured to radially adjust the location of the pedal to various positions on the radially-adjustable coupling 124.

The radially-adjustable coupling 124 may be configured to have both pedals 110 on opposite sides of a single coupling 124. In some embodiments, as depicted, a pair of radially-adjustable couplings 124 may be spaced apart from one another but interconnected to the electric motor 122. In the depicted example, the computing device 102 may be mounted on the frame 200 and may be detachable and held by the user while the user operates the device 104. The computing device 102 may present the user portal and control the operation of the electric motor 122, as described herein.

In some embodiments, as described in U.S. Pat. No. 10,173,094 B2, which is incorporated by reference herein in its entirety for all purposes, the electromechanical device 104 may take the form of a traditional exercise/rehabilitation device which is more or less non-portable and remains in a fixed location (e.g., such as a rehabilitation clinic or medical practice). The device 104 may include a seat and be less portable than the device 104 shown in FIG. 2.

FIG. 3 illustrates example operations of a method 300 for controlling an electromechanical device for rehabilitation in various modes according to certain embodiments of this disclosure. The method 300 may be performed by processing logic that may include hardware (circuitry, dedicated logic, etc.), firmware, software, or a combination of both. The method 300 and/or each of their individual functions, subroutines, or operations may be performed by one or more processors of a control system (e.g., computing device 102 of FIG. 1) implementing the method 300. The method 300 may be implemented as computer instructions that, when executed by a processing device, execute the user portal 118. In certain implementations, the method 300 may be performed by a single processing thread. Alternatively, the method 300 may be performed by two or more processing threads, each thread implementing one or more individual functions, routines, subroutines, or operations of the methods. Various operations of the method 300 may be performed by one or more of the cloud-based computing system 116, the motor controller 120, the pedals 110, the goniometer 106, the wristband 108, and/or the computing device 114 of FIG. 1.

As discussed above, an electromechanical device may include one or more pedals coupled to one or more radially-adjustable couplings, an electric motor coupled to the one or more pedals via the one or more radially-adjustable couplings, and the control system including one or more processing devices operatively coupled to the electric motor. In some embodiments, the control system (e.g., computing device 102 and/or motor controller 120) may store instructions and one or more operations of the control system may be presented via the user portal. In some embodiments the radially-adjustable couplings are configured for translating rotational motion of the electric motor to radial motion of the pedals.

At block 302, responsive to a first trigger condition occurring, the processing device may control the electric motor to operate in a passive mode by independently driving the one or more radially-adjustable couplings rotationally coupled to the one or more pedals. "Independently drive" may refer to the electric motor driving the one or more radially-adjustable couplings without the aid of another driving source (e.g., the user). The first trigger condition may include an initiation of a pedaling session via the user interface of the control system, a period of time elapsing, a detected physical condition (e.g., heartrate, oxygen level, blood pressure, etc.) of a user operating the electromechanical device, a request received from the user via the user interface, or a request received via a computing device communicatively coupled to the control system (e.g., a request received from the computing device executing the clinical portal). The processing device may control the electric motor to independently drive the one or more radially-adjustable couplings rotationally coupled to the one or more pedals at a controlled speed specified in a treatment plan for a user operating the electromechanical device while operating in the passive mode.

In some embodiments, the electromechanical device may be configured such that the processor controls the electric motor to individually drive the radially-adjustable couplings. For example, the processing device may control the electric motor to individually drive the left or right radially-adjustable coupling, while allowing the user to provide the force to drive the other radially-adjustable coupling. As another example, the processing device may control the electric motor to drive both the left and right radially-adjustable couplings but at different speeds. This granularity of control may be beneficial by controlling the speed at which a healing body part is moved (e.g., rotated, flexed, extended, etc.) to avoid tearing tendons or causing pain to the user.

At block 304, responsive to a second trigger condition occurring, the processing device may control the electric motor to operate in an active-assisted mode by measuring (block 306) revolutions per minute of the one or more radially-adjustable couplings, and causing (block 308) the electric motor to drive the one or more radially-adjustable couplings rotationally coupled to the one or more pedals when the measured revolutions per minute satisfy a threshold condition. The second trigger condition may include an initiation of a pedaling session via the user interface of the control system, a period of time elapsing, a detected physical condition (e.g., heartrate, oxygen level, blood pressure, etc.) of a user operating the electromechanical device, a request received from the user via the user interface, or a request received via a computing device communicatively coupled to the control system (e.g., a request received from the computing device executing the clinical portal). The threshold condition may be satisfied when the measured revolutions per minute are less than a minimum revolutions per minute. In such an instance, the electric motor may begin driving the one or more radially-adjustable couplings to increase the revolutions per minute of the radially-adjustable couplings.

As with the passive mode, the processing device may control the electric motor to individually drive the one or more radially-adjustable couplings in the active-assisted mode. For example, if just a right knee is being rehabilitated, the revolutions per minute of the right radially-adjustable coupling may be measured and the processing device may control the electric motor to individually drive the right radially-adjustable coupling when the measured revolutions per minute is less than the minimum revolutions per minute. In some embodiments, there may be different minimum revolution per minutes set for the left radially-adjustable coupling and the right radially-adjustable coupling, and the processing device may control the electric motor to individually drive the left radially-adjustable coupling and the right radially-adjustable coupling as appropriate to maintain the different minimum revolutions per minute.

At block 310, responsive to a third trigger condition occurring, the processing device may control the electric motor to operate in a resistive mode by providing resistance to rotation of the one or more radially-adjustable couplings coupled to the one or more pedals. The third trigger condition may include an initiation of a pedaling session via the user interface of the control system, a period of time elapsing, a detected physical condition (e.g., heartrate, oxygen level, blood pressure, etc.) of a user operating the electromechanical device, a request received from the user via the user interface, or a request received via a computing device communicatively coupled to the control system (e.g., a request received from the computing device executing the clinical portal).

In some embodiments, responsive to a fourth trigger condition occurring, the processing device is further configured to control the electric motor to operate in an active mode by powering off to enable another source (e.g., the user) to drive the one or more radially-adjustable couplings via the one or more pedals. In the active mode, the another source may drive the one or more radially-adjustable couplings via the one or more pedals at any desired speed.

In some embodiments, the processing device may control the electric motor to operate in each of the passive mode, the active-assisted mode, the resistive mode, and/or the active mode for a respective period of time during a pedaling session based on a treatment plan for a user operating the electromechanical device. In some embodiments, the various modes and the respective periods of time may be selected by a clinician that sets up the treatment plan using the clinical portal. In some embodiments, the various modes and the respective periods of time may be selected by a machine learning model trained to receive parameters (e.g., procedure performed on the user, body part on which the procedure was performed, health of the user) and to output a treatment plan to rehabilitate the affected body part, as described above.

In some embodiments, the processing device may modify one or more positions of the one or more pedals on the one or more radially-adjustable couplings to change one or more diameters of ranges of motion of the one or more pedals during any of the passive mode, active-assisted mode, the resistive mode, and/or the active mode throughout a pedaling session for a user operating the electromechanical device. The processing device may be further configured to modify the position of one of the one or more pedals on one of the one or more radially-adjustable couplings to change the diameter of the range of motion of the one of the one or more pedals while maintaining another position of another of the one or more pedals on another of the one or more radially-adjustable couplings to maintain another diameter of another range of motion of the another pedal. In some embodiments, the processing device may cause both positions of the pedals to move to change the diameter of the range of motion for both pedals. The amount of movement of the positions of the pedals may be individually controlled in order to provide different diameters of ranges of motions of the pedals as desired.

In some embodiments, the processing device may receive, from the goniometer worn by the user operating the electromechanical device, at least one of an angle of extension of a joint of the user during a pedaling session or an angle of bend of the joint of the user during the pedaling session. In some instances, the joint may be a knee or an elbow. The goniometer may be measuring the angles of bend and/or extension of the joint and continuously or periodically transmitting the angle measurements that are received by the processing device. The processing device may modify the positions of the pedals on the radially-adjustable couplings to change the diameters of the ranges of motion of the pedals based on the at least one of the angle of extension of the joint of the user or the angle of bend of the joint of the user.

In some embodiments, the processing device may receive, from the goniometer worn by the user, a set of angles of extension between an upper leg and a lower leg at a knee of the user as the user extends the lower leg away from the upper leg via the knee. In some embodiments, the goniometer may send the set of angles of extension between an upper arm, upper body, etc. and a lower arm, lower body, etc. The processing device may present, on a user interface of the control system, a graphical animation of the upper leg, the lower leg, and the knee of the user as the lower leg is extended away from the upper leg via the knee. The graphical animation may include the set of angles of extension as the set of angles of extension change during the extension. The processing device may store, in a data store of the control system, a lowest value of the set of angles of extension as an extension statistic for an extension session. A set of extension statistics may be stored for a set of extension sessions specified by the treatment plan. The processing device may present progress of the set of extension sessions throughout the treatment plan via a graphical element (e.g., line graph, bar chart, etc.) on the user interface presenting the set of extension statistics.

In some embodiments, the processing device may receive, from the goniometer worn by the user, a set of angles of bend or flex between an upper leg and a lower leg at a knee of the user as the user retracts the lower leg closer to the upper leg via the knee. In some embodiments, the goniometer may send the set of angles of bend between an upper arm, upper body, etc. and a lower arm, lower body, etc. The processing device may present, on a user interface of the control system, a graphical animation of the upper leg, the lower leg, and the knee of the user as the lower leg is retracted closer to the upper leg via the knee. The graphical animation may include the set of angles of bend as the set of angles of bend change during the bending. The processing device may store, in a data store of the control system, a highest value of the set of angles of bend as a bend statistic for a bend session. A set of bend statistics may be stored for a set of bend sessions specified by the treatment plan. The processing device may present progress of the set of bend sessions throughout the treatment plan via a graphical element (e.g., line graph, bar chart, etc.) on the user interface presenting the set of bend statistics.

In some embodiments, the angles of extension and/or bend of the joint may be transmitted by the goniometer to a computing device executing a clinical portal. A clinician may be operating the computing device executing the clinical portal. The clinical portal may present a graphical animation of the upper leg extending away from the lower leg and/or the upper leg bending closer to the lower leg in real-time during a pedaling session, extension session, and/or a bend session of the user. In some embodiments, the clinician may provide notifications to the computing device to present via the user portal. The notifications may indicate that the user has satisfied a target extension and/or bend angle. Other notifications may indicate that the user has extended or retracted a body part too far and should cease the extension and/or bend session. In some embodiments, the computing device executing the clinical portal may transmit a control signal to the control system to move a position of a pedal on the radially-adjustable coupling based on the angle of extension or angle of bend received from the goniometer. That is, the clinician can increase a diameter of range of motion for a body part of the user in real-time based on the measured angles of extension and/or bend during a pedaling session. This may enable the clinician dynamically control the pedaling session to enhance the rehabilitation results of the pedaling session.

In some embodiments, the processing device may receive, from a wearable device (e.g., wristband), an amount of steps taken by a user over a certain time period (e.g., day, week, etc.). The processing device may calculate whether the amount of steps satisfies a step threshold of a walking session of a treatment plan for the user. The processing device may present the amount of steps taken by the user on a user interface of the control system and may present an indication of whether the amount of steps satisfies the step threshold.

The wristband may also measure one or more vital statistics of the user, such as a heartrate, oxygen level, blood pressure, and the like. The measurements of the vital statistics may be performed at any suitable time, such as during a pedaling session, walking session, extension session, and/or bend session. The wristband may transmit the one or more vital statistics to the control system. The processing device of the control system may use the vital statistics to determine whether to reduce resistance the electric motor is providing to lower one of the vital statistics (e.g., heartrate) when that vital statistic is above a threshold, to determine whether the user is in pain when one of the vital statistics is elevated beyond a threshold, to determine whether to provide a notification indicating the user should take a break or increase the intensity of the appropriate session, and so forth.

In some embodiments, the processing device may receive a request to stop the one or more pedals from moving. The request may be received by a user selecting a graphical icon representing "stop" on the user portal of the control system. The processing device may cause the electric motor to lock and stop the one or more pedals from moving over a configured period of time (e.g., instantly, over 1 second, 2 seconds, 3 seconds, 5 seconds, 10 seconds, etc.). One benefit of including an electric motor in the electromechanical device is the ability to stop the movement of the pedals as soon as a user desires.

In some embodiments, the processing device may receive, from one or more force sensors operatively coupled to the one or more pedals and the one or more processing devices, one or more measurements of force on the one or more pedals. The force sensors may be operatively coupled with the one or more processing devices via a wireless connection (e.g., Bluetooth) provided by wireless circuitry of the pedals. The processing device may determine whether the user has fallen from the electromechanical device based on the one or more measurements of force. Responsive to determining that the user has fallen from the electromechanical device, the processing device may lock the electric motor to stop the one or more pedals from moving.

Additionally or alternatively, the processing device may determine that feet or hands have separated from the pedals based on the one or more measurements of force. In response to determining that the feed or hands have separated from the pedals, the processing device may lock the electric motor to stop the one or more pedals from moving. Also, the processing device may present a notification on a user interface of the control system that instructs the user to place their feet or hands in contact with the pedals.

In some embodiments, the processing device may receive, from the force sensors operatively coupled to the one or more pedals, the measurements of force exerted by a user on the pedals during a pedaling session. The processing device may present the respective measurements of force on each of the pedals on a separate respective graphical scale on the user interface of the control system while the user pedals during the pedaling session. Various graphical indicators may be presented on the user interface to indicate when the force is below a threshold target range, within the threshold target range, and/or exceeds the threshold target range. Notifications may be presented to encourage the user to apply more force and/or less force to achieve the threshold target range of force. For example, the processing device is to present a first notification on the user interface when the one or more measurements of force satisfy a pressure threshold and present a second notification on the user interface when the one or more measurements do not satisfy the pressure threshold.

In addition, the processing device may provide an indicator to the user based on the one or more measurements of force. The indicator may include at least one of (1) providing haptic feedback in the pedals, handles, and/or seat of the electromechanical device, (2) providing visual feedback on the user interface (e.g., an alert, a light, a sign, etc.), (3) providing audio feedback via an audio subsystem (e.g., speaker) of the electromechanical device, or (4) illuminating a warning light of the electromechanical device.

In some embodiments, the processing device may receive, from an accelerometer of the control system, motor controller, pedal, or the like, a measurement of acceleration of movement of the electromechanical device. The processing device may determine whether the electromechanical device has moved excessively relative to a vertical axis (e.g., fallen over) based on the measurement of acceleration. Responsive to determining that the electromechanical device has moved excessively relative to the vertical axis based on the measurement of acceleration, the processing device may lock the electric motor to stop the one or more pedals from moving.

After a pedaling session is complete, the processing device may lock the electric motor to prevent the one or more pedals from moving a certain amount of time after the completion of the pedaling session. This may enable healing of the body part being rehabilitated and prevent strain on that body part by excessive movement. Upon expiration of the certain amount of time, the processing device may unlock the electric motor to enable movement of the pedals again.

The user portal may provide an option to image the body part being rehabilitated. For example, the user may place the body part within an image capture section of the user portal and select an icon to capture an image of the body part. The images may be captured before and after a pedaling session, walking session, extension session, and/or bend session. These images may be sent to the cloud-based computing system to use as training data for the machine learning model to determine the effects of the session. Further, the images may be sent to the computing device executing the clinical portal to enable the clinician to view the results of the sessions and modify the treatment plan if desired and/or provide notifications (e.g., reduce resistance, increase resistance, extend the joint further or less, etc.) to the user if desired.

Figure 4:
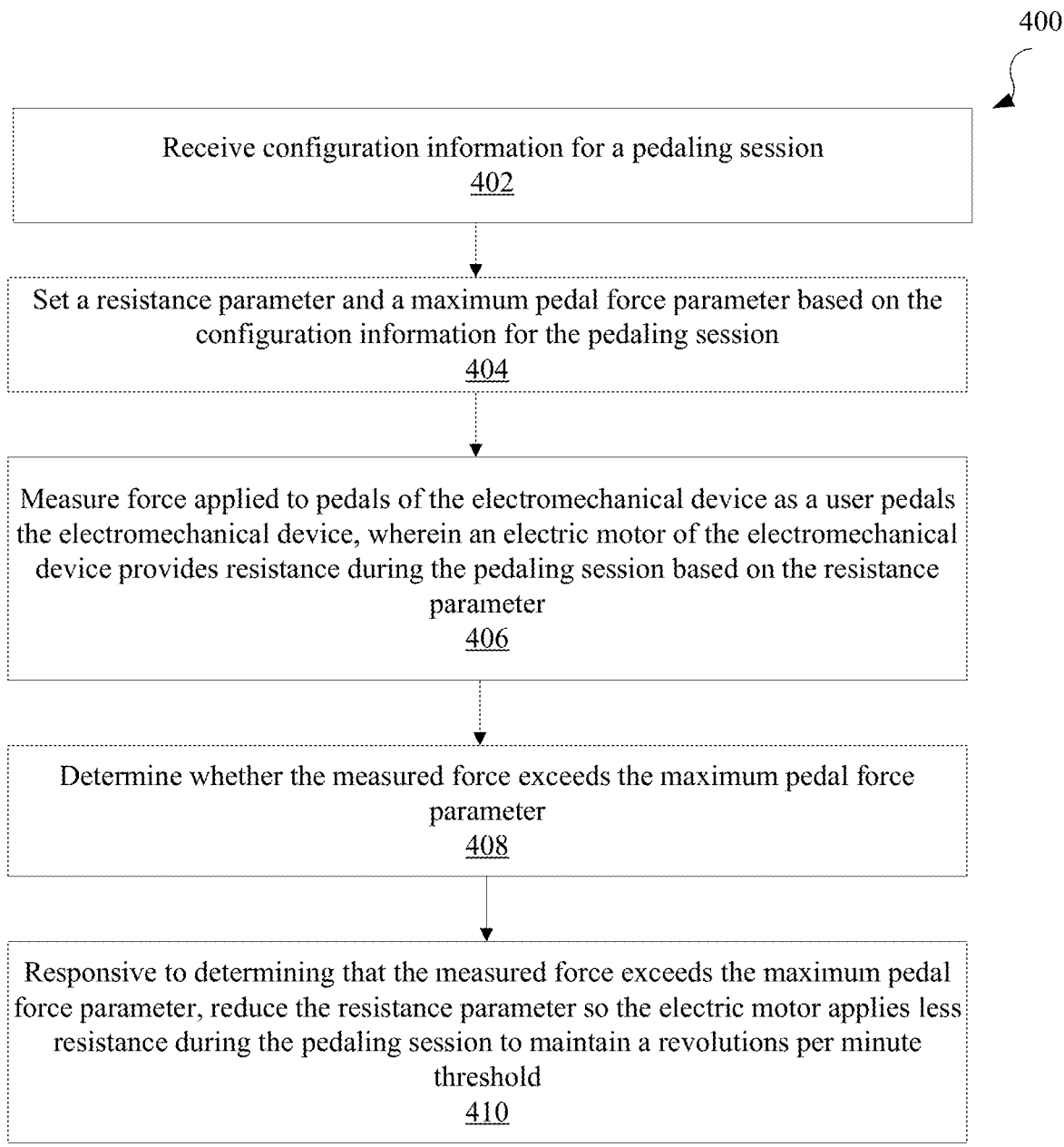
FIG. 4 illustrates example operations of a method for controlling an amount of resistance provided by an electromechanical device according to certain embodiments of this disclosure.

FIG. 4 illustrates example operations of a method 400 for controlling an amount of resistance provided by an electromechanical device according to certain embodiments of this disclosure. Method 400 includes operations performed by processing devices of the control system (e.g., computing device 102) of FIG. 1. In some embodiments, one or more operations of the method 400 are implemented in computer instructions that, when executed by a processing device, execute the control system and/or the user portal. Various operations of the method 400 may be performed by one or more of the computing device 114, the cloud-based computing system 116, the motor controller 120, the pedal 110, the goniometer 106, and/or the wristband 108. The method 400 may be performed in the same or a similar manner as described above in regards to method 300.

At block 402, the processing device may receive configuration information for a pedaling session. The configuration information may be received via selection by the user on the user portal executing on the computing device, received from the computing device executing the clinical portal, downloaded from the cloud-based computing system, retrieved from a memory device of the computing device executing the user portal, or some combination thereof. For example, the clinician may select the configuration information for a pedaling session of a patient using the clinical portal and upload the configuration information from the computing device to a server of the cloud-based computing system.

The configuration information for the pedaling session may specify one or more modes in which the electromechanical device is to operate, and configuration information specific to each of the modes, an amount of time to operate each mode, and the like. For example, for a passive mode, the configuration information may specify a position for the pedal to be in on the radially-adjustable couplings and a speed at which to control the electric motor. For the resistive mode, the configuration information may specify an amount of resistive force the electric motor is to apply to rotation of radially-adjustable couplings during the pedaling session, a maximum pedal force that is desired for the user to exert on each pedal of the electromechanical device during the pedaling session, and/or a revolutions per minute threshold for the radially-adjustable couplings. For the active-assisted mode, the configuration information may specify a minimum pedal force and a maximum pedal force that is desired for the user to exert on each pedal of the electromechanical device, a speed to operate the electric motor at which to drive one or both of the radially-adjustable couplings, and so forth.

In some embodiments, responsive to receiving the configuration information, the processing device may determine that a trigger condition has occurred. The trigger condition may include receiving a selection of a mode from a user, an amount of time elapsing, receiving a command from the computing device executing the clinical portal, or the like. The processing device may control, based on the trigger condition occurring, the electric motor to operate in a resistive mode by providing a resistance to rotation of the pedals based on the trigger condition.

At block 404, the processing device may set a resistance parameter and a maximum pedal force parameter based on the amount of resistive force and the maximum pedal force, respectively, included in the configuration information for the pedaling session. The resistance parameter and the maximum force parameter may be stored in a memory device of the computing device and used to control the electric motor during the pedaling session. For example, the processing device may transmit a control signal along with the resistance parameter and/or the maximum pedal force parameter to the motor controller, and the motor controller may drive the electric motor using at least the resistance parameter during the pedaling session.

At block 406, the processing device may measure force applied to pedals of the electromechanical device as a user operates (e.g., pedals) the electromechanical device. The electric motor of the electromechanical device may provide resistance during the pedaling session based on the resistance parameter. A force sensor disposed in each pedal and operatively coupled to the motor controller and/or the computing device executing the user portal may measure the force exerted on each pedal throughout the pedaling session. The force sensors may transmit the measured force to a processing device of the pedals, which in turn causes a communication device to transmit the measured force to the processing device of the motor controller and/or the computing device.

At block 408, the processing device may determine whether the measured force exceeds the maximum pedal force parameter. The processing device may compare the measured force to the maximum pedal force parameter to make this determination.

At block 410, responsive to determining that the measured force exceeds the maximum pedal force parameter, the processing device may reduce the resistance parameter so the electric motor applies less resistance during the pedaling session to maintain the revolutions per minute threshold specified in the configuration information. Reducing the resistance may enable the user to pedal faster, thereby increasing the revolutions per minute of the radially-adjustable couplings. Maintaining the revolutions per minute threshold may ensure that the patient is exercising the affected body part as rigorously as desired during the mode. In response to determining that the measured force does not exceed the maximum pedal force parameter, the processing device may maintain the same maximum pedal force parameter specified by the configuration information during the pedaling session.

In some embodiments, the processing device may determine than a second trigger condition has occurred. The second trigger condition may include receiving a selection of a mode from a user via the user portal, an amount of time elapsing, receiving a command from the computing device executing the clinical portal, or the like. The processing device may control, based on the trigger condition occurring, the electric motor to operate in a passive mode by independently driving one or more radially-adjustable couplings coupled to the pedals in a rotational fashion. The electric motor may drive the one or more radially-adjustable couplings at a speed specified in the configuration information without another driving source. Also, the electric motor may drive each of the one or more radially-adjustable couplings individually at different speeds.

In some embodiments, the processing device may determine that a third trigger condition has occurred. The third trigger condition may be similar to the other trigger conditions described herein. The processing device may control, based on the third trigger condition occurring, the electric motor to operate in an active-assisted mode by measuring revolutions per minute of the one or more radially-adjustable couplings coupled to the pedals and causing the electric motor to drive in a rotational fashion the one or more radially-adjustable couplings coupled to the pedals when the measured revolutions per minute satisfy a threshold condition.

In some embodiments, the processing device may receive, from a goniometer worn by the user operating the electromechanical device, a set of angles of extension between an upper leg and a lower leg at a knee of the user. The set of angles are measured as the user extends the lower leg away from the upper leg via the knee. In some embodiments, the angles of extension may represent angles between extending a lower arm away from an upper arm at an elbow. Further, the processing device may receive, from the goniometer, a set of angles of bend between the upper leg and the lower leg at the knee of the user. The set of angles of bend are measured as the user retracts the lower leg closer to the upper leg via the knee. In some embodiments, the angles of bend represent angles between bending a lower arm closer to an upper arm at an elbow.

The processing device may determine whether a range of motion threshold condition is satisfied based on the set of angles of extension and the set of angles of bend. Responsive to determining that the range of motion threshold condition is satisfied, the processing device may modify a position of one of the pedals on one of the radially-adjustable couplings to change a diameter of a range of motion of the one of the pedals. Satisfying the range of motion threshold condition may indicate that the affected body part is strong enough or flexible enough to increase the range of motion allowed by the radially-adjustable couplings.

FIG. 5 illustrates example operations of a method 500 for measuring angles of bend and/or extension of a lower leg relative to an upper leg using a goniometer according to certain embodiments of this disclosure. In some embodiments, one or more operations of the method 500 are implemented in computer instructions that are executed by the processing devices of the goniometer. 106 of FIG. 1. The method 500 may be performed in the same or a similar manner as described above in regards to method 300.

At block 502, the processing device may receive a set of angles from the one or more goniometers. The goniometer may measure angles of extension and/or bend between an upper body part (leg, arm, torso, neck, head, etc.) and a lower body part (leg, arm, torso, neck head, hand, feet, etc.) as the body parts are extended and/or bent during various sessions (e.g., pedaling session, walking session, extension session, bend session, etc.). The set of angles may be received while the user is pedaling one or more pedals of the electromechanical device.

At block 504, the processing device may transmit, via one or more network interface cards, the set of angles to a computing device controlling the electromechanical device. The electromechanical device may be operated by a user rehabilitating an affected body part. For example, the user may have recently had surgery to repair a second or third degree sprain of an anterior cruciate ligament (ACL). Accordingly, the goniometer may be secured proximate to the knee around the upper and lower leg by the affected ACL.

In some embodiments, transmitting the set of angles to the computing device controlling the electromechanical device may cause the computing device to adjust a position of one of one or more pedals on a radially-adjustable coupling based on the set of angles satisfying a range of motion threshold condition. The range of motion threshold condition may be set based on configuration information for a treatment plan received from the cloud-based computing system or the computing device executing the clinical portal. The position of the pedal is adjusted to increase a diameter of a range of motion transited by an upper body part (e.g., leg), lower body part (e.g., leg), and a joint (e.g., knee) of the user as the user opera In some embodiments, the position of the pedal may be adjusted in real-time while the user is operating the electromechanical device. In some embodiments, the user portal may present a notification to the user indicating that the position of the pedal should be modified, and the user may modify the position of the pedal and resume operating the electromechanical device with the modified pedal position.

In some embodiments, transmitting the set of angles to the computing device may cause the computing device executing the user portal to present the set of angles in a graphical animation of the lower body part and the upper body part moving in real-time during the extension or the bend. In some embodiments, the set of angles may be transmitted to the computing device executing the clinical portal, and the clinical portal may present the set of angles in a graphical animation of the lower body part and the upper body part moving in real-time during the extension or the bend. In addition, the set of angles may be presented in one or more graphs or charts on the clinical portal and/or the user portal to depict progress of the extension or bend for the user.

FIGS. 6-12 illustrate various detailed views of the components of the rehabilitation system disclosed herein.

Figure 6:
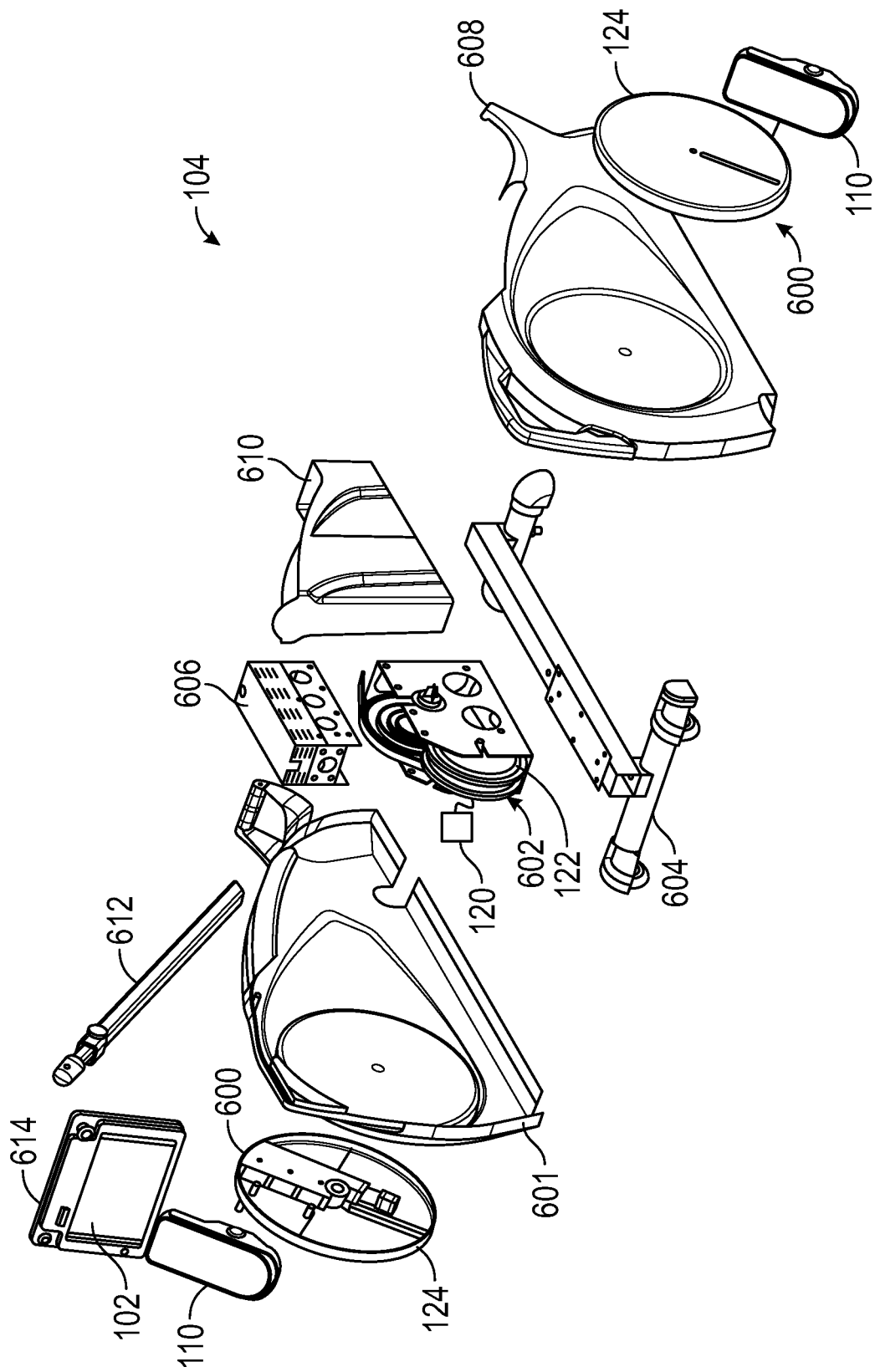
FIG. 6 illustrates an exploded view of components of the exercise and rehabilitation device according to certain embodiments of this disclosure.

For example, FIG. 6 illustrates an exploded view of components of the exercise and rehabilitation electromechanical device 104 according to certain embodiments of this disclosure. The electromechanical device 104 may include a pedal 110 that couples to a left radially-adjustable coupling 124 via a left pedal arm assembly 600 disposed within a cavity of the left radially-adjustable coupling 124. The radially-adjustable coupling 124 may be disposed in a circular opening of a left outer cover 601 and the pedal arm assembly 600 may be secured to a drive sub-assembly 602. The drive sub-assembly 602 may include the electric motor 122 that is operatively coupled to the motor controller 120. The drive sub-assembly 602 may include one or more braking mechanisms, such as disk brakes, that enable instantaneously locking the electric motor 122 or stopping the electric motor 122 over a period of time. The electric motor 122 may be any suitable electric motor (e.g., a crystallite electric motor). The drive sub-assembly 602 may be secured to a frame sub-assembly 604. A top support sub-assembly 606 may be secured on top of the drive sub-assembly 602.

A right pedal 110 couples to a left radially-adjustable coupling 124 via a right pedal arm assembly 600 disposed within a cavity of the right radially-adjustable coupling 124. The right radially-adjustable coupling 124 may be disposed in a circular opening of a right outer cover 608 and the right pedal arm assembly 600 may be secured to the drive sub-assembly 602. An internal volume may be defined when the left outer cover 601 and the right outer cover 608 are secured together around the frame sub-assembly 604. The left outer cover 601 and the right outer cover 608 may also make up the frame of the device 104 when secured together. The drive sub-assembly 602, top support sub-assembly 606, and pedal arm assemblies 600 may be disposed within the internal volume upon assembly. A storage compartment 610 may be secured to the frame.

Further, a computing device arm assembly 612 may be secured to the frame and a computing device mount assembly 614 may be secured to an end of the computing device arm assembly 612. The computing device 102 may be attached or detached from the computing device mount assembly 614 as desired during operation of the device 104.

Figure 7:
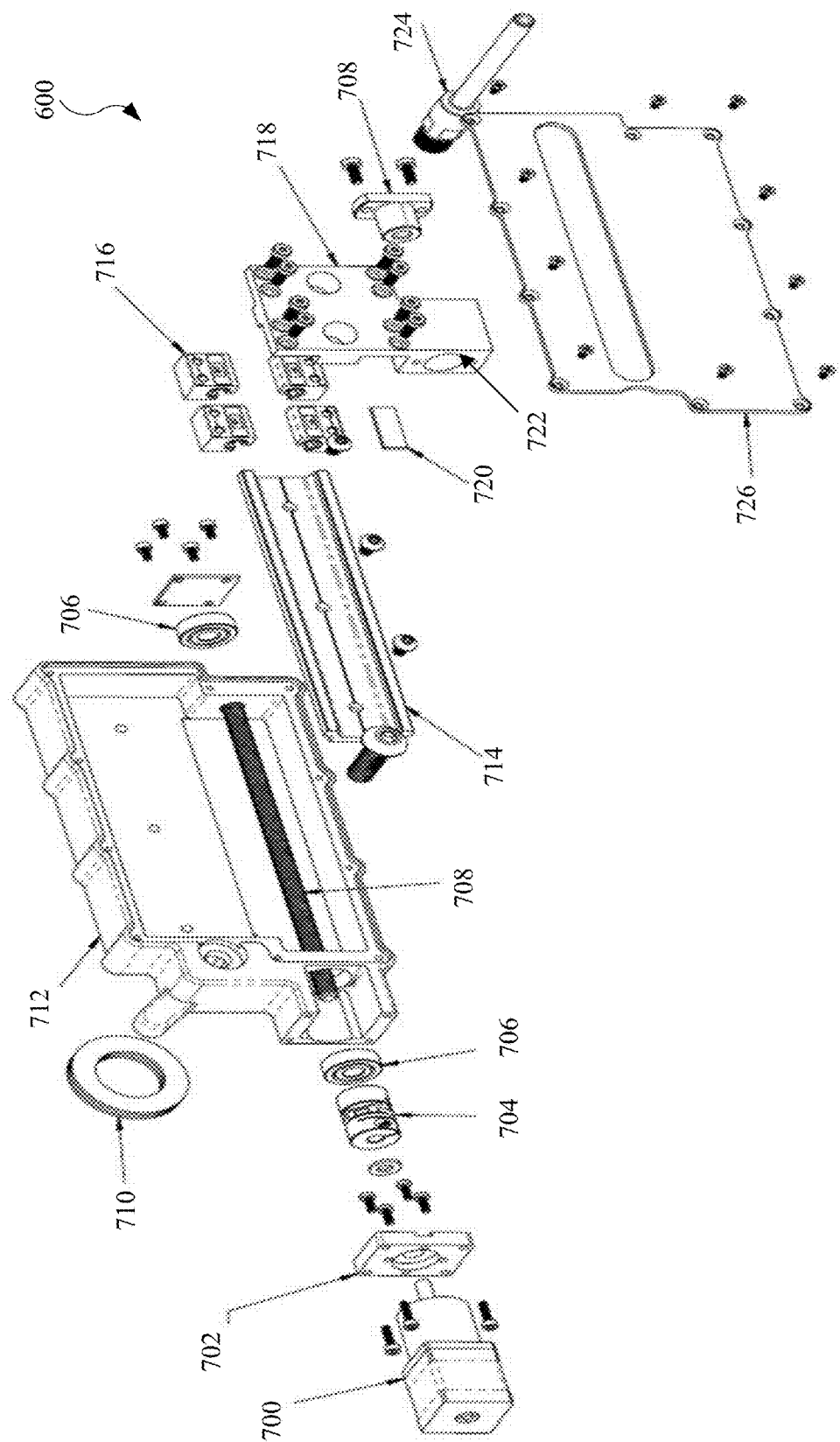
FIG. 7 illustrates an exploded view of a right pedal assembly according to certain embodiments of this disclosure.

FIG. 7 illustrates an exploded view of a pedal assembly 600 according to certain embodiments of this disclosure. The pedal assembly 600 includes a stepper motor 700. The stepper motor 700 may be any suitable stepper motor. The stepper motor 700 may include multiple coils organized in groups referred to as phases. Each phase may be energized in sequence to rotate the motor one step at a time. The control system may use the stepper motor 700 to move the position of the pedal on the radially-adjustable coupling.

The stepper motor 700 includes a barrel and pin that are inserted through a hole in a motor mount 702. A shaft coupler 704 and a bearing 706 include through holes that receive an end of a first end leadscrew 708. The leadscrew 708 is disposed in a lower cavity of a pedal arm 712. The pin of the electric motor may be inserted in the through holes of the shaft coupler 704 and the bearing 704 to secure to the first end of the leadscrew 708. The motor mount 702 may be secured to a frame of the pedal arm 712. Another bearing 706 may be disposed on another end of the leadscrew 708. An electric slip ring 710 may be disposed on the pedal arm 712.

A linear rail 714 is disposed in and secured to an upper cavity of the pedal arm 712. The linear rail 714 may be used to move the pedal to different positions as described further below. A number of linear bearing blocks 716 are disposed onto a top rib and a bottom rib of the linear rail 714 such that the bearing blocks 716 can slide on the ribs. A spindle carriage 718 is secured to each of the bearing blocks 716. A support bearing 720 is used to provide support. The lead screw may be inserted in through hole 722 of the spindle carriage 718. A lead screw unit 724 may be secured at an end of the through hole 722 to house an end of the lead screw 708. A spindle 724 is attached to a hole of the spindle carriage 718. The end of the spindle 724 protrudes through a hole of a pedal arm cover 726 when the pedal arm assembly 600 is assembled. When the stepper motor 700 turns on, the lead screw 708 can be rotated, thereby causing the spindle carriage 718 to move radially along the linear rail 714. As a result, the spindle 724 may radially traverse the opening of the pedal arm cover 726 as desired.

Figure 8:
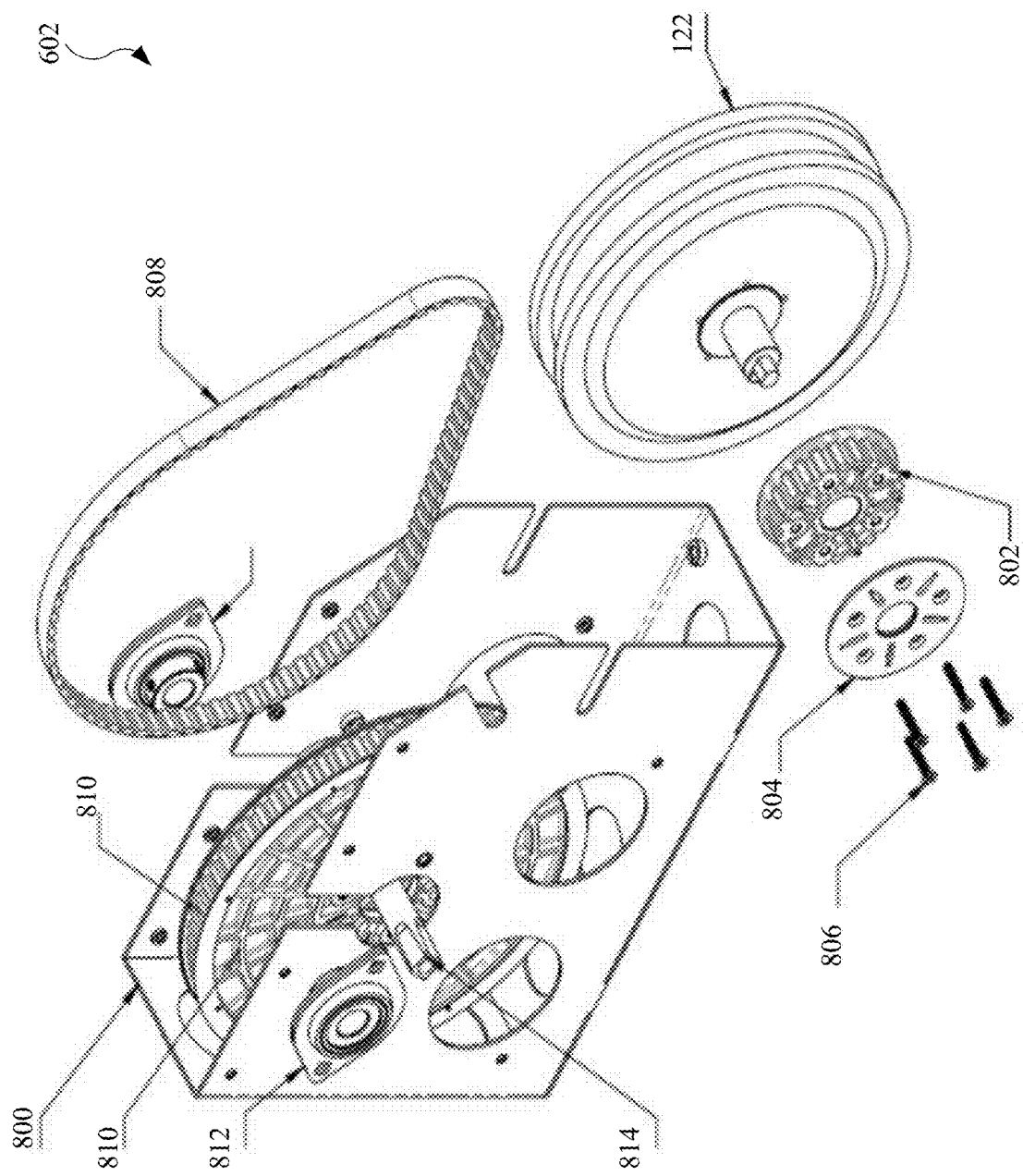
FIG. 8 illustrates an exploded view of a motor drive assembly according to certain embodiments of this disclosure.

FIG. 8 illustrates an exploded view of a drive sub-assembly 602 according to certain embodiments of this disclosure. The drive sub-assembly 602 includes an electric motor 122. The electric motor 122 is partially disposed in a crank bracket housing 800. A side of the electric motor 122 includes a small molded pulley 802 secured to it via a small pulley plate 804 by screws 806. Also disposed within the crank bracket housing 800 is a timing belt 808 and a large molded pulley 810. The timing belt 808 may include teeth on an interior side that engage with teeth on the small molded pulley 802 and the large molded pulley 810 to cause the large molded pulley 810 to rotate when the electric motor 122 operates. The crank bracket housing 800 includes mounted bearing 814 on both sides through which cranks 814 of the large molded pulley 810 protrude. The cranks 814 may be operatively coupled to the pedal assemblies.

Figure 9:
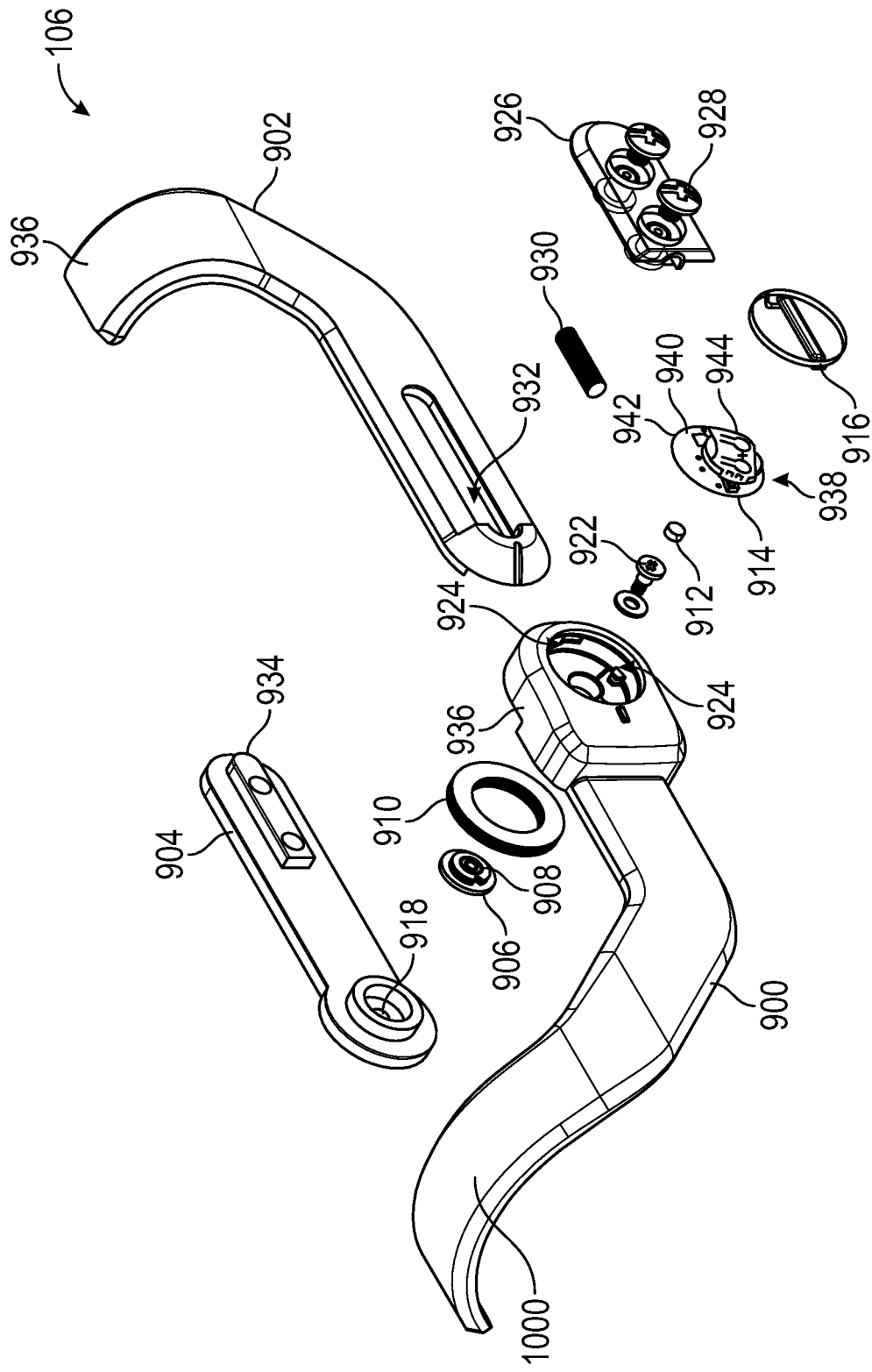
FIG. 9 illustrates an exploded view of a portion of a goniometer according to certain embodiments of this disclosure.

FIG. 9 illustrates an exploded view of a portion of a goniometer 106 according to certain embodiments of this disclosure. The goniometer 106 includes an upper section 900 and a lower section 902. The upper section 900 and the lower section 902 are rotatably coupled via a lower leg side brace 904. A bottom cap 906 may be inserted into a protruded cavity 918 of the lower leg side brace 904. In some embodiments, the bottom cap 906 includes a microcontroller 908. A thrust roller bearing 910 fits over the protruded cavity 918 of the lower leg side brace 904, which is inserted into a cavity 920 of the upper section 900 and secured to the upper section 900 via an attachment, such as a screw 922. Second cavity 924 is located on a side of the upper section 900 opposite to the side having the cavity 920 with the inserted protruded cavity 918. A radial magnet 912 and a microcontroller (e.g., a printed control board) 914 are disposed in the second cavity 924 and a top cap 916 is placed on top to cover the second cavity 924. The microcontroller 908 and/or the microcontroller 914 may include a network interface card 940 or a radio configured to communicate via a short range wireless protocol (e.g., Bluetooth), a processing device 944, and a memory device 938. Further, either or both of the microcontrollers 908 and 914 may include a magnetic sensing encoder chip that senses the position of the radial magnet 912. The position of the radial magnet 912 may be used to determine an angle of bend or extension 2118, 2218 of the goniometer 106 by the processing device (s) of the microcontrollers 908 and/or 914. The angles of bend/extension 2118, 2218 may be transmitted via the radio to the computing device 102. The lower section 902 defines an opening 932 configured to receive a protruding tab 934 and a spring 930. The spring 930 may be disposed along the opening 932 between the protruding tab 934 and a side cap 926. The side cap 926 may be coupled to the protruding tab 934 through the opening 932. One or more attachments 928 may couple the side cap 926 to the protruding tab 934. The attachment 928 may be a screw, a magnet, or any other desired attachment. The spring 930 can be configured to apply pressure on the side cap 926 to provide limited movement of the side cap 926 relative to the opening 932. The spring 930 may allow for movement of the lower section 902 relative to the upper section 900. The electronic device 106 can include additional and/or fewer components, including in different locations and/or configurations, and is not limited to those illustrated in FIG. 9.

Figure 10:
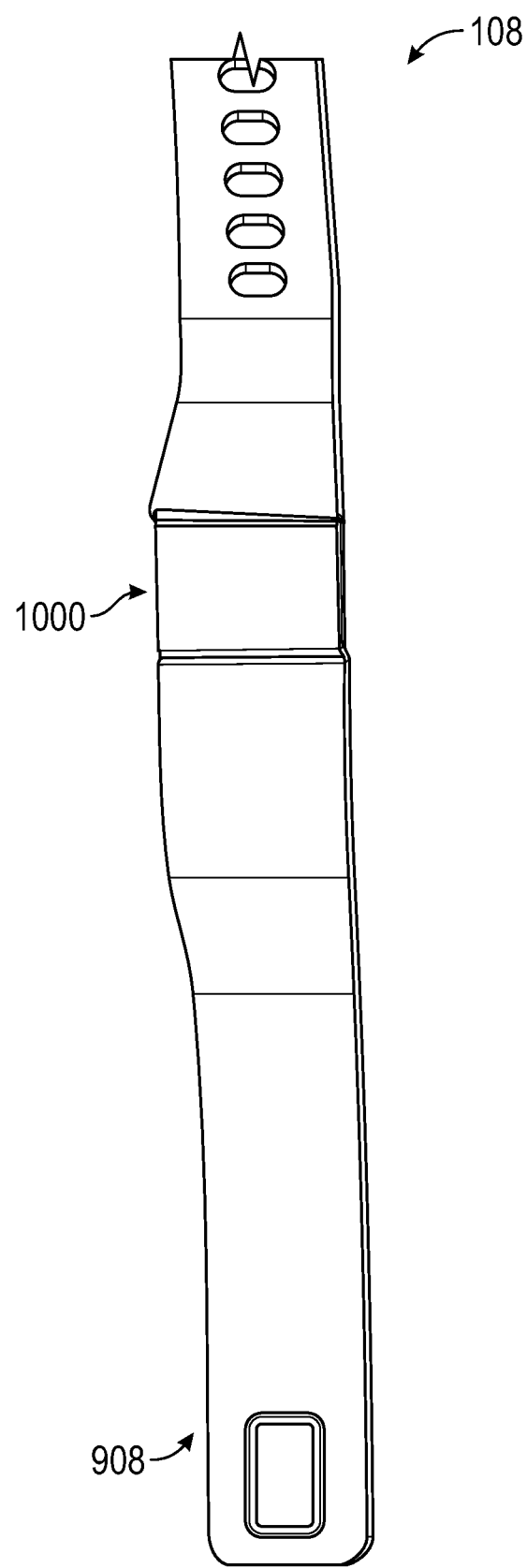
FIG. 10 illustrates a top view of a wristband according to certain embodiments of this disclosure.

FIG. 10 illustrates a top view of a wristband 108 according to certain embodiments of this disclosure. The wristband 108 includes a strap with a clasp to secure the strap to a wrist of a person. The wristband 108 may include one or more processing devices, memory devices, network interface cards, and so forth. The wristband 108 may include a display 1000 configured to present information measured by the wristband 108. The wristband 108 may include an accelerometer, gyroscope, and/or an altimeter, as discussed above. The wristband 108 may also include a light sensor to detect a heartrate of the user wearing the wristband 108. In some embodiments, the wristband 108 may include a pulse oximeter to measure an amount of oxygen (oxygen saturation) in the blood by sending infrared light into capillaries and measuring how much light is reflected off the gases. The wristband 108 may transmit the measurement data to the computing device 102.

Figure 11:
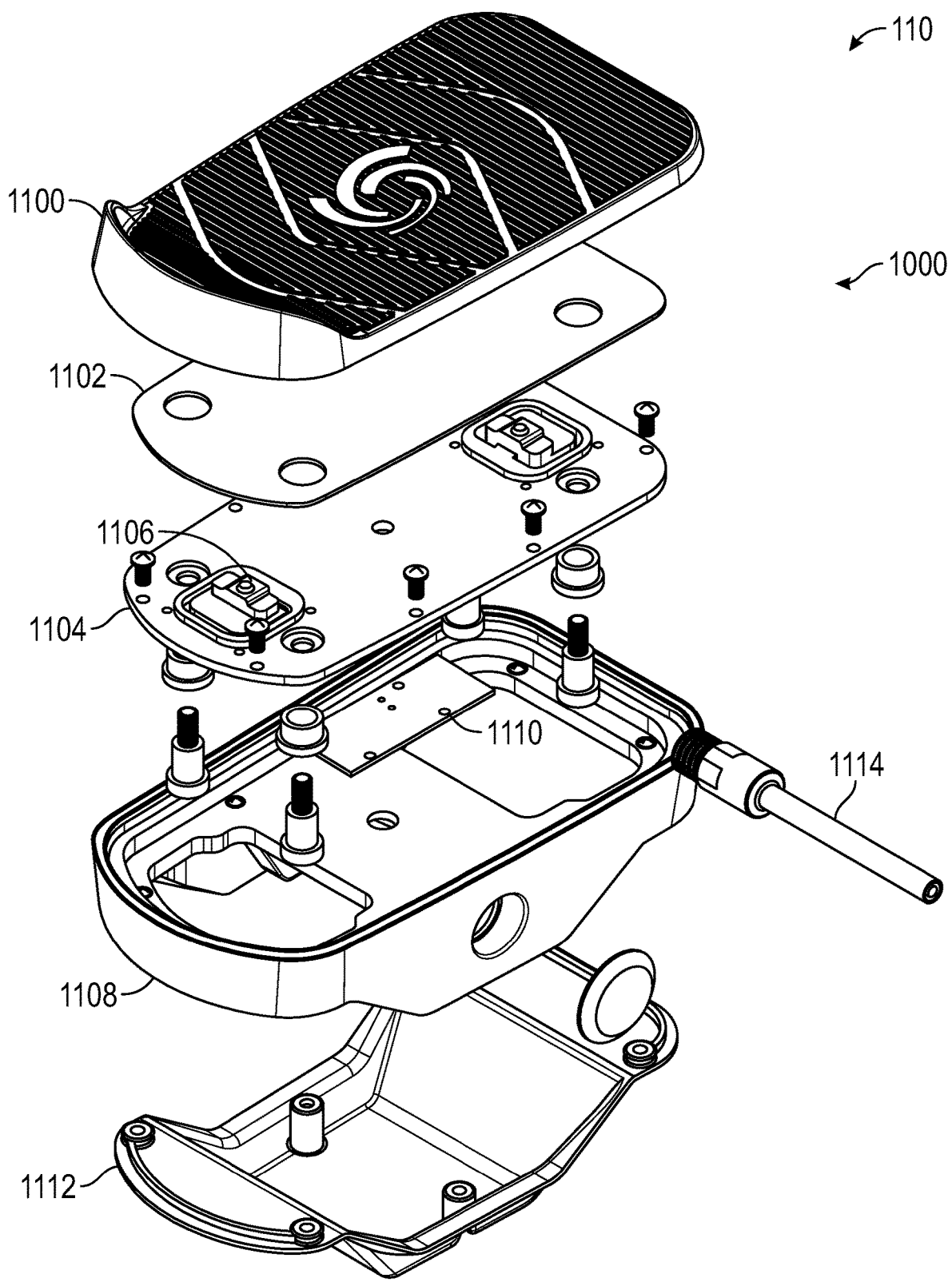
FIG. 11 illustrates an exploded view of a pedal according to certain embodiments of this disclosure.

FIG. 11 illustrates an exploded view of a pedal 110 according to certain embodiments of this disclosure. The pedal 110 includes a molded pedal top 1100 disposed on top of a molded pedal top support plate 1102. The molded pedal top 1100 and the molded pedal top support plate 1102 are secured to a molded pedal base plate 1104 via screws, for example. The molded pedal base plate 1104 includes a strain gauge 1106 configured to measure force exerted on the pedal 110. The pedal 110 also includes a molded pedal bottom 1108 where a microcontroller 1110 is disposed. The microcontroller 1110 may include processing devices, memory devices, and/or a network interface card or radio configured to communicate via a short range communication protocol, such as Bluetooth. The strain gauge 1106 is operatively coupled to the microcontroller 1110 and the strain gauge 1106 transmits the measured force to the microcontroller 1110. The microcontroller 1110 transmits the measured force to the computing device 102 and/or the motor controller 120 of the electromechanical device 104. The molded pedal top 1100, the molded pedal top support plate 1102, the molded pedal base plate 1104 are secured to the molded pedal bottom 1108, which is further secured to a molded pedal bottom cover 1112. The pedal 110 also includes a spindle 1114 that couples with the pedal arm assembly.

Figure 12:
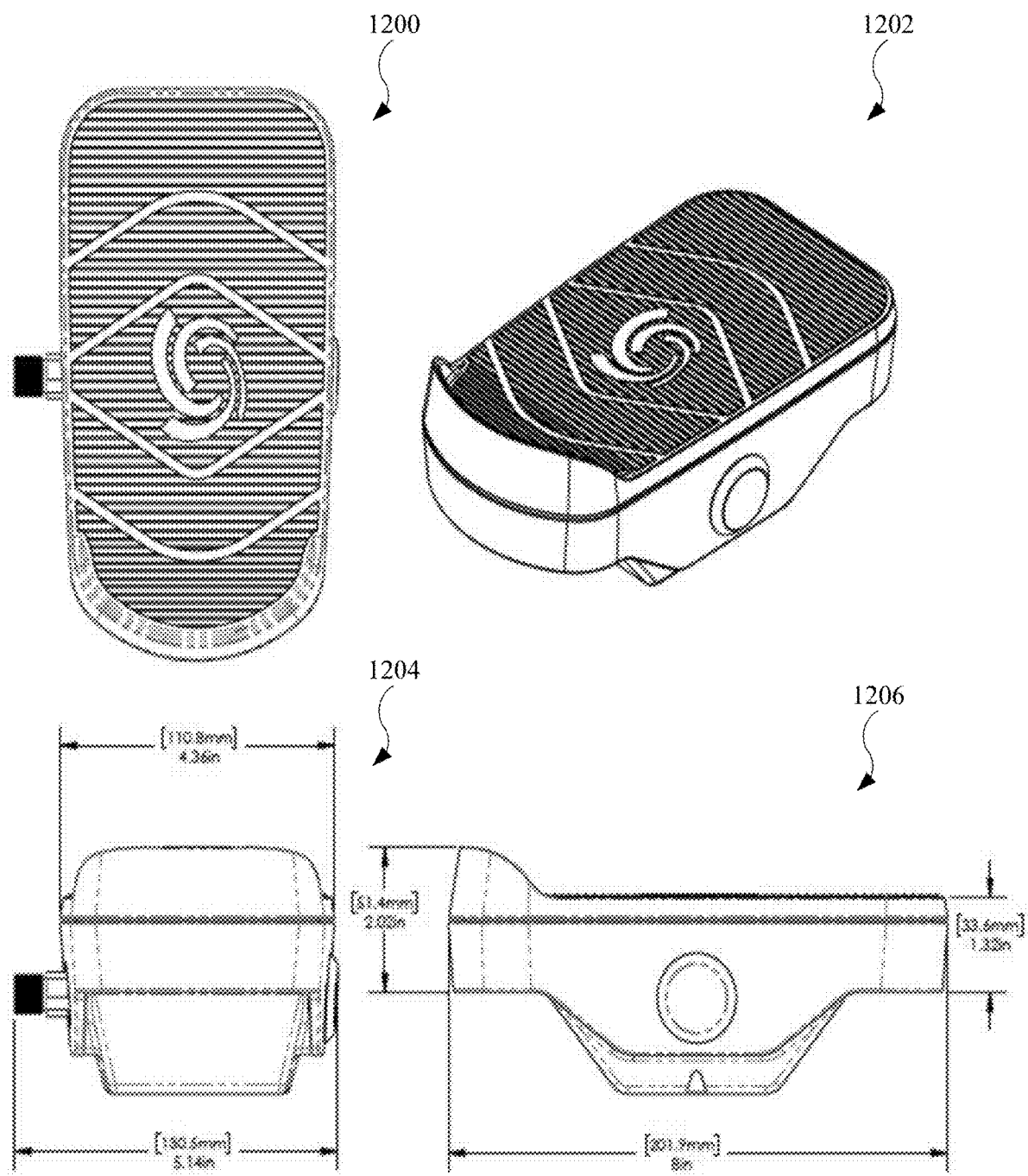
FIG. 12 illustrates additional views of the pedal according to certain embodiments of this disclosure.

FIG. 12 illustrates additional views of the pedal according to certain embodiments of this disclosure. A top view 1200 of the pedal is depicted, a perspective view 1202 of the pedal is depicted, a front view 1204 of the pedal is depicted, and a side view 1206 of the pedal is depicted.

FIGS. 13-29 illustrate different user interfaces of the user portal 118. A user may use the computing device 102, such as a tablet, to execute the user portal 118. In some embodiments, the user may hold the tablet in their hands and view the user portal 118 as they perform a pedaling session. Various user interfaces of the user portal 118 may provide prompts for the user to affirm that they are wearing the goniometer and the wristband, and that their feet are on the pedals.

Figure 13:
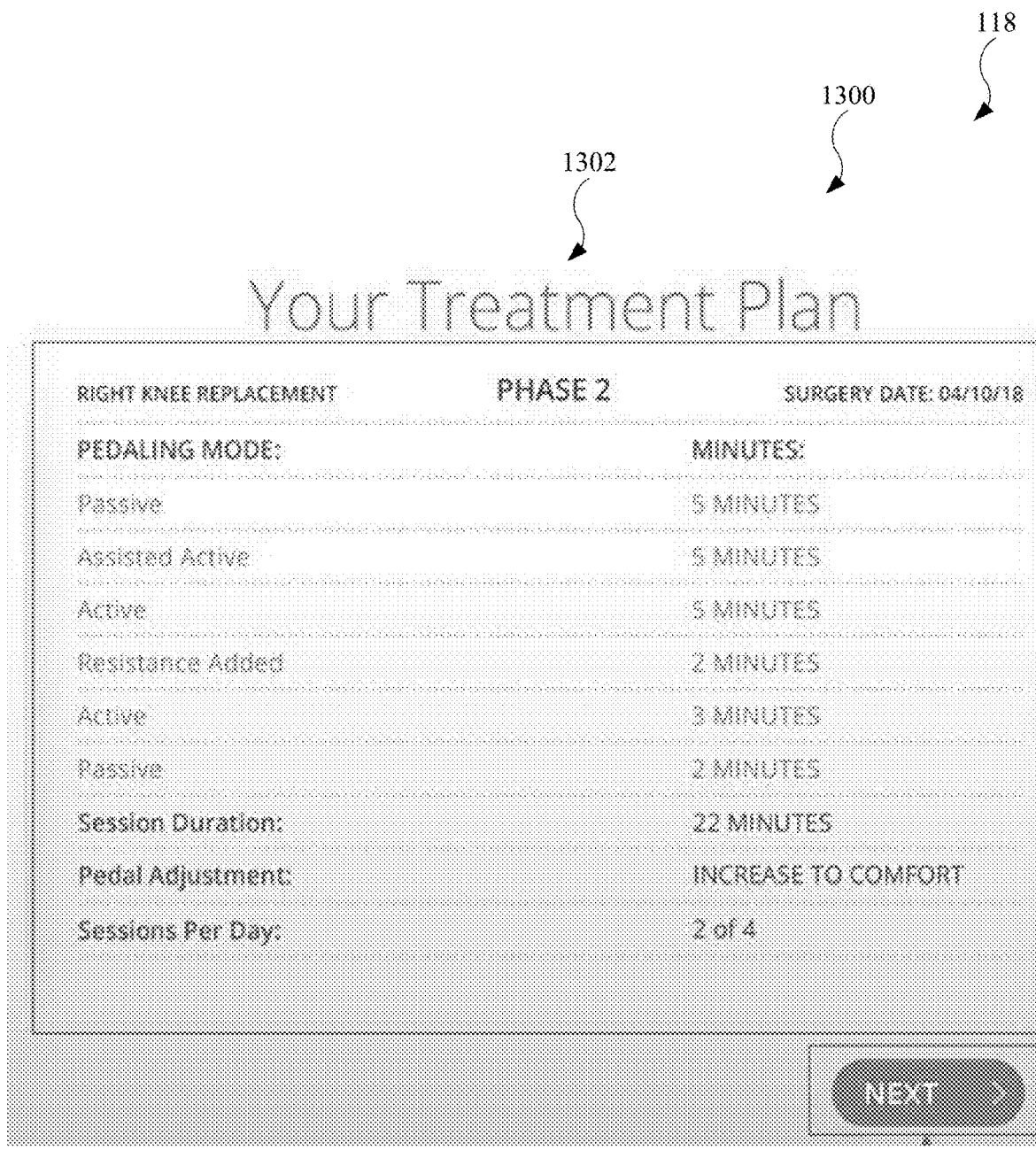
FIG. 13 illustrates an example user interface of the user portal, the user interface presenting a treatment plan for a user according to certain embodiments of this disclosure.

FIG. 13 illustrates an example user interface 1300 of the user portal 118, the user interface 1300 presenting a treatment plan 1302 for a user according to certain embodiments of this disclosure. The treatment plan 1302 may be received from the computing device 114 executing the clinical portal 126 and/or downloaded from the cloud-based computing system 116. The physician may have generated the treatment plan 1302 using the clinical portal 126 or the trained machine learning model(s) 132 may have generated the treatment plan 1302 for the user. As depicted, the treatment plan 1302 presents the type of procedure ("right knee replacement") that the patient underwent. Further, the treatment plan 1302 presents a pedaling session including a combination of the modes in which to operate the electromechanical device 104, as well as a respective set period of time for operating each of the modes. For example, the treatment plan 1302 indicates operating the electromechanical device 104 in a passive mode for 5 minutes, an active-assisted mode for 5 minutes, an active mode for 5 minutes, a resistive mode for 2 minutes, an active mode for 3 minutes, and a passive mode for 2 minutes. The total duration of the pedaling session is 22 minutes and the treatment plan 1302 also specifies that the position of the pedal may be set according to a comfort level of the patient. The user interface 1300 may be displayed as an introductory user interface prior to the user beginning the pedaling session.

Figure 14:
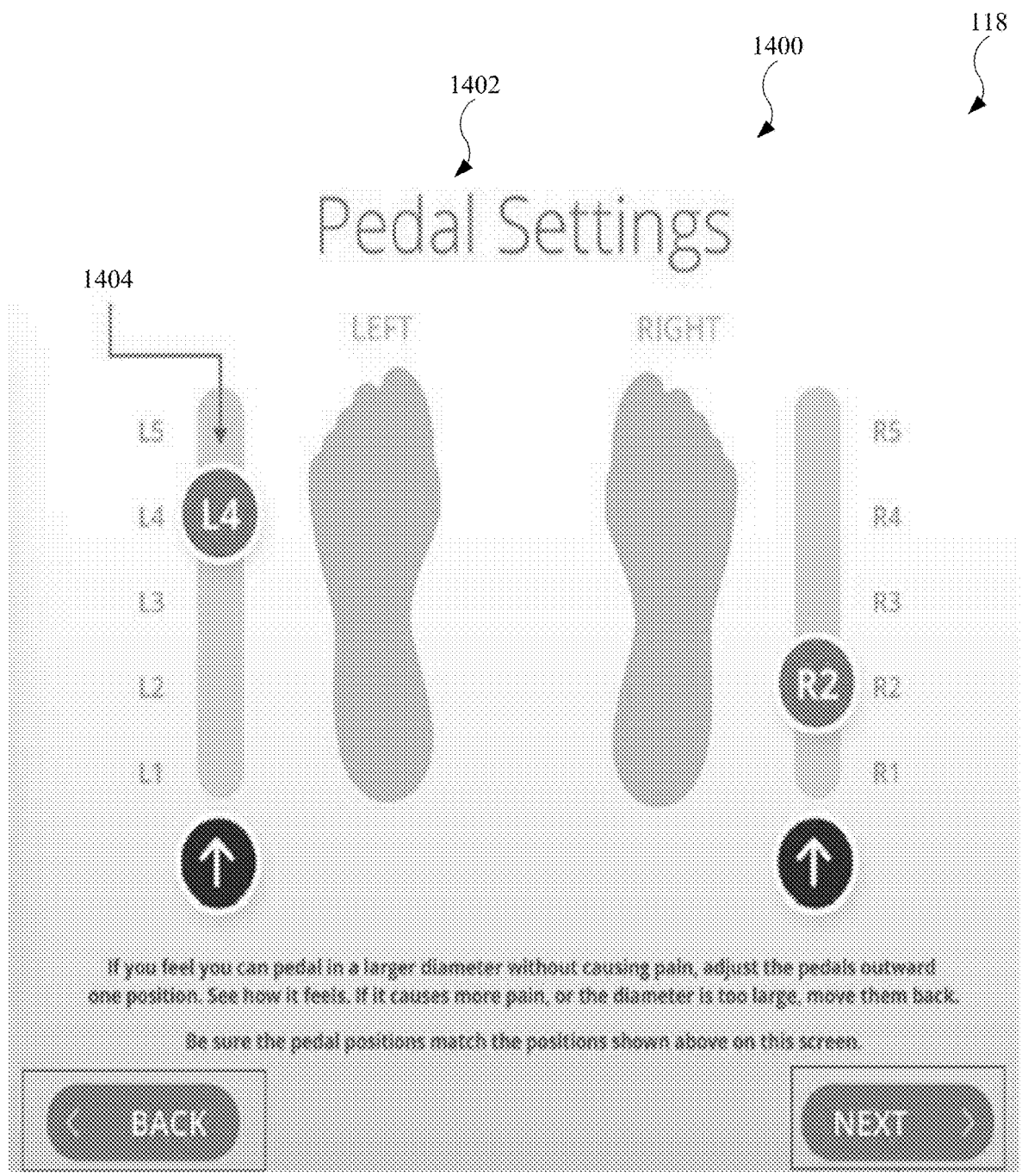
FIG. 14 illustrates an example user interface of the user portal, the user interface presenting pedal settings for a user according to certain embodiments of this disclosure.

FIG. 14 illustrates an example user interface 1400 of the user portal 118, the user interface 1400 presenting pedal settings 1402 for a user according to certain embodiments of this disclosure. As depicted graphical representation of feet are presented on the user interface 1400 and two sliders including positions corresponding to portions of the feet. For example, a left slider includes positions L1, L2, L3, L4, and L5. A right slider includes positions R1, R2, R3, R4, and R5. A button 1404 may be slid up or down on the sliders to automatically adjust the pedal position on the radially-adjustable coupling via the pedal arm assembly. The pedal positions may be automatically populated according to the treatment plan but the user has the option to modify them based on comfort level. The changed positions may be stored locally on the computing device 102, sent to the computing device 114 executing the clinical portal 126, and/or sent to the cloud-based computing system 116.

Figure 15:
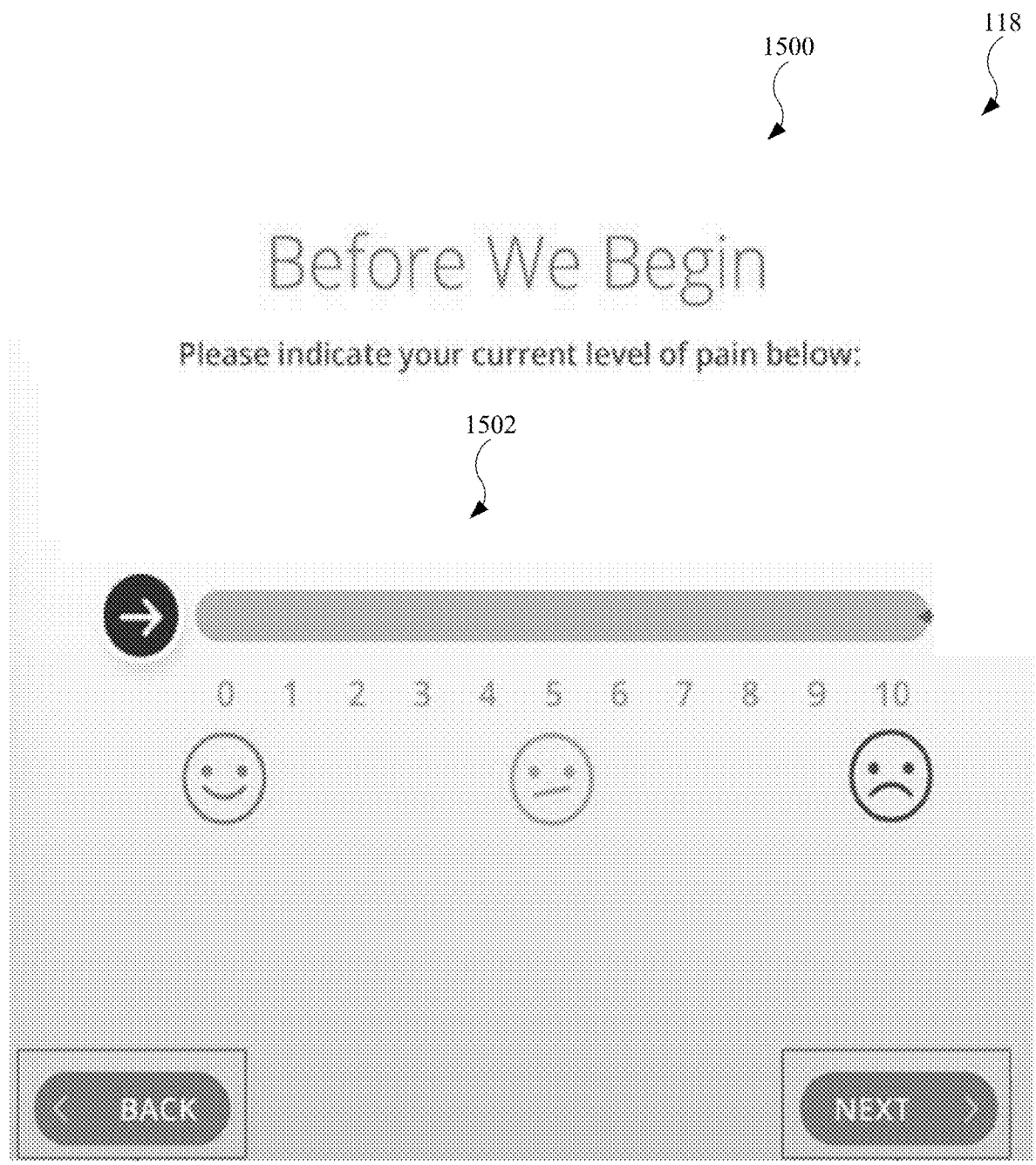
FIG. 15 illustrates an example user interface of the user portal, the user interface presenting a scale for measuring pain of the user at a beginning of a pedaling session according to certain embodiments of this disclosure.

FIG. 15 illustrates an example user interface 1500 of the user portal 118, the user interface 1500 presenting a scale 1502 for measuring discomfort of the user at a beginning of a pedaling session according to certain embodiments of this disclosure. The scale 1502 may provide options ranging for no discomfort (e.g., smiley face), mild discomfort, to high discomfort. This discomfort information may be stored locally on the computing device 102, sent to the computing device 114 executing the clinical portal 126, and/or sent to the cloud-based computing system 116.

Figure 16:
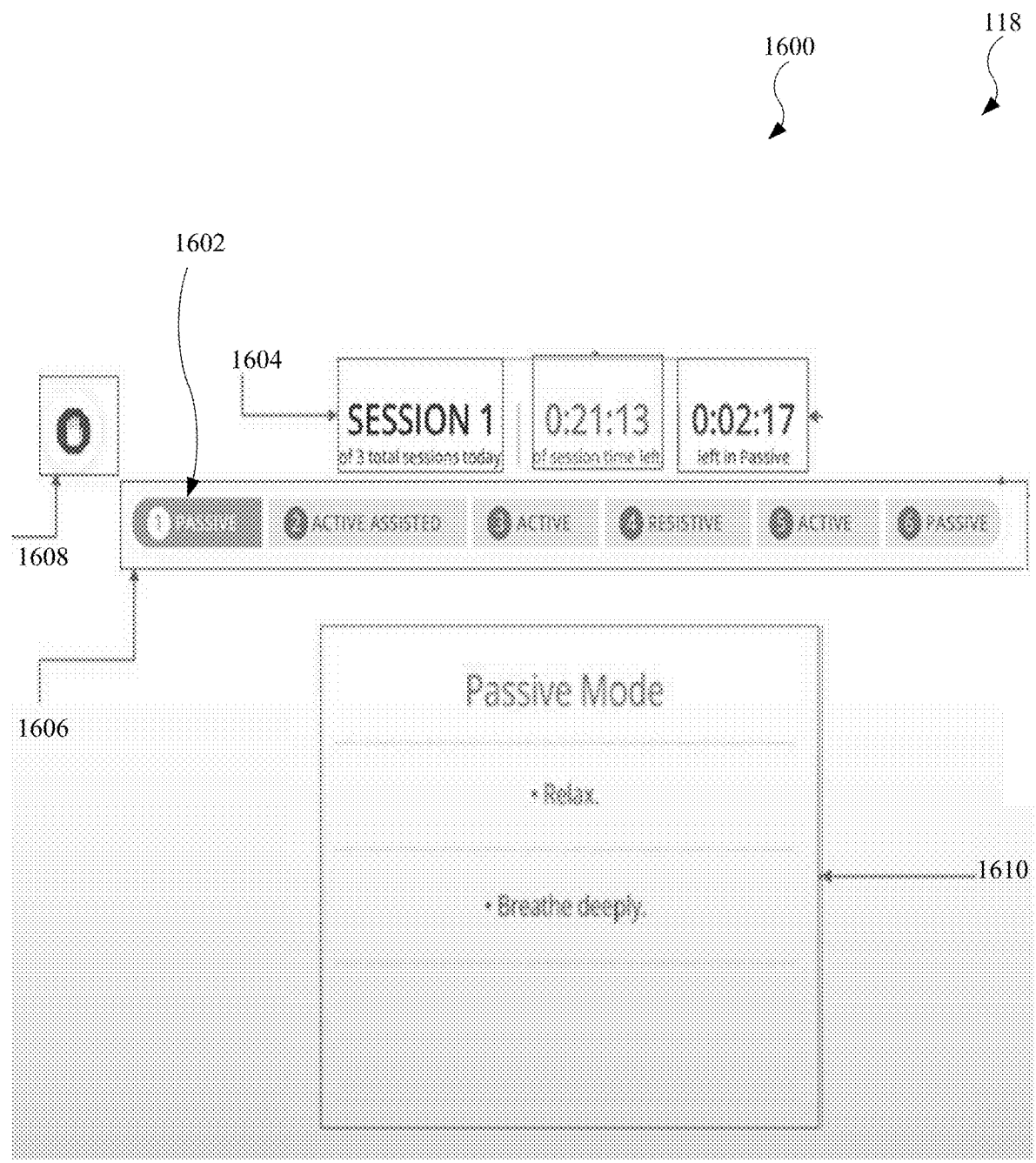
FIG. 16 illustrates an example user interface of the user portal, the user interface presenting that the electromechanical device is operating in a passive mode according to certain embodiments of this disclosure.

FIG. 16 illustrates an example user interface 1600 of the user portal 118, the user interface 118 presenting that the electromechanical device 104 is operating in a passive mode 1602 according to certain embodiments of this disclosure. The user interface 1600 presents which pedaling session 1604 (session 1) is being performed and how many other pedaling sessions are scheduled for the day. The user interface 1600 also presents an amount of time left in the pedaling session 1604 and an amount of time left in the current mode (passive mode). The full lineup of modes in the pedaling session 1604 are displayed in box 1606. While in the passive mode, the computing device controls the electric motor to independently drive the radially-adjustable couplings so the user does not have to exert any force on the pedals but their affected body part and/or muscles are stretched and warmed up. At any time, if the user so desires, the user may select a stop button 1608, which causes the electric motor to lock and stop the rotation of the radially-adjustable couplings instantaneously or over a set period of time. A descriptive box 1610 may provide instructions related to the current mode to the user.

FIGS. 17A-D illustrates an example user interface 1700 of the user portal 118, the user interface 1700 presenting that the electromechanical device 104 is operating in active-assisted mode 1702 and the user is applying various amounts of force to the pedals according to certain embodiments of this disclosure. Graphical representations 1702 of feet are presented on the user interface 1700 and the graphical representations may fill up based on the amount of force measured at the pedals. The force sensors (e.g., strain gauge) in the pedal may measure the forces exerted by the user and the microcontroller of the pedal may transmit the force measurements to the computing device 102. Notifications may be presented when the amount of force is outside of a threshold target force (e.g., either below a range of threshold target force or above the range of threshold target force). For example, in FIG. 17A, the right foot includes a notification to apply more force with the right foot because the current force measured at the pedal is below the threshold target force.

A virtual tachometer 1706 is also presented that measures the revolutions per minute of the radially-adjustable and displays the current speed that the user is pedaling. The tachometer 1706 includes areas 1708 (between 0 and 10 revolutions per minute and between 20 and 30 revolutions per minute) that the user should avoid according to their treatment plan. In the depicted example, the treatment plan specifies the user should keep the speed between 10 and 20 revolutions per minute. The electromechanical device 104 transmits the speed to the computing device 102 and the needle 1710 moves in real-time as the user operates the pedals. Notifications are presented near the tachometer 1706 that may indicate that the user should keep the speed above a certain threshold revolutions per minute (e.g., 10 RPM). If the computing device 102 receives a speed from the device 104 and the speed is below the threshold revolutions per minute, the computing device 102 may control the electric motor to drive the radially-adjustable couplings to maintain the threshold revolutions per minute.

Figure 17A:
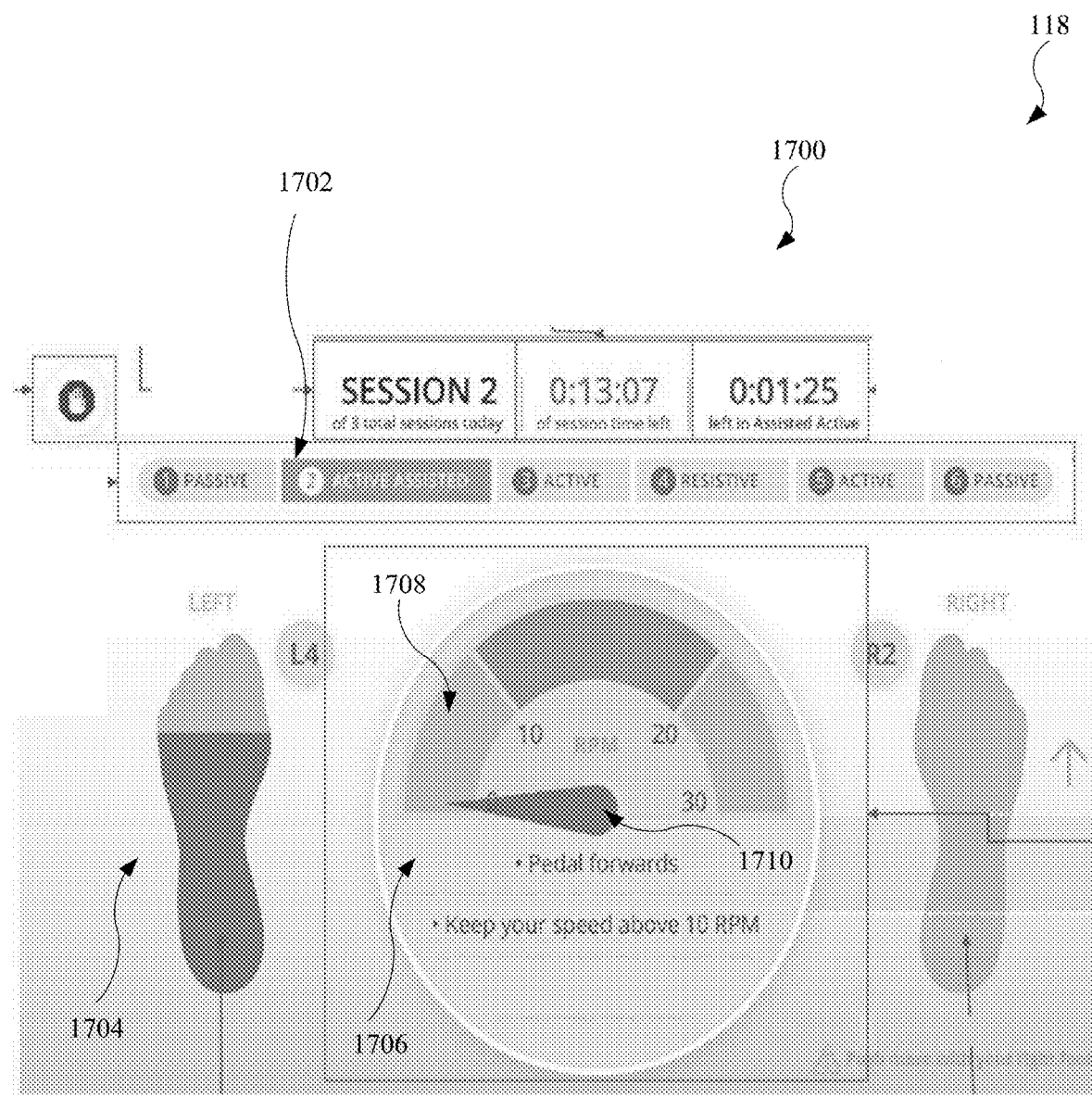
FIGS. 17A-D illustrates an example user interface of the user portal, the user interface presenting that the electromechanical device is operating in active-assisted mode and the user is applying various amounts of force to the pedals according to certain embodiments of this disclosure.
Figure 17B:
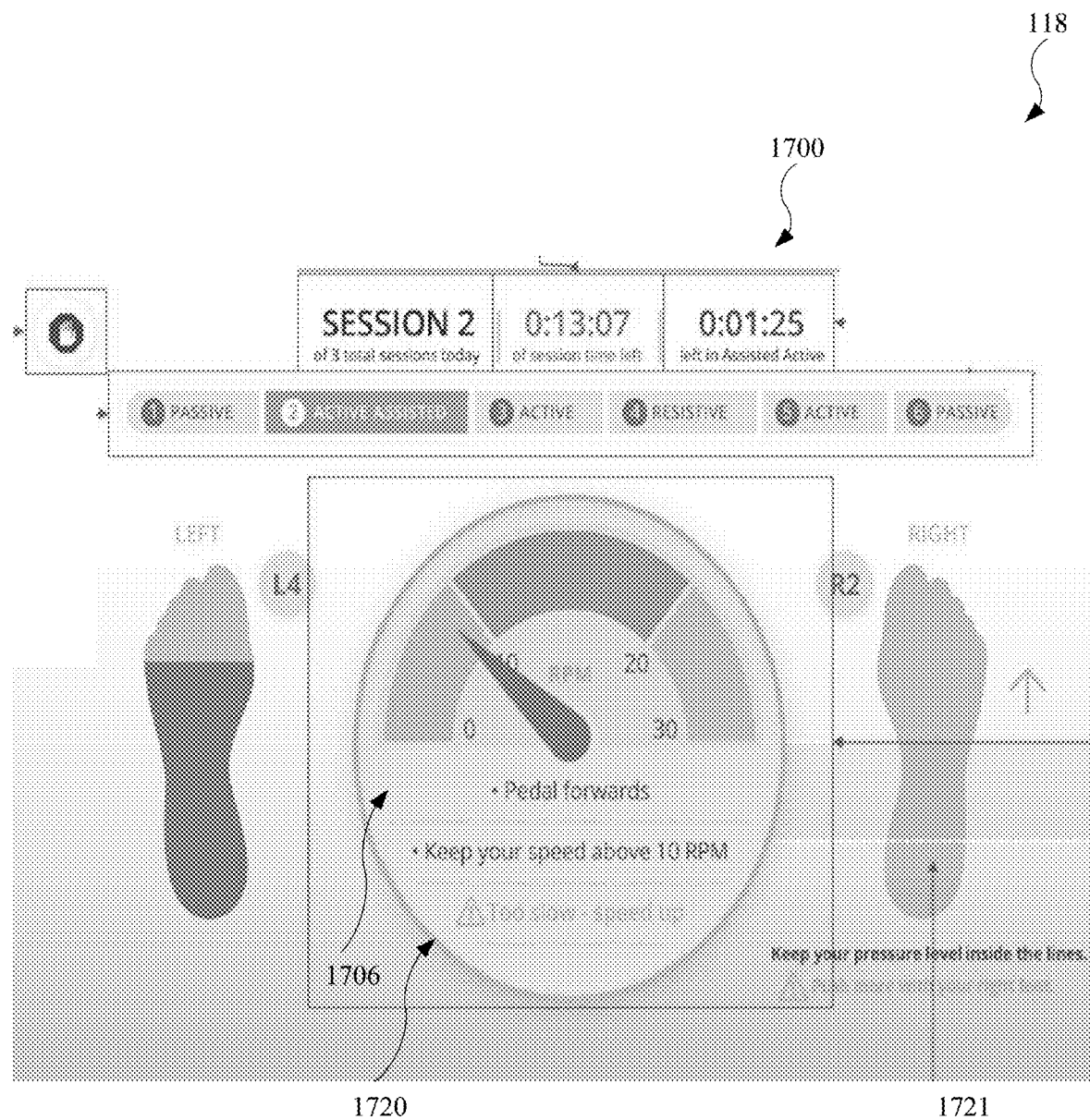
Figure 17C:
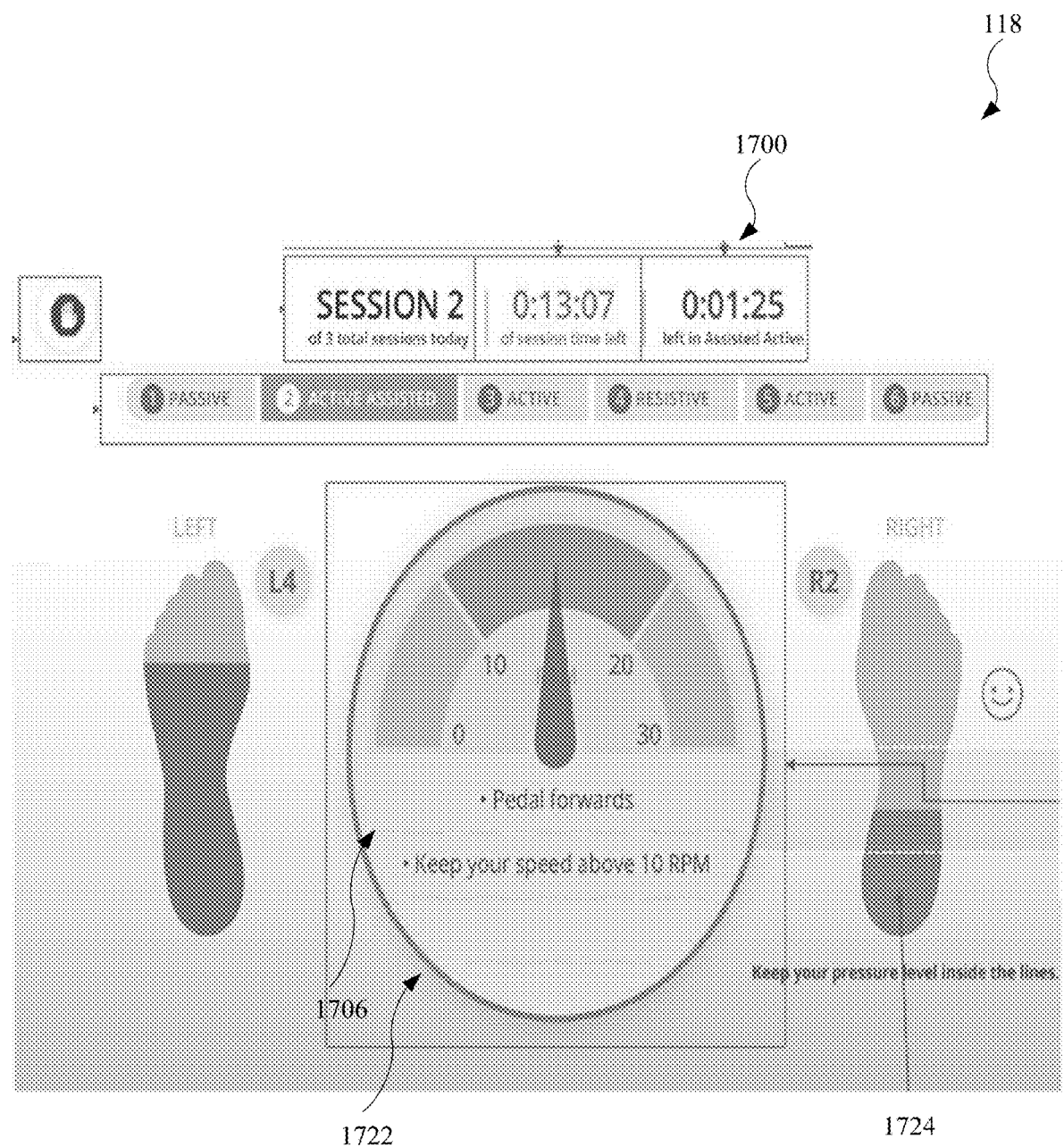
Figure 17D:
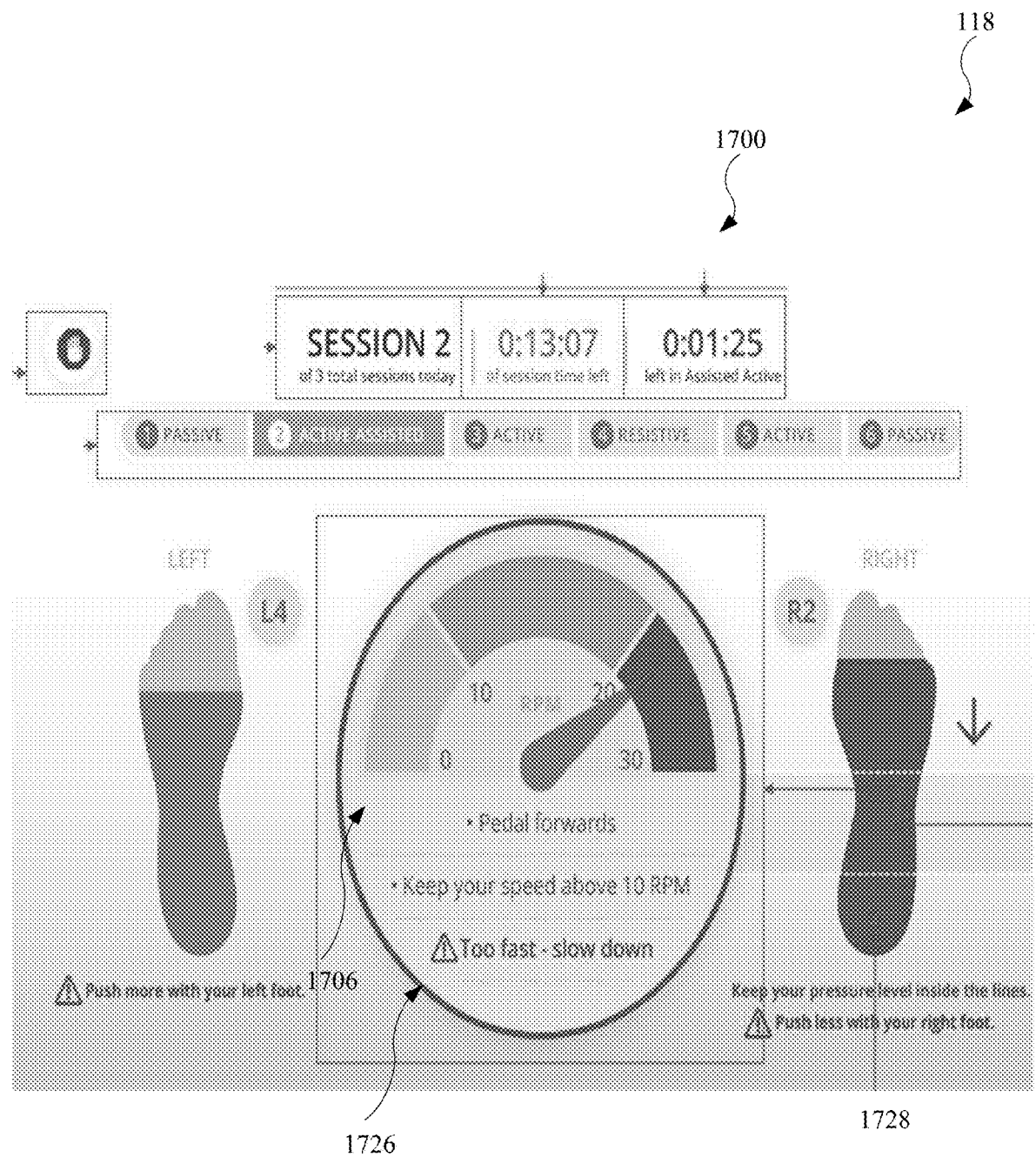

FIG. 17B depicts the example user interface 1700 presenting a graphic 1720 for the tachometer 1706 when the speed is below the threshold revolutions per minute. As depicted, a notification is presented that says "Too slow—speed up". Also, the user interface 1700 presents an example graphical representation 1721 of the right foot when the pressure exerted at the pedal is below the range of threshold target force. A notification may be presented that reads "Push more with your right foot." FIG. 17C depicts the example user interface 1700 presenting a graphic 1722 for the tachometer 1706 when the speed is within the desired target revolutions per minute. Also, the user interface 1700 presents an example graphical representation 1724 of the right foot when the pressure exerted at the pedal is within the range of threshold target force. FIG. 17D depicts the example user interface 1700 presenting a graphic 1726 for the tachometer 1706 when the speed is above the desired target revolutions per minute. As depicted, a notification is presented that reads "Too fast—slow down". Also, the user interface 1700 presents an example graphical representation 1728 of the right foot when the pressure exerted at the pedal is above the range of threshold target force. A notification may be presented that reads "Push less with your right foot."

Figure 18:
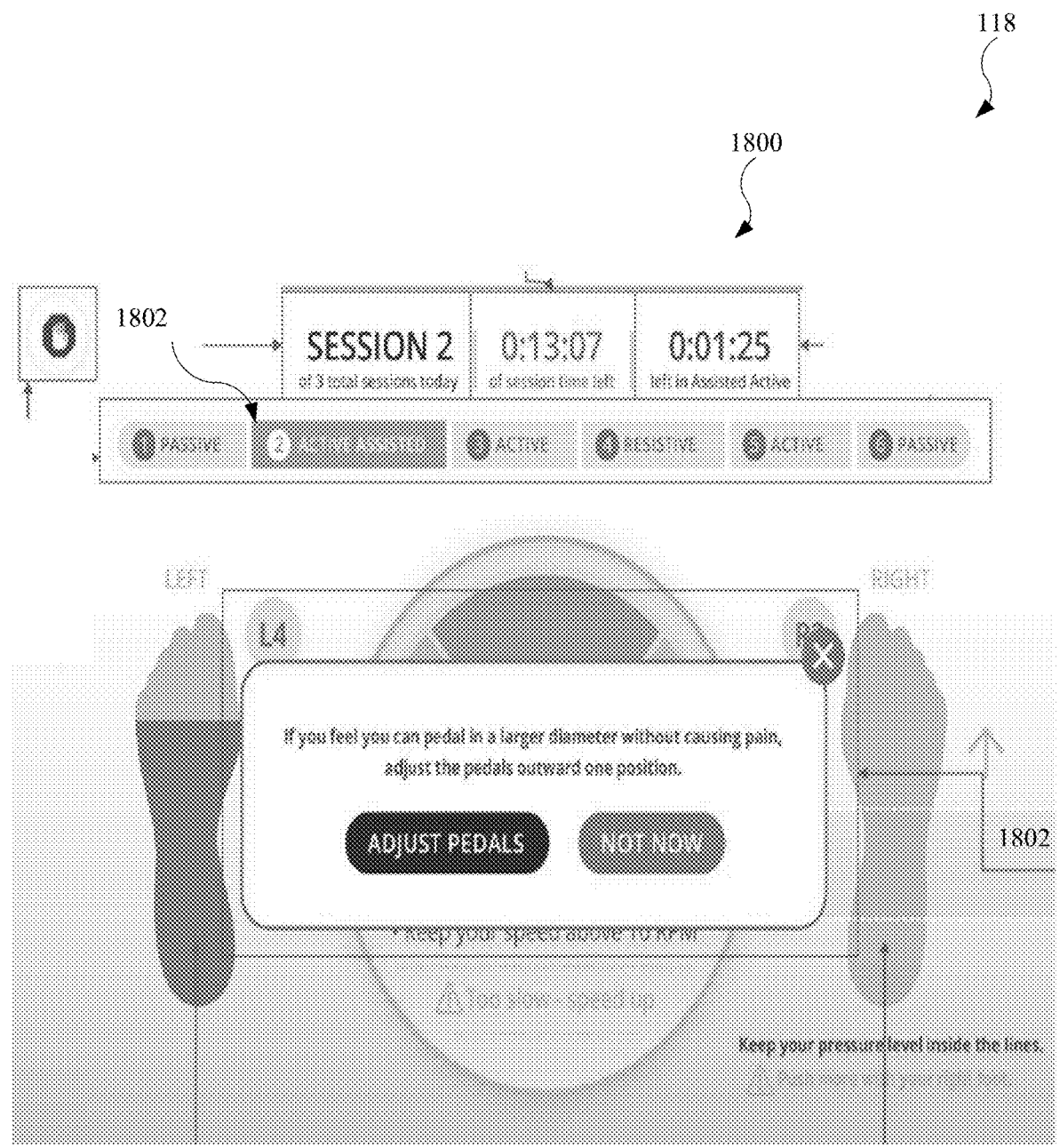
FIG. 18 illustrates an example user interface of the user portal, the user interface presenting a request to modify pedal position while the electromechanical device is operating in active-assisted mode according to certain embodiments of this disclosure.

FIG. 18 illustrates an example user interface 1800 of the user portal 118, the user interface 1800 presenting a request 1802 to modify pedal position while the electromechanical device 104 is operating in active-assisted mode according to certain embodiments of this disclosure. The request 1802 may pop up on a regular interval as specified in the treatment plan. If the user selects the "Adjust Pedals" button, the user portal 118 may present a screen that allows the user to modify the position of the pedals.

FIG. 19 illustrates an example user interface 1900 of the user portal 118, the user interface 1900 presenting a scale 1902 for measuring discomfort of the user at an end of a pedaling session according to certain embodiments of this disclosure. The scale 1902 may provide options ranging for no discomfort (e.g., smiley face), mild discomfort, to high discomfort. This discomfort information may be stored locally on the computing device 102, sent to the computing device 114 executing the clinical portal 126, and/or sent to the cloud-based computing system 116.

Figure 20:
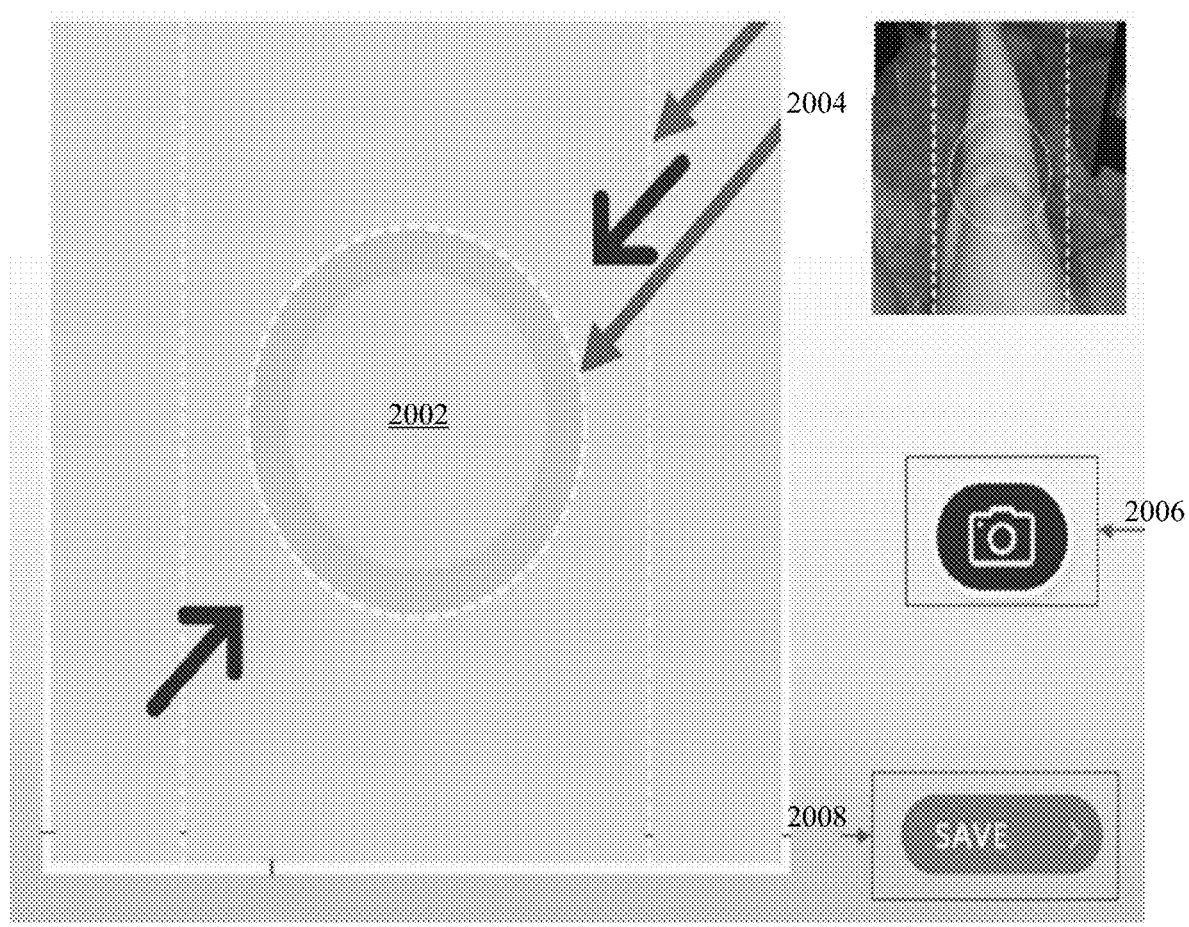
FIG. 20 illustrates an example user interface of the user portal, the user interface enabling the user to capture an image of the body part under rehabilitation according to certain embodiments of this disclosure.

FIG. 20 illustrates an example user interface 2000 of the user portal 118, the user interface 2000 enabling the user to capture an image of the body part under rehabilitation according to certain embodiments of this disclosure. For example, an image capture zone 2002 is presented on the user interface 2000 and the dotted lines 2004 will populate to show a rough outline of the leg, for example, with a circle to indicate where their kneecap (patella) should be in the image. This enables the patient to line up their leg/knee for the image. The user may select a camera icon 2006 to capture the image. If the user is satisfied with the image, the user can select a save button 2008 to store the image on the computing device 102 and/or in the cloud-based computing system 116. Also, the image may be transmitted to the computing device 114 executing the clinical portal 126.

Figure 21A:
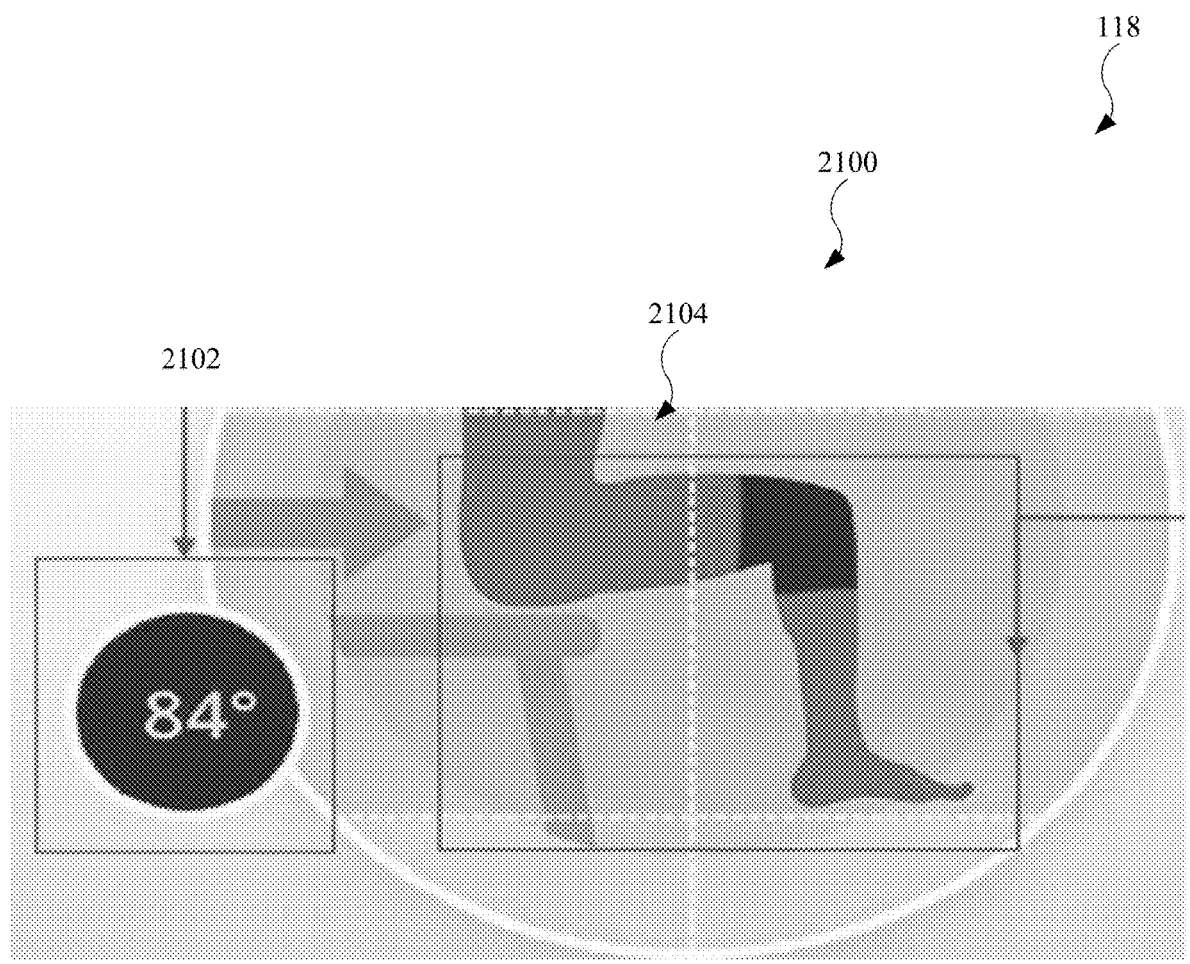
FIGS. 21A-D illustrate an example user interface of the user portal, the user interface presenting angles of extension and bend of a lower leg relative to an upper leg according to certain embodiments of this disclosure.

FIGS. 21A-D illustrate an example user interface 2100 of the user portal 118. The user interface 2100 presents angles 2102 of an extension 2222 or a bend 2122 of a lower leg relative to an upper leg according to certain embodiments of this disclosure. As depicted in FIG. 21A, the user interface 2100 presents a graphical animation 2104 of the user's leg extending in real-time. The knee angle in the graphical animation 2104 may match the angle 2102 presented on the user interface 2100, for example, an angle of bend 2118 or an angle of extension 222. The computing device 102 may receive the angles of extension 2218 from the electronic device 106, and such device may be a goniometer or any other desired device that is worn by the user 2108 during an extension session and/or a pedaling session. To that end, although the graphical animation 2104 depicts the user 2108 extending his or her leg during an extension session, it should be understood that the user portal 118 may be configured to display the angles 2102 in real-time as the user 2108 operates the pedals 110 of the electromechanical device 104 in real-time.

Figure 21B:
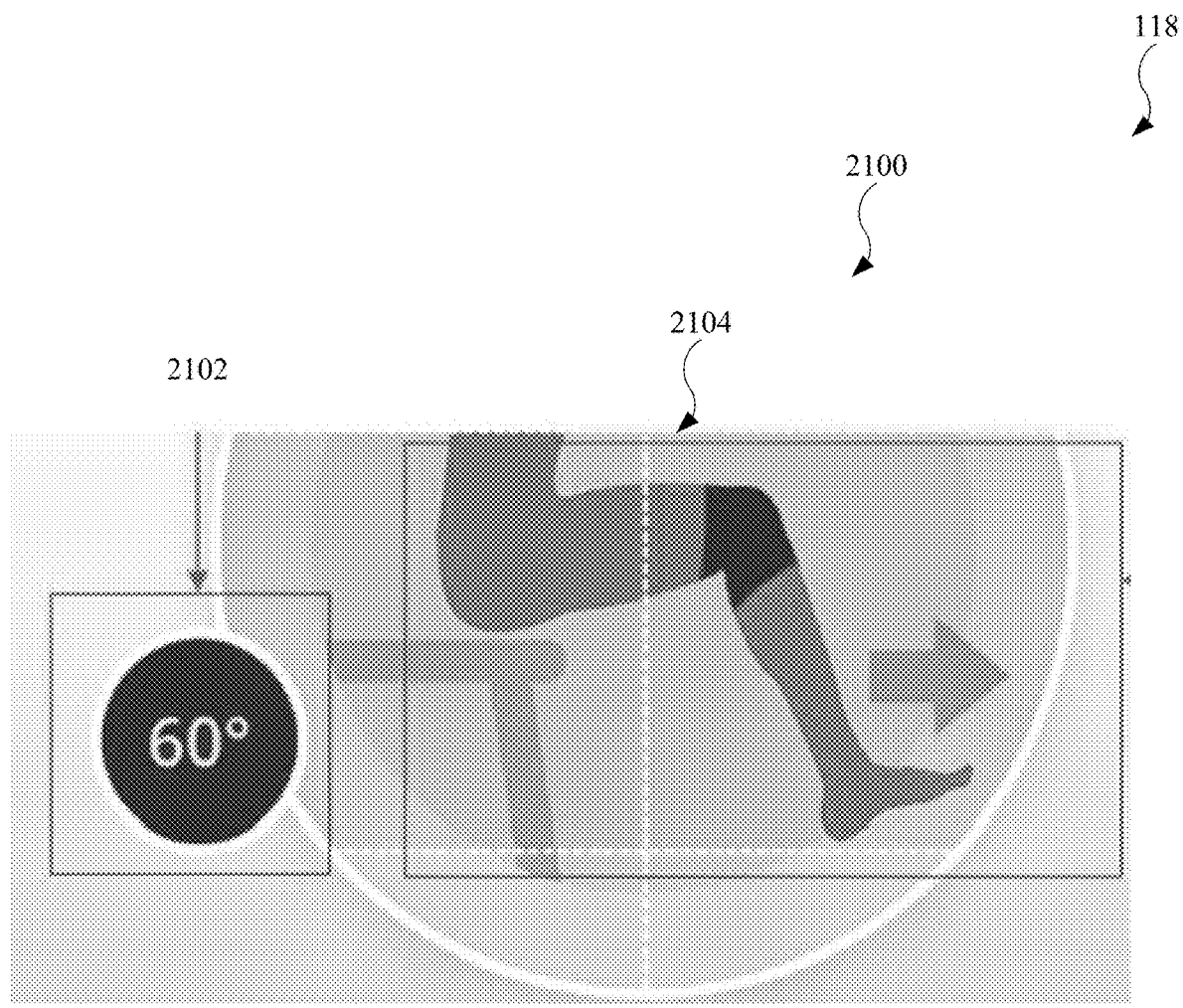
Figure 21C:
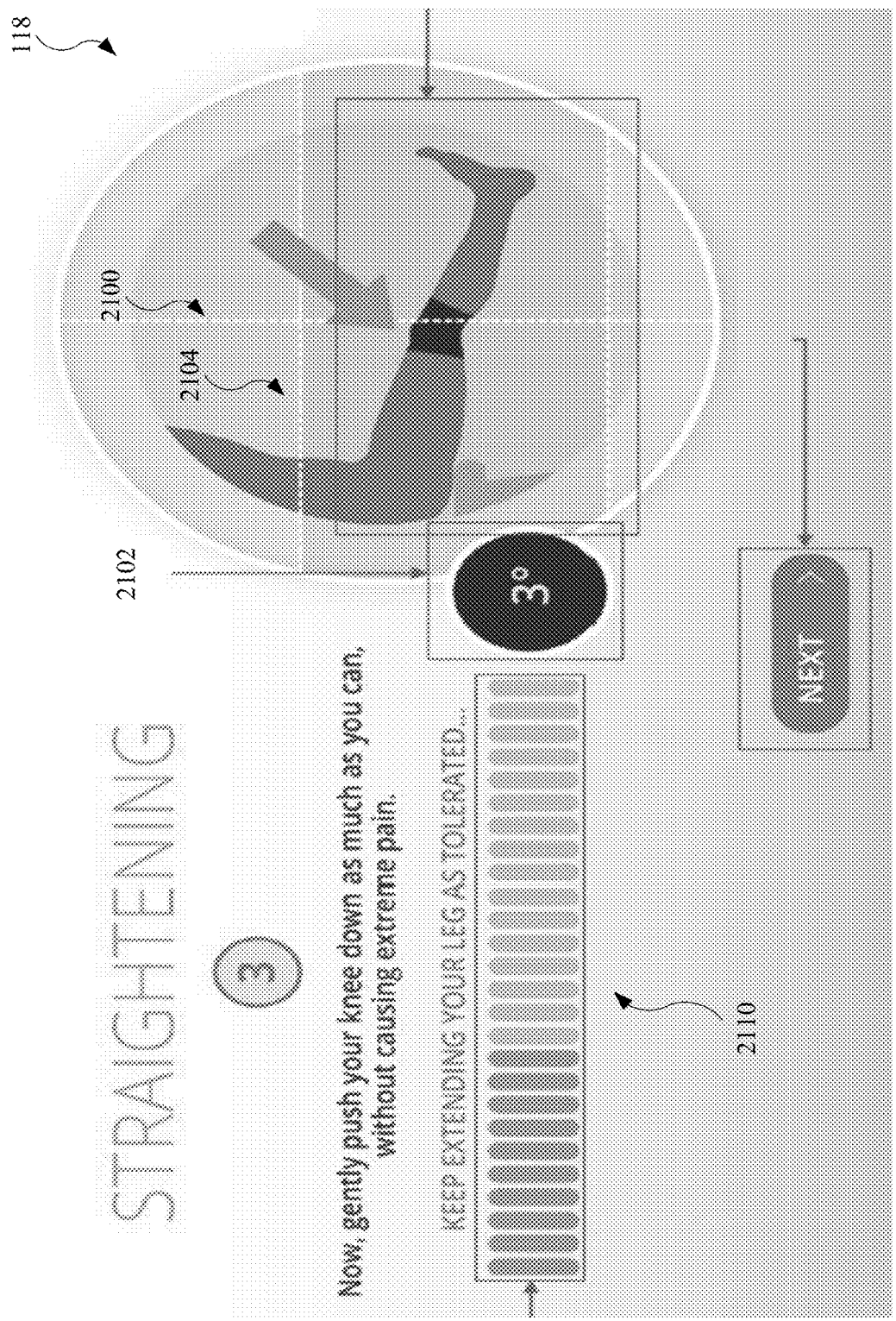
Figure 21D:
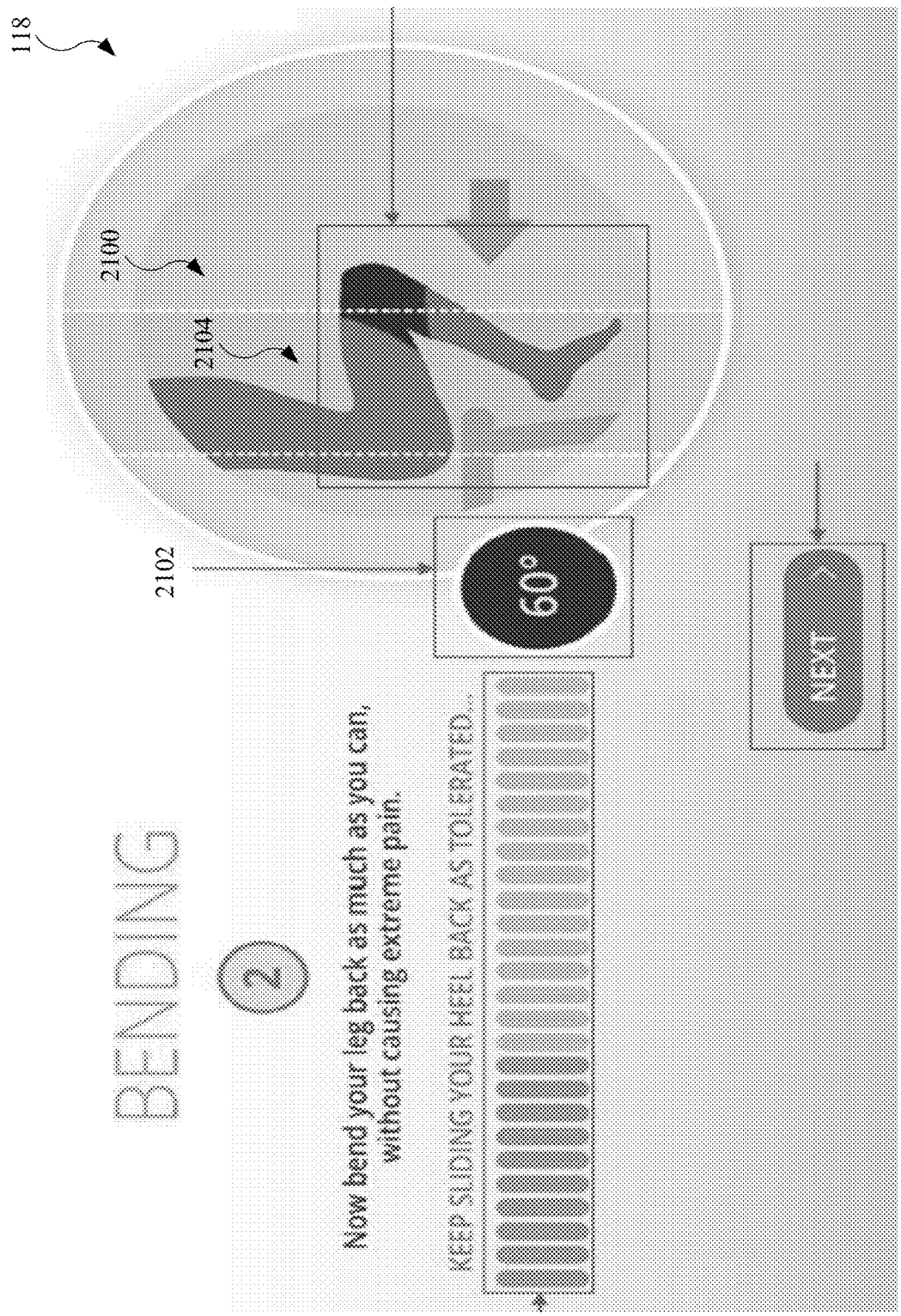

FIG. 21B illustrates the user interface 2100 with the graphical animation 2104 as the lower leg is extended farther away from the upper leg, and the angle 2102 changed from 84 to 60 degrees of extension. FIG. 21C illustrates the user interface 2100 with the graphical animation 2104 as the lower leg is extended even farther away from the upper leg. The computing device 102 may record the lowest angle to which the user 2108 is able to extend his or her leg as measured by the electronic device 106, such as the goniometer. The angle 2102 may be sent to the computing device 114 and that lowest angle may be presented on the clinical portal 126 as an extension statistic for that extension session. Further, a bar 2110 may be presented and the bar 2110 may fill from left to right over a set amount of time. A notification may indicate that the patient or user 2108 should push down on his or her knee over a set amount of time or until a set amount of time, minimum or maximum, has elapsed. The user interface 2100 in FIG. 21D is similar to FIG. 21C but it presents the angle of bend 2118, measured by the electronic device 106, such as the goniometer, as the user 2108 retracts his or her lower leg closer to his or her upper leg (e.g., during the bend 2122). As depicted, the graphical animation 2104 presented on the user interface 2100 in real-time depicts the angle of the knee matching the angle 2102. The computing device 102 may record the highest angle that the user 2108 is able to bend his or her leg as measured by the electronic device, such as the goniometer 106. That angle 2102 may be sent to the computing device 114 and that highest angle may be presented on the clinical portal 126 as a bend statistic for that bend session.

Figure 22:
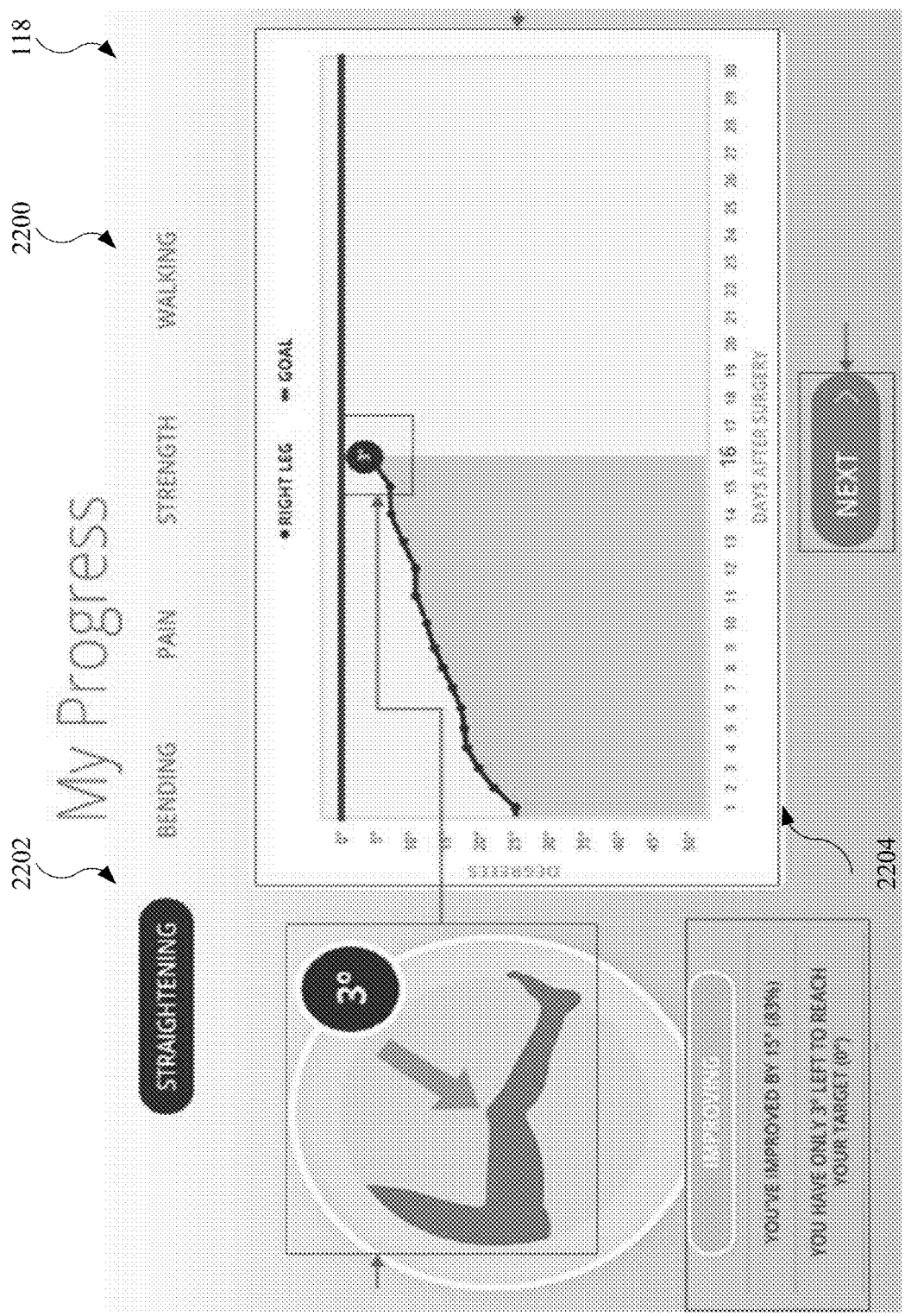
FIG. 22 illustrates an example user interface of the user portal, the user interface presenting a progress screen for a user extending the lower leg away from the upper leg according to certain embodiments of this disclosure.

FIG. 22 illustrates an example user interface 2200 of the user portal 118, the user interface 2200 presenting a progress report 2202 for a user extending the lower leg away from the upper leg according to certain embodiments of this disclosure. The user interface 2200 presents a graph 2204 with the degrees of extension on a y-axis and the days after surgery on the x-axis. The angles depicted in the graph 2204 are the lowest angles achieved each day. The user interface 2202 also depicts the lowest angle the user has achieved for extension and indicates an amount of improvement (83%) in extension since beginning the treatment plan. The user interface 2200 also indicates how many degrees are left before reaching a target extension angle.

Figure 23:
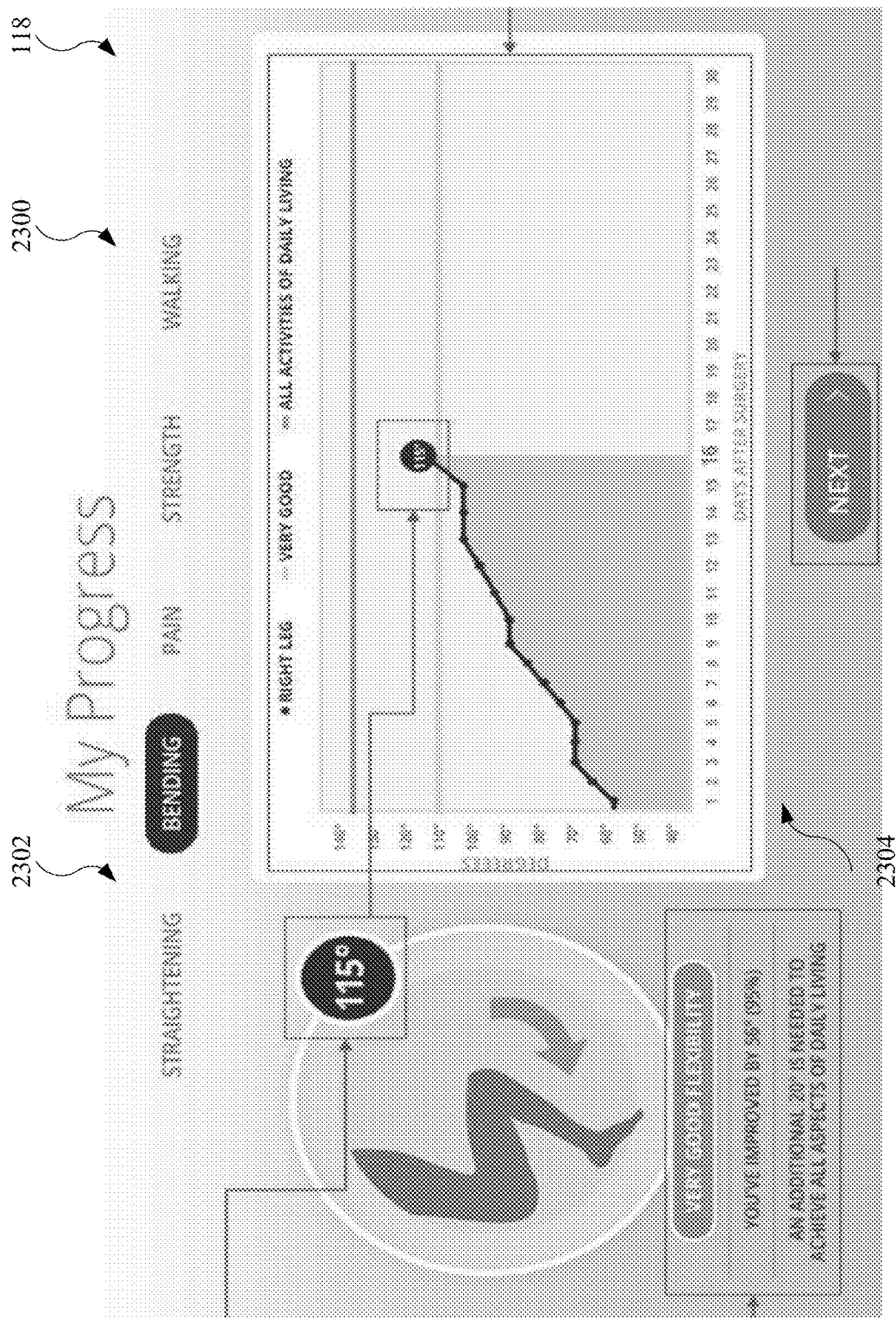
FIG. 23 illustrates an example user interface of the user portal, the user interface presenting a progress screen for a user bending the lower leg toward the upper leg according to certain embodiments of this disclosure.

FIG. 23 illustrates an example user interface 2300 of the user portal 118, the user interface 2300 presenting a progress screen 2302 for a user bending the lower leg toward the upper leg according to certain embodiments of this disclosure. The user interface 2300 presents a graph 2304 with the degrees of bend on a y-axis and the days after surgery on the x-axis. The angles depicted in the graph 2304 are the highest angles of bend achieved each day. The user interface 2202 also depicts the lowest angle the user has achieved for bending and indicates an amount of improvement (95%) in extension since beginning the treatment plan. The user interface 2200 also indicates how many degrees are left before reaching a target bend angle.

Figure 24:
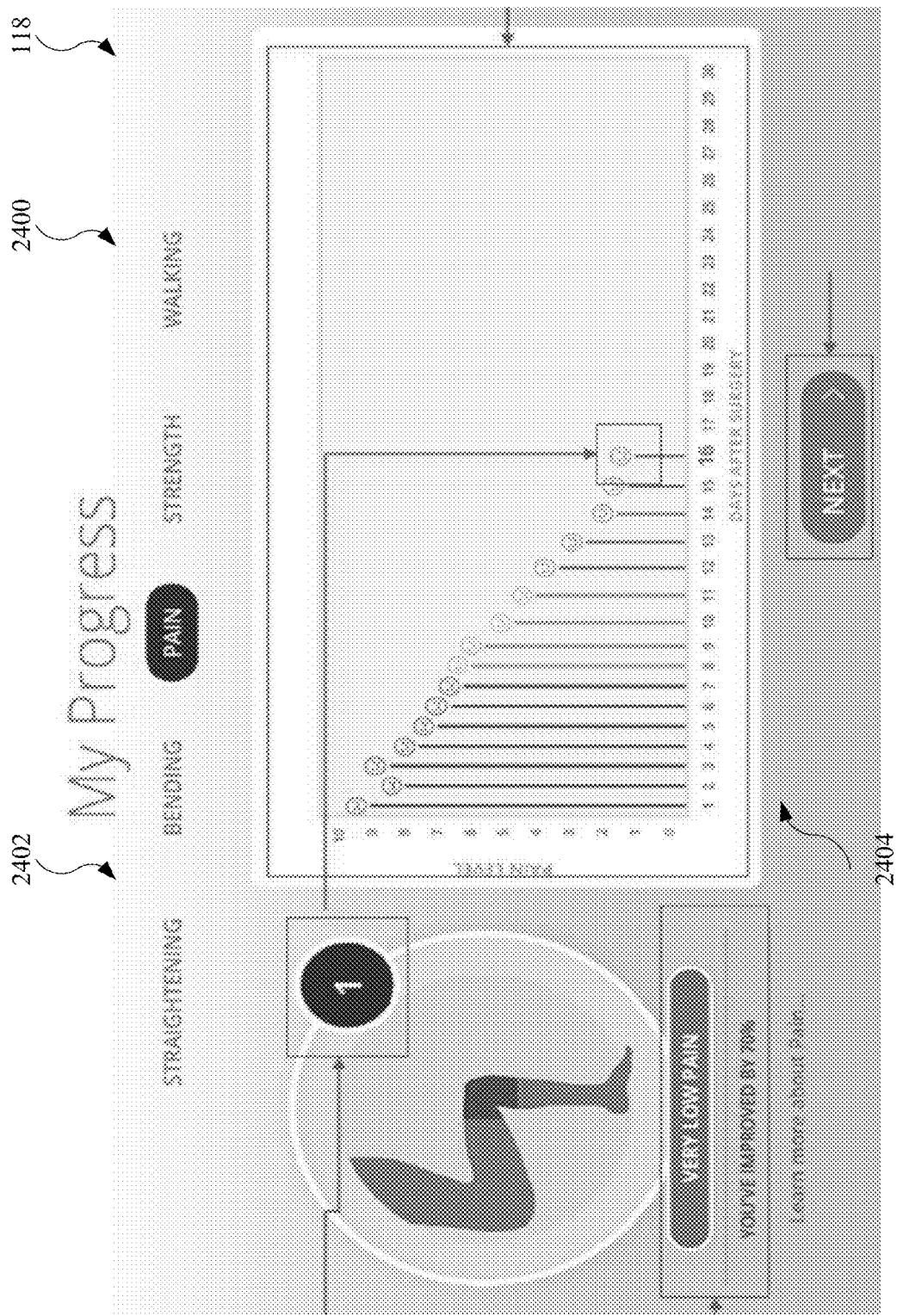
FIG. 24 illustrates an example user interface of the user portal, the user interface presenting a progress screen for a pain level of the user according to certain embodiments of this disclosure.

FIG. 24 illustrates an example user interface 2400 of the user portal 118, the user interface 2400 presenting a progress screen 2402 for a discomfort level of the user according to certain embodiments of this disclosure. The user interface 2400 presents a graph 2404 with the discomfort level on a y-axis and the days after surgery on the x-axis. The user interface 2400 also depicts the lowest discomfort level the user has reported and a notification indicating the amount of discomfort level the user has improved throughout the treatment plan.

Figure 25:
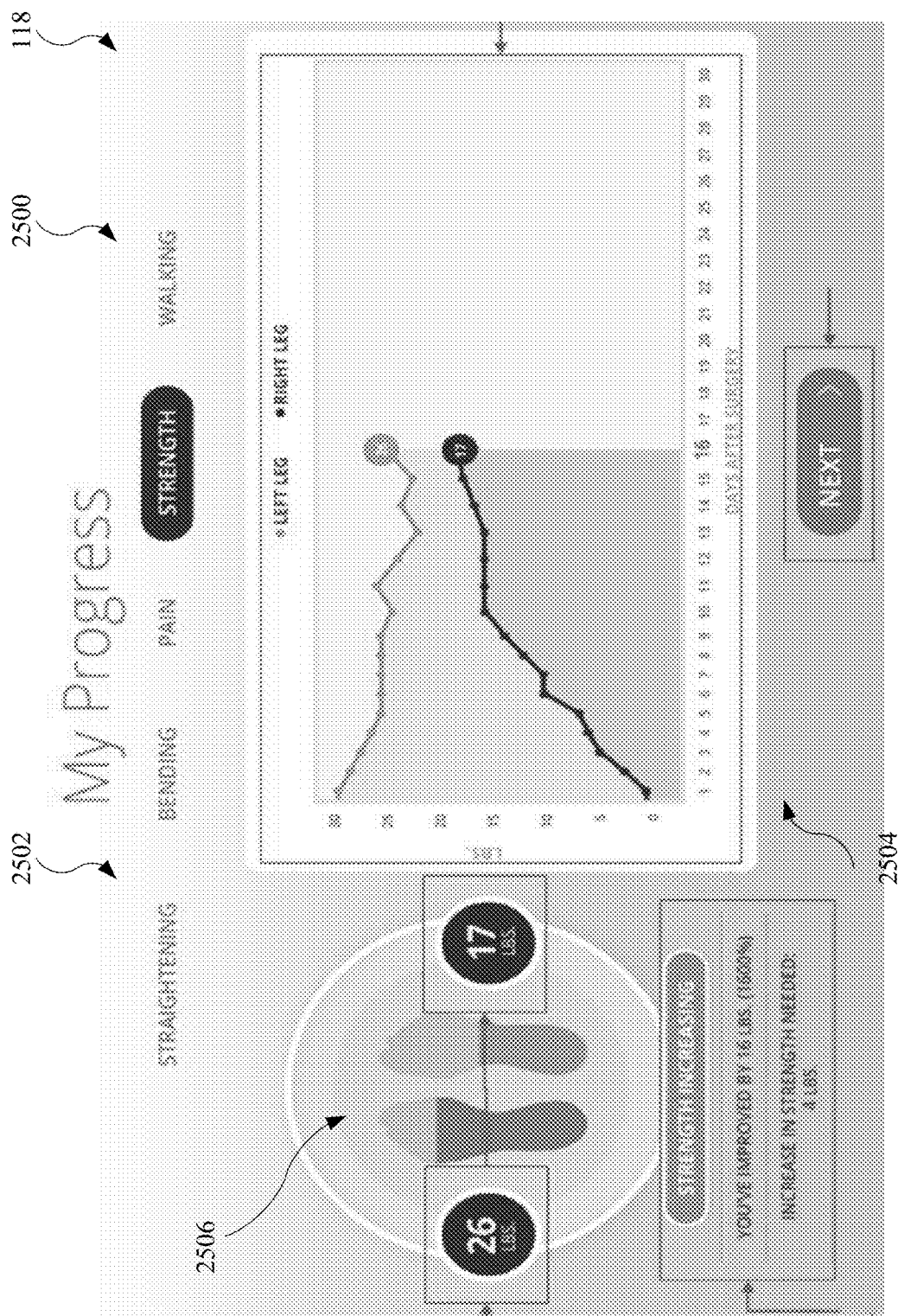
FIG. 25 illustrates an example user interface of the user portal, the user interface presenting a progress screen for a strength of a body part according to certain embodiments of this disclosure.

FIG. 25 illustrates an example user interface 2500 of the user portal 118, the user interface 118 presenting a progress screen 2502 for a strength of a body part according to certain embodiments of this disclosure. The user interface 2500 presents a graph 2504 with the pounds of force exerted by the patient for both the left leg and the right leg on a y-axis and the days after surgery on the x-axis. The graph 2504 may show an average for left and right leg for a current session. For the number of sessions a user does each day, the average pounds of force for those sessions may be displayed for prior days as well. The user interface 2500 also depicts graphical representations 2506 of the left and right feet and a maximum pound of force the user has exerted for the left and right leg. The maximum pounds of force depicted may be derived from when the electromechanical device is operating in the active mode. The user may select to see statistics for prior days and the average level of active sessions for that day may be presented as well. The user interface 2500 indicates the amount of improvement in strength in the legs and the amount of strength improvement needed to satisfy a target strength goal.

Figure 26:
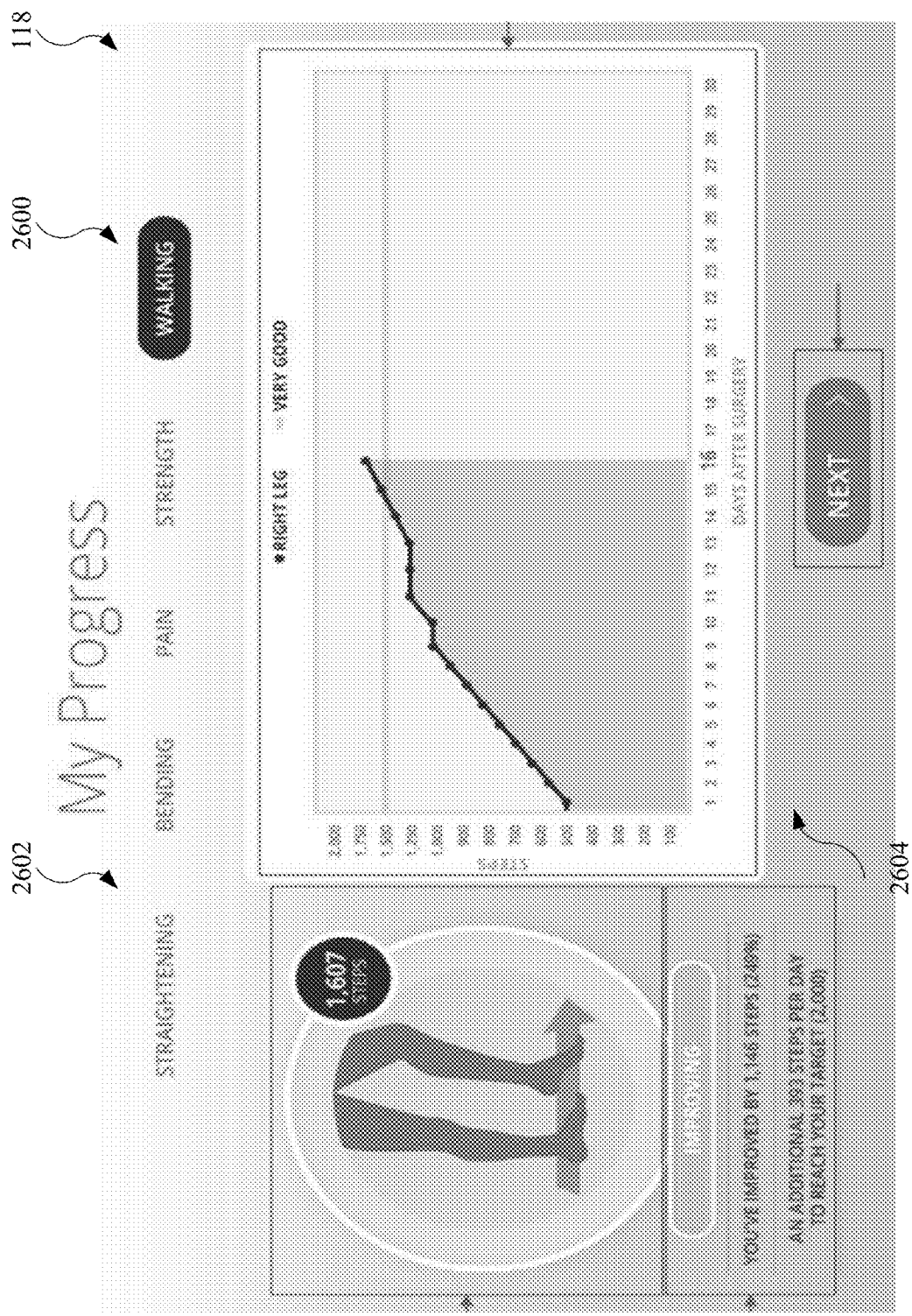
FIG. 26 illustrates an example user interface of the user portal, the user interface presenting a progress screen for an amount of steps of the user according to certain embodiments of this disclosure.

FIG. 26 illustrates an example user interface 2600 of the user portal 118, the user interface 118 presenting a progress screen 2602 for an amount of steps of the user according to certain embodiments of this disclosure. The user interface 2600 presents a graph 2604 with the number of steps taken by the user on a y-axis and the days after surgery on the x-axis. The user interface 2500 also depicts the highest number of steps the user has taken for amongst all of the days in the treatment plan, the amount the user has improved in steps per day since starting the treatment plan, and the amount of additional steps needed to meet a target step goal. The user may select to view prior days to see their total number of steps they have taken per day.

Figure 27:
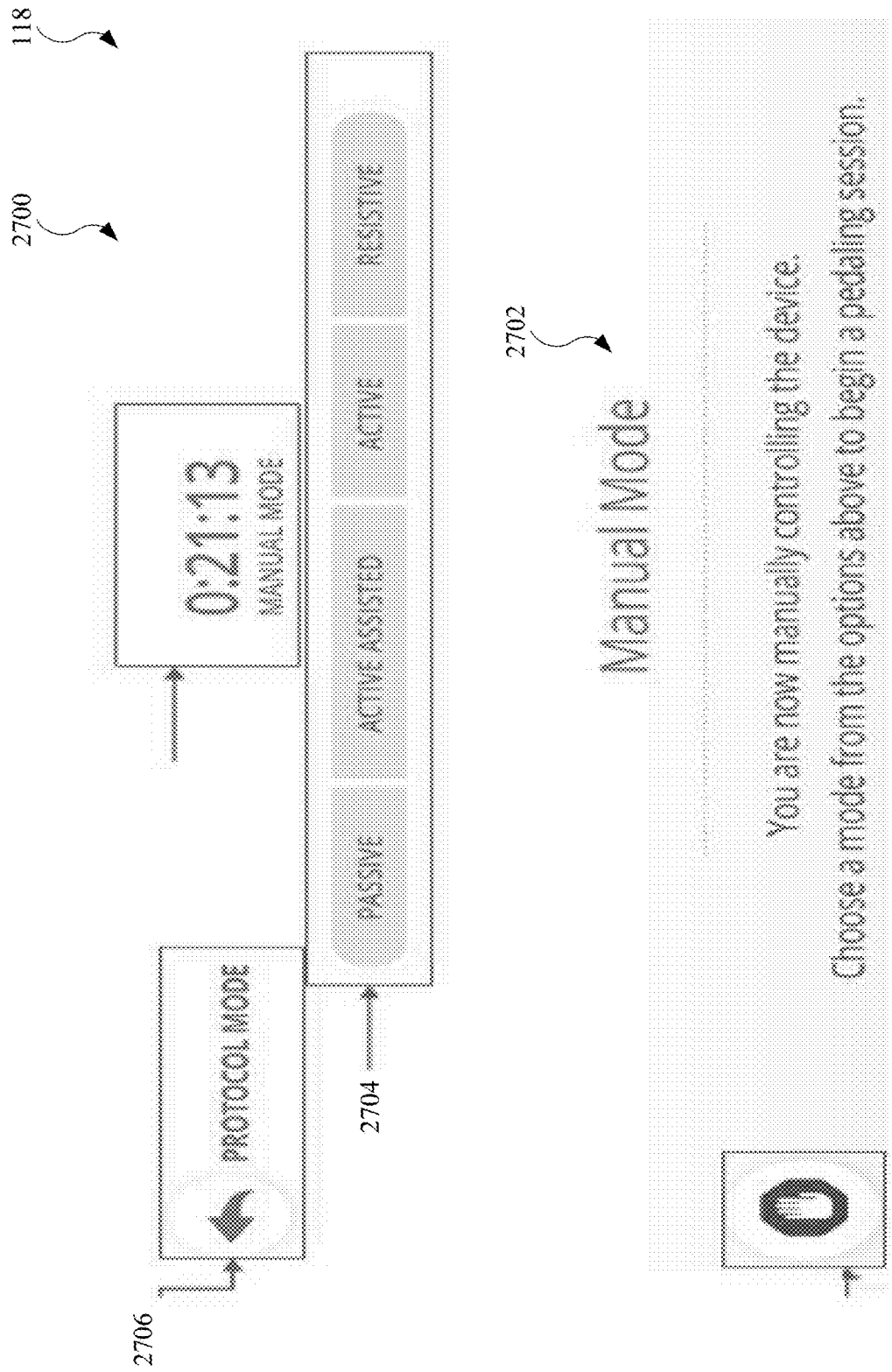
FIG. 27 illustrates an example user interface of the user portal, the user interface presenting that the electromechanical device is operating in a manual mode according to certain embodiments of this disclosure.

FIG. 27 illustrates an example user interface 2700 of the user portal 118, the user interface 2700 presenting that the electromechanical device 104 is operating in a manual mode 2702 according to certain embodiments of this disclosure. During the manual mode 2702, the user may set the speed, resistance, time to exercise, position of pedals, etc. That is, essentially the control system for the electromechanical device 104 may provide no assistance to operation of the electromechanical device 104. When the user selects any of the modes in the box 2704, a pedaling session may begin. Further, when the user selects button 2706, the user portal 118 may return to the user interface 1300 depicted in FIG. 13.

Figure 28:
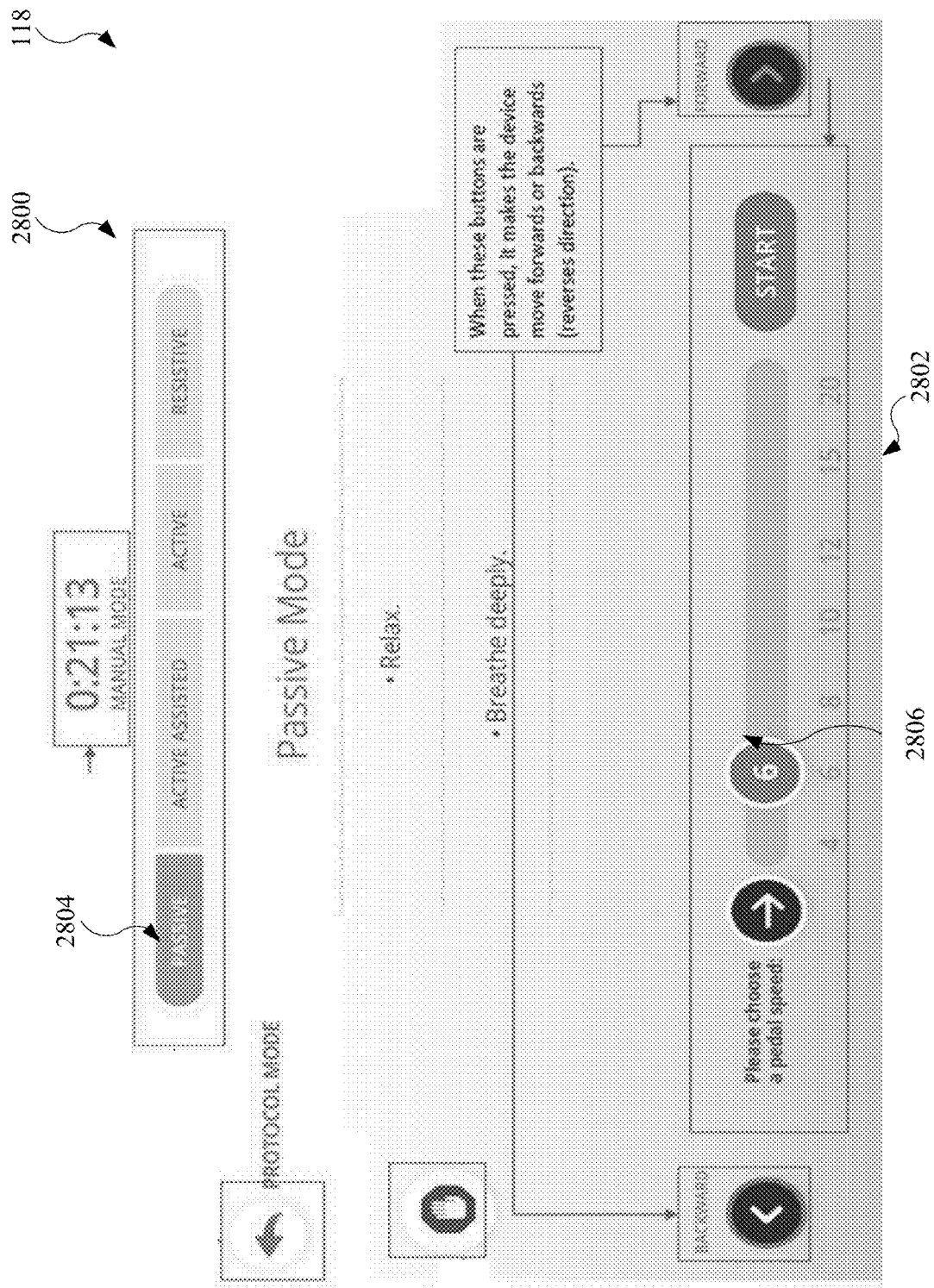
FIG. 28 illustrates an example user interface of the user portal, the user interface presenting an option to modify a speed of the electromechanical device operating in the passive mode according to certain embodiments of this disclosure.

FIG. 28 illustrates an example user interface 2800 of the user portal 118, the user interface 2800 presenting an option 2802 to modify a speed of the electromechanical device 104 operating in the passive mode 2802 according to certain embodiments of this disclosure. The user may slide button

2806 to adjust the speed as desired during the passive mode where the electric motor is providing the driving force of the radially-adjustable couplings.

Figure 29:
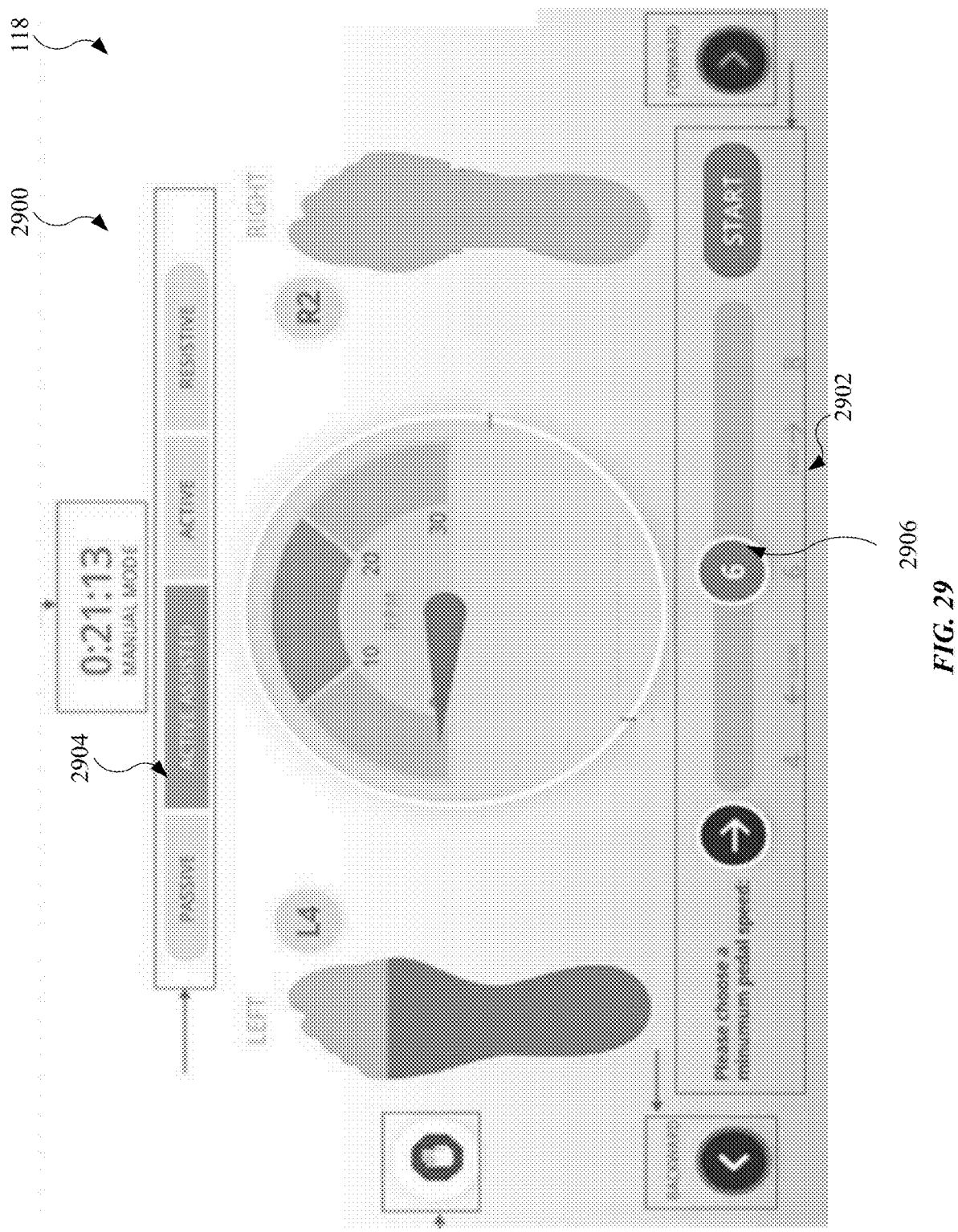
FIG. 29 illustrates an example user interface of the user portal, the user interface presenting an option to modify a minimum speed of the electromechanical device operating in the active-assisted mode according to certain embodiments of this disclosure.

FIG. 29 illustrates an example user interface 2900 of the user portal 118, the user interface 2900 presenting an option 2902 to modify a minimum speed of the electromechanical device 104 operating in the active-assisted mode 2904 according to certain embodiments of this disclosure. The user may slide button 2906 to adjust the minimum speed that the user should maintain before the electric motor begins providing driving force.

Figure 30:
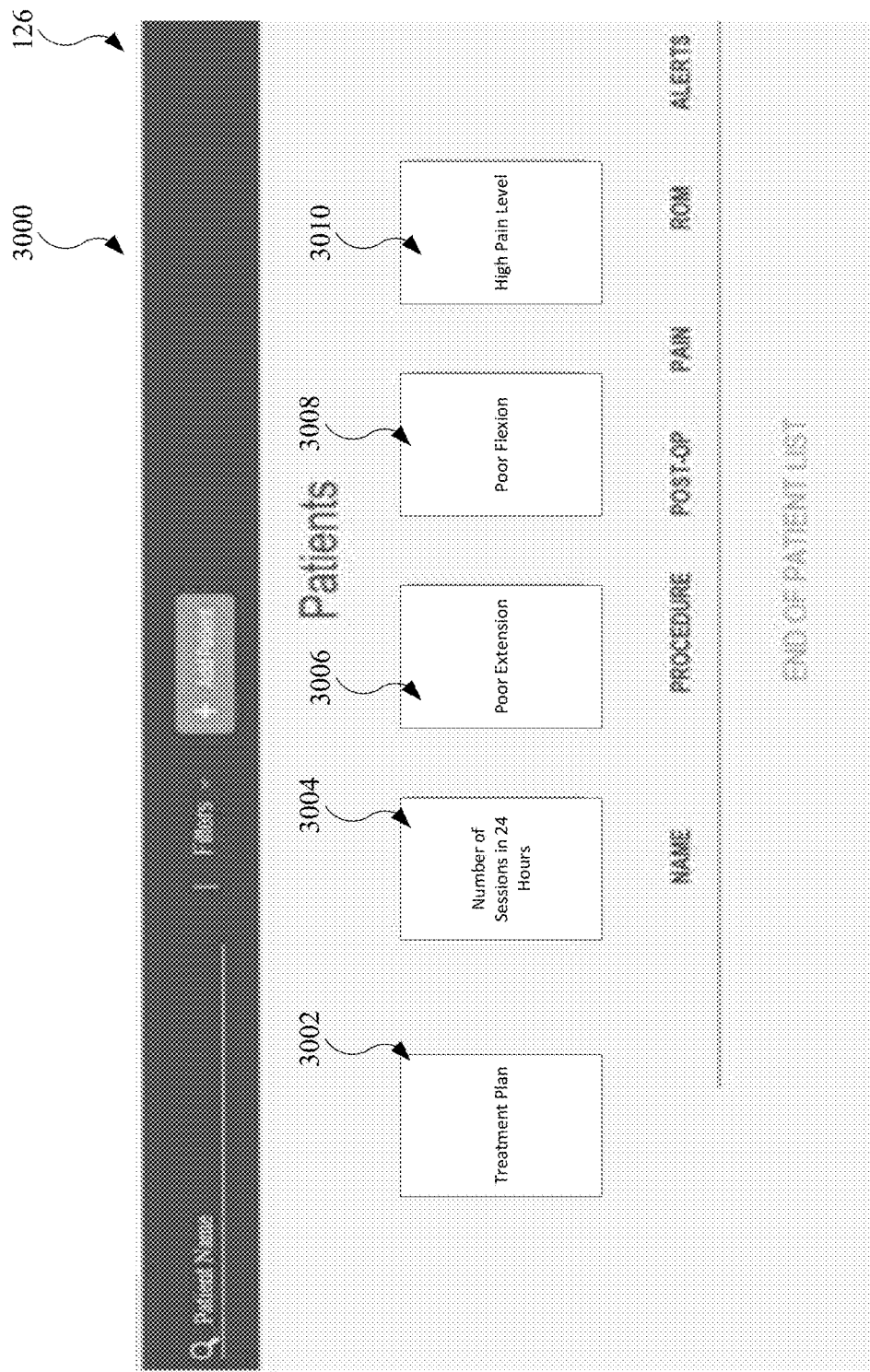
FIG. 30 illustrates an example user interface of the clinical portal, the user interface presenting various options available to the clinician according to certain embodiments of this disclosure.

FIG. 30 illustrates an example user interface 3000 of the clinical portal 118, the user interface 3000 presenting various options available to the clinician/physician according to certain embodiments of this disclosure. The clinical portal 118 may retrieve a list of patients for a particular physician who logs into the clinical portal 118. The list of patients may be stored on the computing device 114 or retrieved from the cloud-based computing system 116. A first option 3002 may enable the clinician to generate treatment plans for one or more of the patients, as described above. A second option 3004 may enable the clinician to view the number of sessions that each of the patients have completed in 24 hours. This may enable the clinician to determine whether the patients are keeping up with the treatment plan and send notifications to those patients that are not completing the sessions. A third option 3006 may enable the clinician to view the patients who have poor extension (e.g., angle of extension above a target extension for a particular stage in the treatment plan). A fourth option 3008 may enable the clinician to view the patients who have poor flexion (e.g., angle of bend below a target bend for a particular stage in the treatment plan). A fifth option 3010 may enable the clinician to view the patients reporting high pain levels. Regarding any of the options, the clinician can contact the user and inquire as to the status of their lack of participation, extension, flexion, pain level etc. The clinical portal 126 provides the benefit of direct monitoring of the patients progress by the clinician, which may enable faster and more effective recoveries.

Further, the clinical portal may include an option to control aspects of operating the electromechanical device 104. For example, the clinician may use the clinical portal 126 to adjust a position of a pedal based on angles of extension/bend received from the computing device 102 and/or the goniometer 106 in real-time while the user is engaged in a pedaling session or when the user is not engaged in the pedaling session. The clinical portal 126 may enable the clinician to adjust the amount of resistance provided by the electric motor 122 in response to determining an amount of force exerted by the user exceeds a target force threshold. The clinical portal 126 may enable the clinician to adjust the speed of the electric motor 122, and so forth.

Figure 31:
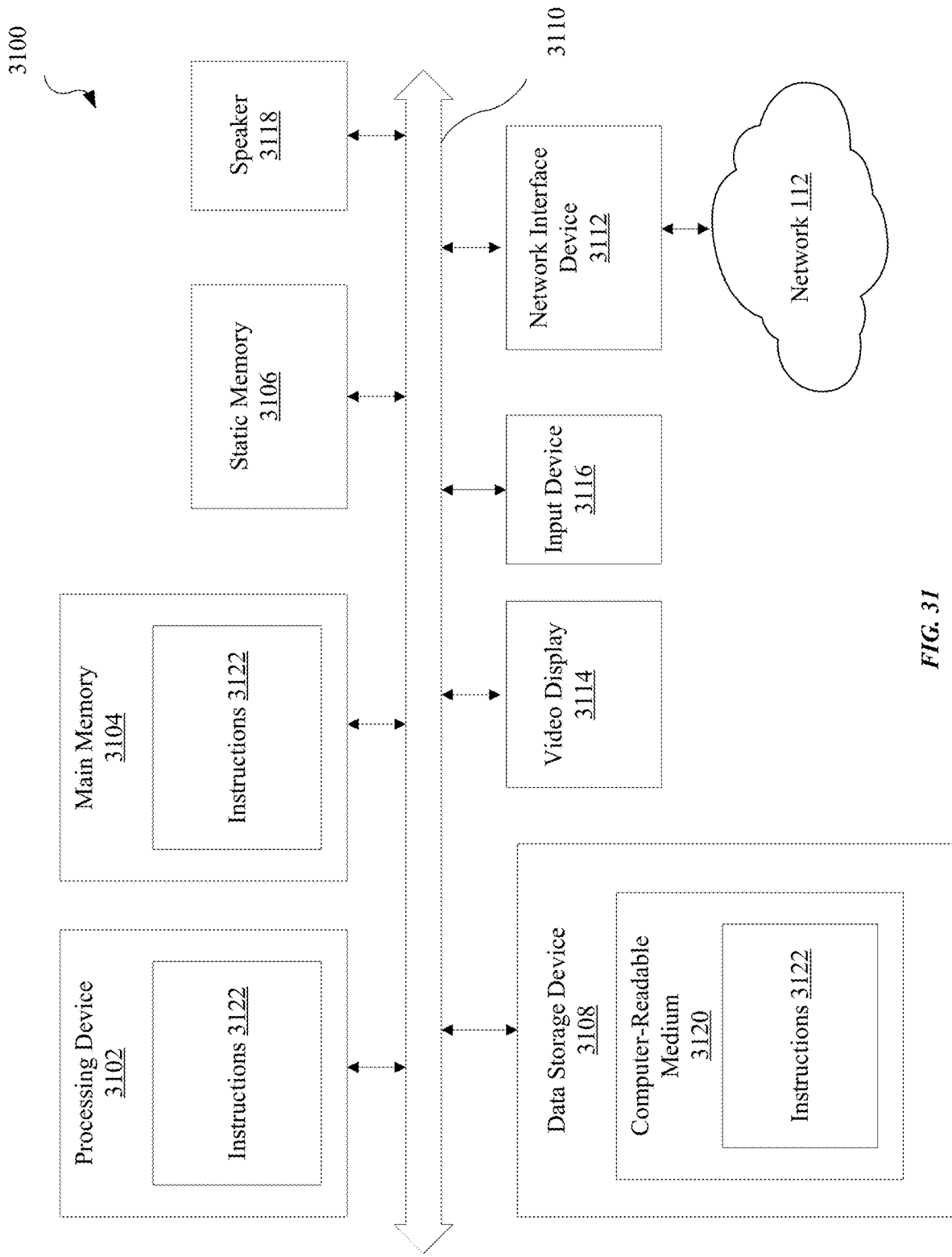
FIG. 31 illustrates an example computer system according to certain embodiments of this disclosure.

FIG. 31 illustrates example computer system 3100 which can perform any one or more of the methods described herein, in accordance with one or more aspects of the present disclosure. In one example, computer system 3100 may correspond to the computing device 102 (e.g., user computing device), the computing device 114 (e.g., clinician computing device), one or more servers of the cloud-based computing system 116, the training engine 130, the servers 128, the motor controller 120, the pedals 110, the goniometer 106, and/or the wristband 108 of FIG. 1. The computer system 3100 may be capable of executing user portal 118 and/or clinical portal 126 of FIG. 1. The computer system may be connected (e.g., networked) to other computer systems in a LAN, an intranet, an extranet, or the Internet. The computer system may operate in the capacity of a server in a client-server network environment. The computer system may be a personal computer (PC), a tablet computer, a motor controller, a goniometer, a wearable (e.g., wristband), a set-top box (STB), a personal Digital Assistant (PDA), a mobile phone, a camera, a video camera, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 3100 includes a processing device 3102, a main memory 3104 (e.g., read-only memory (ROM), flash memory, dynamic random access memory (DRAM) such as synchronous DRAM (SDRAM)), a static memory 3106 (e.g., flash memory, static random access memory (SRAM)), and a data storage device 3108, which communicate with each other via a bus 3110.

Processing device 3102 represents one or more general-purpose processing devices such as a microprocessor, central processing unit, or the like. More particularly, the processing device 3102 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 3102 may also be one or more special-purpose processing devices such as an application specific integrated circuit (ASIC), a field programmable gate array (FPGA), a digital signal processor (DSP), network processor, or the like. The processing device 3102 is configured to execute instructions for performing any of the operations and steps discussed herein.

The computer system 3100 may further include a network interface device 3112. The computer system 3100 also may include a video display 3114 (e.g., a liquid crystal display (LCD) or a cathode ray tube (CRT)), one or more input devices 3116 (e.g., a keyboard and/or a mouse), and one or more speakers 3118 (e.g., a speaker). In one illustrative example, the video display 3114 and the input device(s) 3116 may be combined into a single component or device (e.g., an LCD touch screen).

The data storage device 3116 may include a computer-readable medium 3120 on which the instructions 3122 (e.g., implementing control system, user portal, clinical portal, and/or any functions performed by any device and/or component depicted in the FIGURES and described herein) embodying any one or more of the methodologies or functions described herein is stored. The instructions 3122 may also reside, completely or at least partially, within the main memory 3104 and/or within the processing device 3102 during execution thereof by the computer system 3100. As such, the main memory 3104 and the processing device 3102 also constitute computer-readable media. The instructions 3122 may further be transmitted or received over a network via the network interface device 3112.

While the computer-readable storage medium 3120 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

Clause 1: An electromechanical device for rehabilitation, comprising:
one or more pedals coupled to one or more radially-adjustable couplings;
an electric motor coupled to the one or more pedals via the one or more radially-adjustable couplings;
a control system comprising one or more processing devices operatively coupled to the electric motor, wherein the one or more processing devices are configured to:
responsive to a first trigger condition occurring, control the electric motor to operate in a passive mode by independently driving the one or more radially-adjustable couplings rotationally coupled to the one or more pedals;
responsive to a second trigger condition occurring, control the electric motor to operate in an active-assisted mode by measuring revolutions per minute of the one or more radially-adjustable couplings, and causing the electric motor to drive the one or more radially-adjustable couplings rotationally coupled to the one or more pedals when the measured revolutions per minute satisfy a threshold condition; and
responsive to a third trigger condition occurring, control the electric motor to operate in a resistive mode by providing resistance to rotation of the one or more radially-adjustable couplings coupled to the one or more pedals.

Clause 2: The electromechanical device of any preceding Clause, wherein the one or more processing devices are further configured to, responsive to a fourth trigger condition occurring, control the electric motor to operate in an active mode by powering off to enable another source to drive the one or more radially-adjustable couplings via the one or more pedals.

Clause 3: The electromechanical device of any preceding Clause, wherein each of the first trigger condition, the second trigger condition, the third trigger condition, and the fourth trigger condition comprise at least one of an initiation of a pedaling session via a user interface of the control system, a period of time elapsing, a detected physical condition of a user operating the electromechanical device, a request received from the user via the user interface, or a request received via a computing device communicatively coupled to the control system.

Clause 4: The electromechanical device of any preceding Clause, wherein the radially-adjustable couplings are configured for translating rotational motion of the electric motor to radial motion of the pedals.

Clause 5: The electromechanical device of any preceding Clause, wherein the electric motor operates in each of the passive mode, the active-assisted mode, and the resistive mode for a respective period of time during a pedaling session based on a treatment plan for a user operating the electromechanical device.

Clause 6. The electromechanical device of any preceding Clause, wherein the one or more processing devices controls the electric motor to independently drive the one or more radially-adjustable couplings rotationally coupled to the one or more pedals at a controlled speed specified in a treatment plan for a user operating the electromechanical device while operating in the passive mode.

Clause 7: The electromechanical device of any preceding Clause, wherein the one or more processing devices are further configured to modify one or more positions of the one or more pedals on the one or more radially-adjustable couplings to change one or more diameters of ranges of motion of the one or more pedals during any of the plurality of modes throughout a pedaling session for a user operating the electromechanical device.

Clause 8: The electromechanical device of any preceding Clause, wherein the one or more processing devices are further configured to modify the position of one of the one or more pedals on one of the one or more radially-adjustable couplings to change the diameter of the range of motion of the one of the one or more pedals while maintaining another position of another of the one or more pedals on another of the one or more radially-adjustable couplings to maintain another diameter of another range of motion of the another pedal.

Clause 9: The electromechanical device of any preceding Clause, wherein the one or more processing devices are further configured to:
receive, from a goniometer worn by the user, at least one of an angle of extension of a joint of the user during a pedaling session or an angle of bend of the joint of the user during the pedaling session; and
modifying the one or more positions of the one or more pedals on the one or more radially-adjustable couplings to change the one or more diameters of the ranges of motion of the one or more pedals based on the at least one of the angle of extension of the joint of the user or the angle of bend of the joint of the user.

Clause 10: The electromechanical device of any preceding Clause, wherein the one or more processing devices are further configured to:
receive, from a goniometer worn by the user, a plurality of angles of extension between an upper leg and a lower leg at a knee of the user as the user extends the lower leg away from the upper leg via the knee; and
present, on a user interface of the control system, a graphical animation of the upper leg, the lower leg, and the knee of the user as the lower leg is extended away from the upper leg via the knee, wherein the graphical animation includes the plurality of angles of extension as the plurality of angles of extension change during the extension;
store a lowest value of the plurality of angles of extension as an extension statistic for an extension session, wherein a plurality of extension statistics is stored for a plurality of extension sessions specified by the treatment plan; and
present progress of the plurality of extension sessions throughout the treatment plan via a graphical element on the user interface presenting the plurality of extension statistics.

Clause 11: The electromechanical device of any preceding Clause, wherein the one or more processing devices are further configured to:
receive, from a goniometer worn by the user, a plurality of angles of bend between an upper leg and a lower leg at a knee of the user as the user retracts the lower leg closer to the upper leg via the knee; and
present, on a user interface of the control system, a graphical animation of the upper leg, the lower leg, and the knee of the user as the lower leg is retracted closer to the upper leg via the knee, wherein the graphical animation includes the plurality of angles of bend as the plurality of angles of bend changes during the bend;

store a highest value of the plurality of angles of bend as a bend statistic for a bend session, wherein a plurality of bend statistics is stored for a plurality of bend sessions specified by the treatment plan; and present progress of the plurality of bend sessions throughout the treatment plan via a graphical element on the user interface presenting the plurality of bend statistics.

Clause 12: The electromechanical device of any preceding Clause, wherein the one or more processing devices are further configured to:

receive, from a wearable device, an amount of steps taken by a user over a certain time period;

calculate whether the amount of steps satisfies a step threshold of a treatment plan for the user; and present the amount of steps taken by the user on a user interface and an indication of whether the amount of steps satisfies the step threshold.

Clause 13: The electromechanical device of any preceding Clause, wherein the one or more processing devices are further configured to:

receive a request to stop the one or more pedals from moving; and lock the electric motor to stop the one or more pedals from moving over a configured period of time.

Clause 14: The electromechanical device of any preceding Clause, wherein the one or more processing devices are further configured to:

receive, from one or more force sensors operatively coupled to the one or more pedals and the one or more processing devices, one or more measurements of force on the one or more pedals;

determine whether a user has fallen from the electromechanical device based on the one or more measurements of force; and responsive to determining that the user has fallen from the electromechanical device, lock the electric motor to stop the one or more pedals from moving.

Clause 15: The electromechanical device of any preceding Clause, wherein the one or more processing devices are further configured to:

receive, from an accelerometer of the control system, a measurement of acceleration of movement of the electromechanical device;

determine whether the electromechanical device has moved excessively relative to a vertical axis based on the measurement of acceleration; and responsive to determining that the electromechanical device has moved excessively relative to the vertical axis based on the measurement of acceleration, lock the electric motor to stop the one or more pedals from moving.

Clause 16: The electromechanical device of any preceding Clause, wherein the one or more processing devices are further to:

receive, from one or more force sensors operatively coupled to the one or more pedals, one or more measurements of force exerted by a user on the one or more pedals during a pedaling session; and present the respective one or more measurements of force on each of the one or more pedals on a separate respective graphical scale on a user interface while the user pedals during the pedaling session.

Clause 17: The electromechanical device of any preceding Clause, wherein the one or more processing devices are further to present a first notification on the user interface when the one or more measurements of force satisfy a pressure threshold and present a second notification on the user interface when the one or more measurements do not satisfy the pressure threshold.

Clause 18: The electromechanical device of any preceding Clause, wherein the one or more processing devices are further to provide an indicator to the patient based on the one or more measurements of force, wherein the indicator comprises at least one of (1) providing haptic feedback in the pedals, handles, or seat, (2) providing visual feedback on the user interface, (3) providing audio feedback via an audio subsystem of the electromechanical device, or (4) illuminating a warning light of the electromechanical device.

Clause 19: The electromechanical device of any preceding Clause, wherein the one or more processing devices are further to lock the electric motor to prevent the one or more pedals from moving for a certain amount of time after a pedaling session is complete, wherein the pedaling session comprises operating in the passive mode, the active-passive mode, and the resistive mode for respective periods of time.

Clause 20: The electromechanical device of any preceding Clause, wherein the one or more processing devices are further configured to:

control an imaging system to capture an image of a body part of the patient being rehabilitated; and transmit the image of the body part to a computing device operated by a clinician, wherein the computing device is communicatively coupled to the control system.

Clause 21. The electromechanical device of claim any preceding Clause, wherein the first trigger condition, the second trigger condition, and the third trigger condition are set based on a treatment plan, wherein the treatment plan was generated by one or more machine learning models trained to output the treatment plan based on input related to at least one of a procedure the user underwent or a characteristic of the user.

Clause 22: The electromechanical device of any preceding Clause, wherein the one or more processing devices are further configured to:

receive, from a wristband worn by the user, a heartbeat of the user as the user operates the electromechanical device; and responsive to determining that the heartbeat exceeds a target heartbeat condition, control the electric motor to reduce the resistance provided to the rotation of the one or more radially-adjustable couplings coupled to the one or more pedals.

Clause 23: A method for controlling, via a processing device, an electromechanical device, comprising:

receiving configuration information for a pedaling session;

setting a resistance parameter and a maximum pedal force parameter based on the configuration information for the pedaling session;

measuring force applied to pedals of the electromechanical device as a user pedals the electromechanical device, wherein an electric motor of the electromechanical device provides resistance during the pedaling session based on the resistance parameter;

determining whether the measured force exceeds the maximum pedal force parameter; and responsive to determining that the measured force exceeds the maximum pedal force parameter, reducing the resistance parameter so the electric motor applies less resistance during the pedaling session to maintain a revolutions per minute threshold.

Clause 24: The method of any preceding Clause, further comprising, responsive to determining that the measured force does not exceed the maximum pedal force parameter, maintaining the same maximum pedal force parameter during the pedaling session.

Clause 25: The method of any preceding Clause, wherein the configuration information is received from a server computing device that received the configuration information from a clinical portal presented on a computing device.

Clause 26: The method of any preceding Clause, wherein the configuration information comprises configuration information specified for a stage of a plurality of stages in a treatment plan for rehabilitating a body part of the user.

Clause 27: The method of any preceding Clause, further comprising receiving a selection of the configuration information from a user interface presented to the user.

Clause 28: The method of claim any preceding Clause, further comprising:
responsive to receiving the configuration information, determining that a trigger condition has occurred; and
controlling, based on the trigger condition occurring, the electric motor to operate in a resistive mode by providing a resistance to rotation of the pedals based on the trigger condition.

Clause 29: The method of any preceding Clause, further comprising:
determining that a trigger condition has occurred; and
controlling, based on the trigger condition occurring, the electric motor to operate in a passive mode by independently driving one or more radially-adjustable couplings coupled to the pedals in a rotational fashion.

Clause 30: The method of any preceding Clause, further comprising:
determining that a trigger condition has occurred; and
controlling, based on the trigger condition occurring, the electric motor to operate in an active-assisted mode by measuring revolutions per minute of one or more radially-adjustable couplings coupled to the pedals and causing the electric motor to drive in a rotational fashion the one or more radially-adjustable couplings coupled to the pedals when the measured revolutions per minute satisfy a threshold condition.

Clause 31: The method of any preceding Clause, further comprising:
receiving, from a goniometer worn by the user, a plurality of angles of extension between an upper leg and a lower leg at a knee of the user, wherein the plurality of angles is measured as the user extends the lower leg away from the upper leg via the knee;
receiving, from the goniometer worn by the user, a plurality of angles of bend between the upper leg and the lower leg at the knee of the user, wherein the plurality of angles is measured as the user retracts the lower leg closer to the upper leg via the knee; and
determining whether a range of motion threshold condition is satisfied based on the plurality of angles of extension and the plurality of angles of bend.

Clause 32: The method of any preceding Clause, wherein the pedals are coupled to radially-adjustable couplings, and the method further comprising:
responsive to determining that the range of motion threshold condition is satisfied, modifying a position of one of the pedals on one of the radially-adjustable couplings to change a diameter of a range of motion of the one of the pedals.

Clause 33: An electronic device, comprising:
one or more memory devices storing instructions;
one or more network interface cards;
one or more goniometers; and
one or more processing devices operatively coupled to the one or more memory devices, the one or more network interface cards, and the one or more goniometers, wherein the one or more processing devices execute the instructions to:
receive a plurality of angles from the one or more goniometers, wherein the plurality of angles comprises at least one of angles of extension of a lower leg of a user extended away from an upper leg at a knee or angles of bend of the lower leg retracting closer toward the upper leg; and
transmit, via the one or more network interface cards, the plurality of angles to a computing device controlling an electromechanical device.

Clause 34: The electronic device of any preceding Clause, wherein the plurality of angles is received while the user is pedaling one or more pedals of the electromechanical device.

Clause 35: The electronic device of any preceding Clause, wherein the transmitting the plurality of angles to the computing device causes the computing device to adjust a position of one of one or more pedals on a radially-adjustable coupling based on the plurality of angles satisfying a range of motion threshold condition.

Clause 36: The electronic device of any preceding Clause, wherein the position of the pedal is adjusted to increase a diameter of a range of motion transited by the upper leg, the lower leg, and the knee of the user as the user operates the one of the pedals.

Clause 37: The electronic device of any preceding Clause, wherein the transmitting the plurality of angles to the computing device causes the computing device to present the plurality of angles in a graphical animation of the lower leg and the upper leg moving in real-time during the extension or the bend.

Clause 38: The electronic device of any preceding Clause, wherein the one or more processing devices are further to transmit, via the one or more network interface cards, the plurality of angles to another computing device to cause the another computing device to present the plurality of angles on a user interface of a clinical portal.

What is claimed is:

1. An electromechanical device for rehabilitation, comprising:
one or more pedals coupled to one or more radially-adjustable couplings;
an electric motor coupled to the one or more pedals via the one or more radially-adjustable couplings;
a control system comprising one or more processing devices operatively coupled to the electric motor, wherein the one or more processing devices are configured to:
responsive to a first trigger condition occurring, control the electric motor to operate in a passive mode by independently driving the one or more radially-adjustable couplings rotationally coupled to the one or more pedals;
responsive to a second trigger condition occurring, control the electric motor to operate in an active-assisted mode by:
measuring revolutions per minute of the one or more radially-adjustable couplings, and
causing the electric motor to drive the one or more radially-adjustable couplings rotationally coupled to the one or more pedals when the measured revolutions per minute satisfy a threshold condition; and responsive to a third trigger condition occurring, control the electric motor to operate in a resistive mode by providing resistance to rotation of the one or more radially-adjustable couplings coupled to the one or more pedals, wherein the first trigger condition, the second trigger condition, and the third trigger condition are set based on a treatment plan, wherein the treatment plan was generated by one or more machine learning models trained to output the treatment plan based on input related to at least one of a procedure the user underwent or a characteristic of the user.

2. The electromechanical device of claim 1, wherein the one or more processing devices are further configured to, responsive to a fourth trigger condition occurring, control the electric motor to operate in an active mode by powering off to enable another source to drive the one or more radially-adjustable couplings via the one or more pedals, wherein each of the first trigger condition, the second trigger condition, the third trigger condition, and the fourth trigger condition comprise at least one of an initiation of a pedaling session via a user interface of the control system, a period of time elapsing, a detected physical condition of a user operating the electromechanical device, a request received from the user via the user interface, or a request received via a computing device communicatively coupled to the control system.

3. The electromechanical device of claim 1, wherein the radially-adjustable couplings are configured for translating rotational motion of the electric motor to radial motion of the pedals.

4. The electromechanical device of claim 1, wherein the electric motor operates in each of the passive mode, the active-assisted mode, and the resistive mode for a respective period of time during a pedaling session based on a treatment plan for a user operating the electromechanical device.

5. The electromechanical device of claim 1, wherein the one or more processing devices controls the electric motor to independently drive the one or more radially-adjustable couplings rotationally coupled to the one or more pedals at a controlled speed specified in a treatment plan for a user operating the electromechanical device while operating in the passive mode.

6. The electromechanical device of claim 1, wherein the one or more processing devices are further configured to modify one or more positions of the one or more pedals on the one or more radially-adjustable couplings to change one or more diameters of ranges of motion of the one or more pedals during any of the plurality of modes throughout a pedaling session for a user operating the electromechanical device, wherein the one or more processing devices are further configured to modify the position of one of the one or more pedals on one of the one or more radially-adjustable couplings to change the diameter of the range of motion of the one of the one or more pedals while maintaining another position of another of the one or more pedals on another of the one or more radially-adjustable couplings to maintain another diameter of another range of motion of the another pedal.

7. The electromechanical device of claim 6, wherein the one or more processing devices are further configured to:

receive, from a goniometer worn by the user, at least one of an angle of extension of a joint of the user during a pedaling session or an angle of bend of the joint of the user during the pedaling session; and modifying the one or more positions of the one or more pedals on the one or more radially-adjustable couplings to change the one or more diameters of the ranges of motion of the one or more pedals based on the at least one of the angle of extension of the joint of the user or the angle of bend of the joint of the user.

8. The electromechanical device of claim 1, wherein the one or more processing devices are further configured to:

receive, from a goniometer worn by the user, a plurality of angles of extension between an upper leg and a lower leg at a knee of the user as the user extends the lower leg away from the upper leg via the knee; and present, on a user interface of the control system, a graphical animation of the upper leg, the lower leg, and the knee of the user as the lower leg is extended away from the upper leg via the knee, wherein the graphical animation includes the plurality of angles of extension as the plurality of angles of extension change during the extension;

store a lowest value of the plurality of angles of extension as an extension statistic for an extension session, wherein a plurality of extension statistics is stored for a plurality of extension sessions specified by the treatment plan; and present progress of the plurality of extension sessions throughout the treatment plan via a graphical element on the user interface presenting the plurality of extension statistics.

9. The electromechanical device of claim 1, wherein the one or more processing devices are further configured to:

receive, from a goniometer worn by the user, a plurality of angles of bend between an upper leg and a lower leg at a knee of the user as the user retracts the lower leg closer to the upper leg via the knee; and present, on a user interface of the control system, a graphical animation of the upper leg, the lower leg, and the knee of the user as the lower leg is retracted closer to the upper leg via the knee, wherein the graphical animation includes the plurality of angles of bend as the plurality of angles of bend changes during the bend;

store a highest value of the plurality of angles of bend as a bend statistic for a bend session, wherein a plurality of bend statistics is stored for a plurality of bend sessions specified by the treatment plan; and present progress of the plurality of bend sessions throughout the treatment plan via a graphical element on the user interface presenting the plurality of bend statistics.

10. The electromechanical device of claim 1, wherein the one or more processing devices are further configured to:

receive, from a wearable device, an amount of steps taken by a user over a certain time period;

calculate whether the amount of steps satisfies a step threshold of a treatment plan for the user; and present the amount of steps taken by the user on a user interface and an indication of whether the amount of steps satisfies the step threshold.

11. The electromechanical device of claim 1, wherein the one or more processing devices are further configured to:

receive a request to stop the one or more pedals from moving; and lock the electric motor to stop the one or more pedals from moving over a configured period of time.

12. The electromechanical device of claim 1, wherein the one or more processing devices are further configured to:

receive, from one or more force sensors operatively coupled to the one or more pedals and the one or more processing devices, one or more measurements of force on the one or more pedals;
determine whether a user has fallen from the electromechanical device based on the one or more measurements of force; and
responsive to determining that the user has fallen from the electromechanical device, lock the electric motor to stop the one or more pedals from moving.

13. The electromechanical device of claim 1, wherein the one or more processing devices are further configured to:
receive, from an accelerometer of the control system, a measurement of acceleration of movement of the electromechanical device;
determine whether the electromechanical device has moved excessively relative to a vertical axis based on the measurement of acceleration; and
responsive to determining that the electromechanical device has moved excessively relative to the vertical axis based on the measurement of acceleration, lock the electric motor to stop the one or more pedals from moving.

14. The electromechanical device of claim 1, wherein the one or more processing devices are further to:
receive, from one or more force sensors operatively coupled to the one or more pedals, one or more measurements of force exerted by a user on the one or more pedals during a pedaling session;
present the respective one or more measurements of force on each of the one or more pedals on a separate respective graphical scale on a user interface while the user pedals during the pedaling session,
wherein the one or more processing devices are further to present a first notification on the user interface when the one or more measurements of force satisfy a pressure threshold and present a second notification on the user interface when the one or more measurements do not satisfy the pressure threshold, and
wherein the one or more processing devices are further to provide an indicator to the patient based on the one or more measurements of force, wherein the indicator comprises at least one of (1) providing haptic feedback in the pedals, handles, or seat, (2) providing visual feedback on the user interface, (3) providing audio feedback via an audio subsystem of the electromechanical device, or (4) illuminating a warning light of the electromechanical device.

15. The electromechanical device of claim 1, wherein the one or more processing devices are further to lock the electric motor to prevent the one or more pedals from moving for a certain amount of time after a pedaling session is complete, wherein the pedaling session comprises operating in the passive mode, the active-passive mode, and the resistive mode for respective periods of time.

16. The electromechanical device of claim 1, wherein the one or more processing devices are further configured to:
control an imaging system to capture an image of a body part of the patient being rehabilitated; and
transmit the image of the body part to a computing device operated by a clinician, wherein the computing device is communicatively coupled to the control system.

17. The electromechanical device of claim 1, wherein the one or more processing devices are further configured to:
receive, from a wristband worn by the user, a heartbeat of the user as the user operates the electromechanical device; and
responsive to determining that the heartbeat exceeds a target heartbeat condition, control the electric motor to reduce the resistance provided to the rotation of the one or more radially-adjustable couplings coupled to the one or more pedals.

18. A system comprising:
one or more pedals coupled to one or more radially-adjustable couplings;
an electric motor coupled to the one or more pedals via the one or more radially-adjustable couplings;
a control system comprising one or more processing devices operatively coupled to the electric motor, wherein the one or more processing devices are configured to:
responsive to a first trigger condition occurring, control the electric motor to operate in a passive mode by independently driving the one or more radially-adjustable couplings rotationally coupled to the one or more pedals;
responsive to a second trigger condition occurring, control the electric motor to operate in an active-assisted mode by:
measuring revolutions per minute of the one or more radially-adjustable couplings, and
causing the electric motor to drive the one or more radially-adjustable couplings rotationally coupled to the one or more pedals when the measured revolutions per minute satisfy a threshold condition; and
responsive to a third trigger condition occurring, control the electric motor to operate in a resistive mode by providing resistance to rotation of the one or more radially-adjustable couplings coupled to the one or more pedals,
wherein the first trigger condition, the second trigger condition, and the third trigger condition are set based on a treatment plan, wherein the treatment plan was generated by one or more machine learning models trained to output the treatment plan based on input related to at least one of a procedure the user underwent or a characteristic of the user.

19. A method for controlling, via a processing device, an electromechanical device, comprising:
responsive to a first trigger condition occurring, controlling an electric motor of the electromechanical device to operate in a passive mode by independently driving one or more radially-adjustable couplings rotationally coupled to one or more pedals; of the electromechanical device
responsive to a second trigger condition occurring, controlling the electric motor to operate in an active-assisted mode by:
measuring revolutions per minute of the one or more radially-adjustable couplings, and
causing the electric motor to drive the one or more radially-adjustable couplings rotationally coupled to the one or more pedals when the measured revolutions per minute satisfy a threshold condition; and
responsive to a third trigger condition occurring, controlling the electric motor to operate in a resistive mode by providing resistance to rotation of the one or more radially-adjustable couplings coupled to the one or more pedals,
wherein the first trigger condition, the second trigger condition, and the third trigger condition are set based on a treatment plan, wherein the treatment plan was generated by one or more machine learning models trained to output the treatment plan based on input related to at least one of a procedure the user underwent or a characteristic of the user.

* * * * *